United States Patent
Hasegawa et al.

(10) Patent No.: US 11,609,229 B2
(45) Date of Patent: Mar. 21, 2023

(54) FLUORESCENCE COUNTING SYSTEM FOR QUANTIFYING VIRUSES OR ANTIBODIES ON AN IMMOBILIZED METAL SUBSTRATE BY USING AN ANTIGEN-ANTIBODY REACTION

(71) Applicant: MYTECH CO. LTD., Hyogo (JP)

(72) Inventors: Yuki Hasegawa, Kobe (JP); Katsuyuki Hasegawa, Kobe (JP)

(73) Assignee: MYTECH CO. LTD., Hyogo (JP)

( * ) Notice: Subject to any disclaimer, the term of this patent is extended or adjusted under 35 U.S.C. 154(b) by 0 days.

(21) Appl. No.: 17/096,678

(22) Filed: Nov. 12, 2020

(65) Prior Publication Data

US 2021/0341468 A1  Nov. 4, 2021

(30) Foreign Application Priority Data

Apr. 30, 2020 (JP) .............................. JP2020-80227
May 18, 2020 (JP) .............................. JP2020-86846

(51) Int. Cl.
G01N 33/543 (2006.01)
G01N 33/553 (2006.01)
G01N 33/569 (2006.01)

(52) U.S. Cl.
CPC ..... *G01N 33/54306* (2013.01); *G01N 33/553* (2013.01); *G01N 33/56983* (2013.01); *G01N 2333/165* (2013.01)

(58) Field of Classification Search
CPC .................................. G01N 2333/165; G01N 33/56983–33/56994;
(Continued)

(56) References Cited

U.S. PATENT DOCUMENTS

| 9,139,907 B2* | 9/2015 | Hasegawa ............... C01B 17/64 |
| 10,215,700 B2* | 2/2019 | Hasegawa .......... G01N 21/6486 |
| 10,234,394 B2* | 3/2019 | Chou ..................... B82Y 15/00 |
| 2005/0112607 A1 | 5/2005 | Bamdad et al. |

(Continued)

FOREIGN PATENT DOCUMENTS

| EP | 3574308 A1 | 12/2019 |
| JP | 2016-080565 A | 5/2016 |

(Continued)

OTHER PUBLICATIONS

JP 2016080565A, machine translation provided by Patent Translate, retrieved from https://worldwide.espacenet.com/publicationDetails/biblio?ll=0&ND=3&adjacent=true&locale=en_EP&FT=D&date=20160516&CC=JP&NR=2016080565A&KC=A on Mar. 30, 2021, 11 pages total (Year: 2016).*

(Continued)

*Primary Examiner* — Melanie Brown
*Assistant Examiner* — Jennifer H. Tieu
(74) *Attorney, Agent, or Firm* — Dave Law Group LLC; Raj S. Dave

(57) ABSTRACT

The present invention relates to a system capable of performing simple and rapid inspection of an antigen equivalent to the immune chromatographic method with accuracy good as a PCR method. An embodiment relates to a novel fluorescence counting system for quantifying viruses or antibodies in an analyte which comprises an unit of providing an antigen or antibody phase solidified substrate by an aggregation method with quantum crystals, an unit for making a labeling liquor and labeling a virus or an antibody to be measured in the analyte by an antigen-antibody method, an unit of exciting the fluorescently labeled virus or antibody by a surface plasmon excitation method, and an (Continued)

unit of counting fluorescent points in an excited fluorescent screen to quantify the virus or antibody in the analyte.

7 Claims, 32 Drawing Sheets

(58) Field of Classification Search
CPC ...... G01N 33/53–33/577; G01N 33/00; G01N 33/54306; G01N 33/553
See application file for complete search history.

(56) References Cited

U.S. PATENT DOCUMENTS

| | | | |
|---|---|---|---|
| 2009/0202119 A1* | 8/2009 | Hefti | A61B 1/043 382/128 |
| 2009/0275145 A1* | 11/2009 | Lakowicz | G01N 21/6452 436/501 |
| 2013/0230866 A1 | 9/2013 | Miyashita et al. | |
| 2014/0030700 A1* | 1/2014 | Geddes | G01N 21/648 435/5 |
| 2014/0256593 A1* | 9/2014 | Szmacinski | G01N 33/54373 506/9 |
| 2015/0119722 A1* | 4/2015 | Kaneko | A61B 5/0071 600/476 |
| 2016/0146799 A1* | 5/2016 | Robinson | C12Q 1/6834 506/4 |

FOREIGN PATENT DOCUMENTS

| | | |
|---|---|---|
| WO | 2013/065747 A1 | 5/2013 |
| WO | 2019/245020 A1 | 12/2019 |

OTHER PUBLICATIONS

World Health Organization, "Naming the coronavirus disease (COVID-19) and the virus that causes it", retrieved from https://www.who.int/emergencies/diseases/novel-coronavirus-2019/technical-guidance/naming-the-coronavirus-disease-(covid-2019)-and-the-virus-that-causes-it on Apr. 1, 2021 (Year: 2021).*

Tan et al. ("Rapid and quantitative detection of COVID-19 markers in micro-liter sized samples", bioRxiv preprint doi: https://doi.org/10.1101/2020.04.20.052233, posted Apr. 22, 2020, 17 pages (Year: 2020).*

Yu, J. et al., Detection of Ebola virus envelope using monoclonal and polyclonal antibodies in ELISA, surface plasmon resonance and a quartz crystal microbalance immunosensor, Nov. 2006, Journal of Virological Mehtods, vol. 137, Issue 2 (Year: 2006).*

International Preliminary Report on Patentability issued for international Application No. PCT/JP2021/017121, dated Jun. 7, 2022, 19 pages.

International search report issued for International Application No. PCT/JP2021/017121, dated Aug. 3, 2021, 3 pages.

* cited by examiner

Ag4000ppm+Buffer
(a)　　　　　　　　　(b)
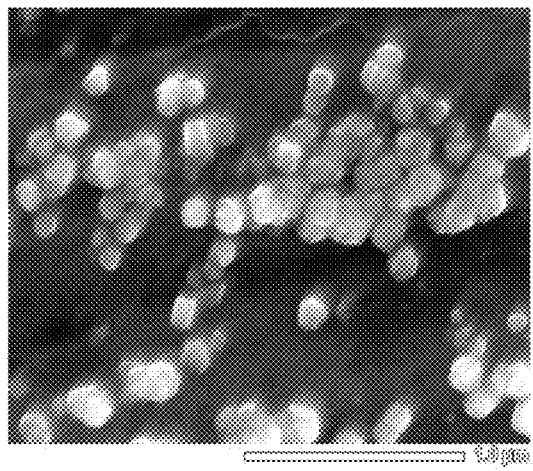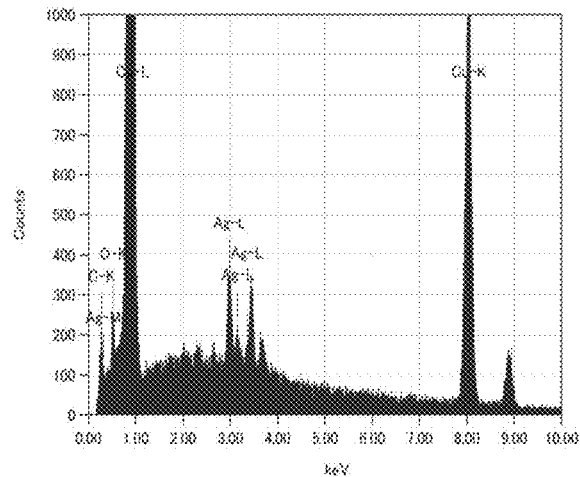
Fig. 9-2
Ag4000ppm plus influenza antibodies(50µg/ml)
(a)　　　　　　　　　(b)
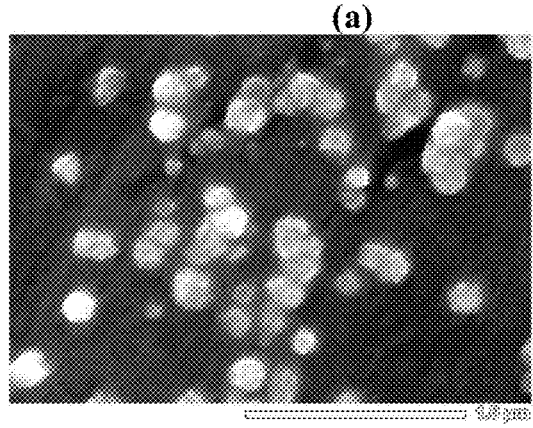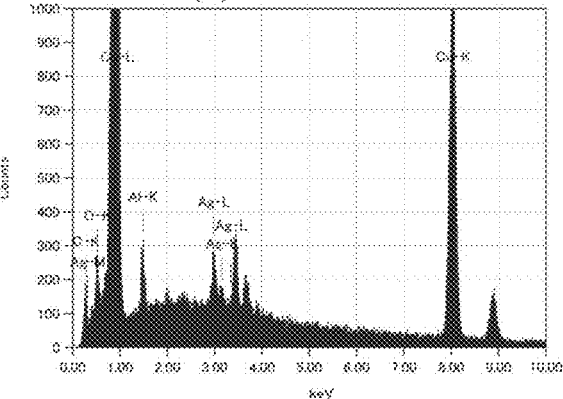
Fig. 9-3

Ag4000ppm plus influenza antibodies(50μg/ml)

(a)          (b)

(a) (b)

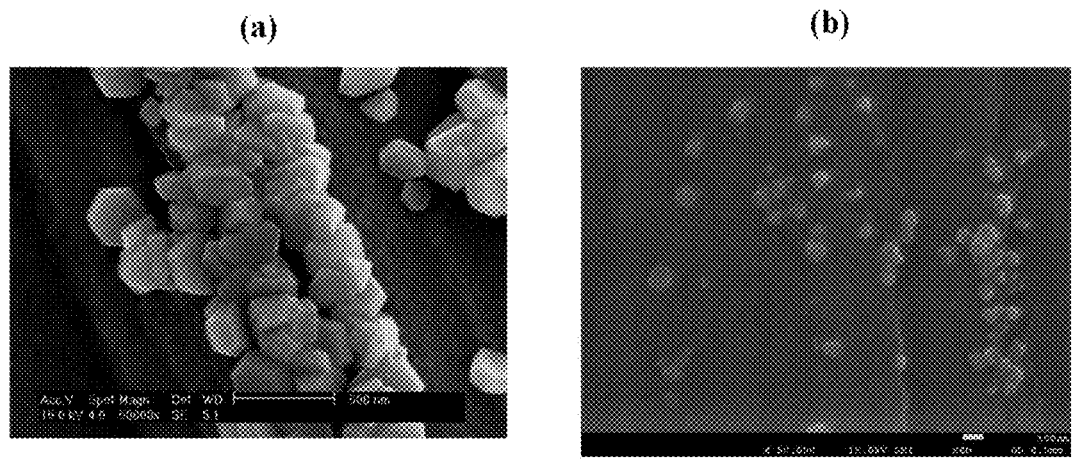

Fig. 20A

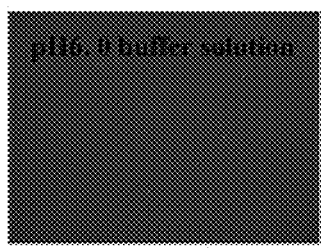 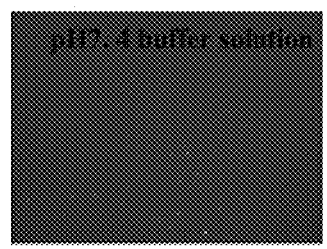 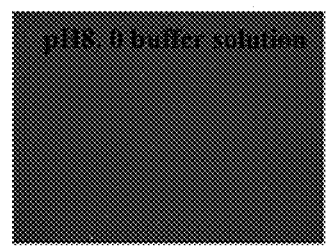

pH6. Fluorescence image obtained by generating quantum crystals with a buffer solution of 0 pH7. Fluorescence images obtained by generating quantum crystals with a buffer solution of 4 pH8. Fluorescence image obtained by generating quantum crystals with a buffer solution of 0

Count and relative values of fluorescent particles obtained by antigen-antibody reaction (sandwich method)

| pH of buffer solution (PBS) added to quantum crystal reagent | Specimen | Number of counts | Relative value |
|---|---|---|---|
| Quantum crystal substrate generated with pH 6.0 buffer | Buffer (Blank) | 3 | 0 |
| | Influenza Virus 10ug/ml | 31 | 28 |
| Quantum crystal substrate generated with pH 7.4 buffer | Buffer (Blank) | 4 | 0 |
| | Influenza Virus 10ug/ml | 64 | 60 |
| Quantum crystal substrate generated with pH 8.0 buffer | Buffer (Blank) | 4 | 0 |
| | Influenza Virus 10ug/ml | 57 | 53 |

Fig. 20B

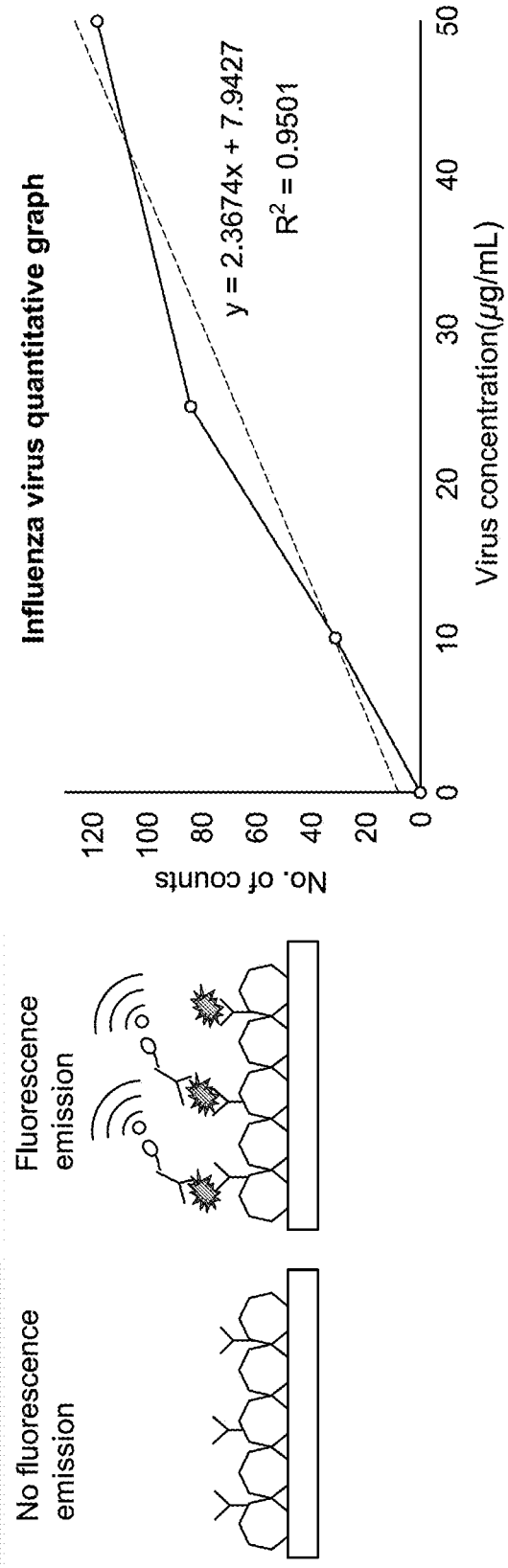
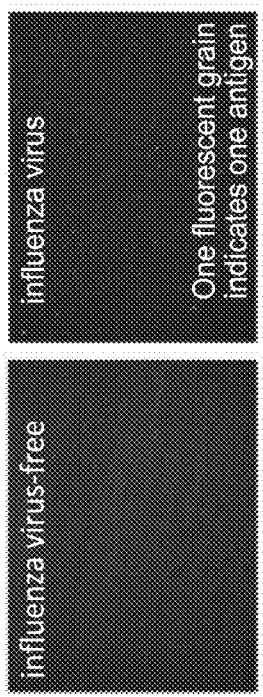
Fig. 23

FLUORESCENCE COUNTING SYSTEM FOR QUANTIFYING VIRUSES OR ANTIBODIES ON AN IMMOBILIZED METAL SUBSTRATE BY USING AN ANTIGEN-ANTIBODY REACTION

CROSS-REFERENCE TO RELATED APPLICATIONS

This application claims the benefit of priority from the Japanese Patent Application No. 2020-80227, filed on Apr. 30, 2020 and Japanese Patent Application No. 2020-86846, May 18, 2020, are hereby incorporated by reference in its entirety.

FIELD OF THE INVENTION

This invention relates to a fluorescence counting system for quantifying viruses or antibodies in an analyte from patients by using an antigen-antibody reaction on an antibody or antigen immobilized or phase solidified substrate, which comprises an unit of phase solidifying or immobilizing viruses or antibodies on a metal substrate, an unit of preparing the labeling liquor and fluorescence labelling viruses and antibodies in the analyte by using an antigen-antibody reaction, a fluorescence excitation unit for viruses and antibodies captured on the solidified substrate and a fluorescence counting detection unit for viruses and antibodies captured on the solidified substrate.

BACKGROUND OF INVENTION

Genetic testing by the PCR is currently the mainstream of viral testing. The PCR is a highly accurate method of sampling mucus and sputum from the back of the nose and throat and examining for proteins such as antigenic viruses contained in the specimen, amplifying the gene contained in the specimen, and examining whether it matches a specific gene sequence. However, this method requires skilled pretreatment techniques and sophisticated inspection equipment. Further, the time required for the inspection is about 6 hours or more. Therefore, a simple and rapid gene-amplification method is desired, and a LAMP (Loop-Mediated Isothermal Amplification) method has been proposed. However, even with some degree of speed, the use of gene amplification is not suitable for in-situ testing where immediate results are required, as is the case with airport testing. Moreover, the PCR method is a qualitative determination of whether it is positive or negative and has a disadvantage of quantitative determination.

Therefore, as a supplementary test to the PCR method, a simple and rapid serological diagnostic method using an immune chromatographic method or an enzymatic antibody method (ELISA) for detecting virus-specific antibodies in serum has been proposed. In the case of common acute viral infections, antibodies in the blood are induced as late as 1 week after onset. Therefore, this type of serodiagnosis requires measuring antibody titers in the blood during the acute and convalescent phases of the disease and comparing antibody transitions. Therefore, it is difficult to adopt a specific antibody detection method in serum as a diagnostic method for acute viral infections that require prompt testing and diagnosis after the onset of symptoms. However, blood samples required for serological diagnosis are relatively straightforward to collect and have a relatively low risk of secondary infection to HCWs at the time of sample collection. In addition, since the detection method of virus-specific antibodies by immune chromatography can perform qualitative analysis by visual judgment, it is possible to quickly and easily perform examination on the outside and on the bet side without requiring any special equipment, and as a result, it is required to introduce the detection method to the clinical site as soon as possible.

Japanese Patent Publication No. 2016-80565 relates a method for measuring Raman spectroscopy of an Ebola virus antigen, and more particularly to a method for rapidly measuring an Ebola virus antigen in a sample by a simplified operation and an Ebola virus antibody immobilized substrate used therefor.

Japanese Patent Application No. 2020-74439 relates to an imprint apparatus and article manufacturing method thereof.

JP 2016-197114 (U.S. Pat. No. 9,139,907 B2) relates to a method for producing a quantum crystal of metal complex containing a quantum dot of metal nanoclusters using an aqueous solution of metal complex and uses thereof.

Currently, in many medical institutions, health professionals have to face patients while they cannot perform screening tests for COVID-19, along with declining medical care delivery caused by COVID-19 infection in inpatients and health professionals (i.e., restrictions on accepting emergency patients, reduced numbers of operations, and reduced outpatient care). To secure the safety of patients and health professionals while maintaining proper medical care delivery, a large-scale screening test that can identify COVID-19 infection accurately and quickly is needed.

However, existing chromatography methods have detection sensitivity limits and PCR methods require lengthy measurement times and a certain level of technique for extracting RNA and using PCR devices. Even the LAMP method requires about 2 hours of testing time for a single specimen, so a diagnostic method that can identify many specimens is being awaited.

However, for COVID-19, it is currently difficult to detect virus-specific antibodies in COVID-19 sera up to 6 days after onset. In addition, it was clarified that the detection rate was only about 20% even in the serum 1 week after the crisis. In addition, the antibody positive rate rises over time, and the IgG antibody in the serum becomes positive in most patients, while the detection rate of the IgM antibody is low, and as a result, there are many cases in which only the IgG antibody becomes positive in the result, when the IgG antibody becomes positive in most patients after 13 days of the crisis. Based on this fact, it is considered that serodiagnosis of COVID-19 using the kits requires the assessment of sera up to 6 days after onset and sera from 13 days after onset by paired sera. In addition, non-specific responses may not be negated by non-gene-amplified antibody-based assays in COVID-19, and results are unreliable to interpret. Therefore, careful consideration of the results of multiple tests and clinical manifestations is required.

Under such circumstances, the examination of viruses requires an accuracy result comparable to that of the PCR method for amplifying genes and a simple and a rapid examination equivalent to that of the immune chromatographic method.

Therefore, the present inventors carried out intensive researches in order to realize (1) an accuracy result comparable to the PCR method and (2) a method capable of performing simple and rapid inspection equivalent to the immune chromatographic method, which are two such problems.

SUMMARY OF INVENTION

An object of the present invention is to develop a system capable of performing simple and rapid inspection equivalent to the above mentioned immune chromatographic method with accuracy comparable to that of the above-mentioned PCR method.

An embodiment relates to a novel fluorescence counting system for quantifying viruses or antibodies in an analyte which comprises an unit of providing an antigen or antibody phase solidified substrate by an aggregation method with quantum crystals, an unit for making a labeling liquor and labeling a virus or an antibody to be measured in the analyte by an antigen-antibody method, an unit of exciting the fluorescently labeled virus or antibody by a surface plasmon excitation method, and an unit of counting fluorescent points in an excited fluorescent screen to quantify the virus or antibody in the analyte.

The present invention relates to a system comprising: a) a metal substrate comprising a plasmon metal complex with a first antigen or a first antibody immobilized on the plasmon metal complex; b) a fluorescence labeling comprised of a labeling fluorescence material configured to label a target forming a labeled target, wherein the labeled target is configured to form an antigen-antibody reaction with the first antigen or the first antibody; c) a fluorescence imaging configured to make a fluorescence image of the labeled target by irradiating an exciting light thereto and observing an excited fluorescence image by a microscope; d) a counting to count fluorescence points and quantify the target; wherein the system is configured to detect the target in an analyte by a fluorescence counting.

One embodiment relates to a system comprising: a) a phase solidified substrate comprising a metal substrate and a coagulated plasmon metal complex with a first antigen or a first antibody immobilized on the coagulated plasmon metal complex; b) a fluorescence labeling unit comprised of a labeling fluorescence material configured to label a target to form a labeled target; c) a fluorescence imaging unit configured to make a fluorescence image of the labeled target by irradiating an exciting light thereto and observing an excited fluorescence image by a microscope; and d) a counting unit to count fluorescence points and quantify the target; wherein the system is configured to detect the target in an analyte by a fluorescence counting.

In one embodiment the phase solidified substrate is configured to be formed by a phase solidifying unit, wherein the phase solidifying unit comprises a buffer solution of the first antigen or the first antibody and a plasmonic metal complex solution, wherein the buffer solution has a pH of about 7 or more, and wherein the metal substrate has an electrode potential more than that of the plasmonic metal complex solution.

In one embodiment, the metal substrate comprises a metal powder

In one embodiment, the plasmonic metal complex solution is in range of 1000 to 5000 ppm.

In one embodiment, the phase solidifying unit is dropped onto the metal substrate to form the coagulated plasmon metal complex, and a device to blow air to stop agglomeration of coagulated plasmon metal complex on the metal substrate.

In one embodiment, the coagulated plasmon metal complex is substantially free of agglomeration of the coagulated plasmon metal complex with each other.

In one embodiment, the target is configured to form an antigen-antibody reaction with the first antigen, or the first antibody immobilized on the coagulated plasmon metal complex.

In one embodiment, the fluorescence labeling unit is dropped on the metal substrate to form the labeled target attached with the coagulated plasmon metal complex.

In one embodiment, the fluorescence imaging unit comprises a light source to irradiate the excitation light having a wavelength range suitable for fluorescence for the labeled target attached with the coagulated plasmon metal complex.

In one embodiment, the counting unit is configured to binarize the fluorescence image to adopt the fluorescence points and quantitatively count the fluorescence points.

In one embodiment, the fluorescence image is binarized with an analysis condition comprises one or more of a brightness, an area, and a circularity of the fluorescence points in the fluorescence image.

In one embodiment, the analysis condition comprises the brightness and the area in the fluorescence image.

In one embodiment, the target comprises an antigen or an antibody.

In one embodiment, the target is labelled by a sandwich method or a direct method or an indirect method.

In one embodiment, the system is configured to detect more than one type of the target.

In one embodiment, the target comprises a virus comprising influenza and/or COVID-19 virus.

In one embodiment, the system comprises a filter for the labeling fluorescence material having a different wave range depending on the target.

One embodiment relates to a method comprising: a) coagulating of a plasmon metal complex solution with a buffer solution of a first antigen or a first antibody; b) forming a phase solidified substrate comprising a metal substrate and a coagulated plasmon metal complex with an immobilized first antigen or an immobilized first antibody; c) forming an antigen-antibody reaction of a target with the immobilized first antigen or the immobilized first antibody on the coagulated plasmon metal complex; d) forming a labeled target attached with the coagulated plasmon metal complex, wherein the labeled target comprises the target and a labeling fluorescent material; d) making a fluorescence image of the labeled target by irradiating an exciting light; e) observing the fluorescence image by a microscope; f) counting fluorescence points; and g) quantifying the target.

One embodiment relates to a method for detecting COVID-19 comprising: a) coagulating of a plasmon metal complex solution with a buffer solution of a first antigen or a first antibody; b) forming a phase solidified substrate comprising a metal substrate and a coagulated plasmon metal complex with an immobilized first antigen or an immobilized first antibody; c) forming an antigen-antibody reaction of a COVID-19 target with the immobilized first antigen or the immobilized first antibody on the coagulated plasmon metal complex; d) forming a labeled COVID-19 target attached with the coagulated plasmon metal complex, wherein the labeled COVID-19 target comprises the COVID-19 target and a labeling fluorescent material; d) making a fluorescence image of the labeled COVID-19 target by irradiating an exciting light; e) observing the fluorescence image by a microscope; f) counting fluorescence points; and g) quantifying the COVID-19 target.

In one embodiment of COVID-19 detection, the phase solidified substrate is configured to be formed by a phase solidifying unit, wherein the phase solidifying unit comprises the buffer solution of the first antigen or the first antibody and the plasmonic metal complex solution, wherein the buffer solution has a pH of about 7 or more, wherein the metal substrate has an electrode potential more than that of the plasmonic metal complex solution.

In one embodiment of COVID-19 detection, the metal substrate comprises a metal powder.

In one embodiment of COVID-19 detection, the plasmonic metal complex solution is in range of 1000 to 5000 ppm.

In one embodiment of COVID-19 detection, the phase solidifying unit is dropped onto the metal substrate and coagulating to form coagulated plasmon metal complex with an immobilized first antigen or an immobilized first antibody, and a device to blow air to stop agglomeration of coagulated plasmon metal complex on the metal substrate.

In one embodiment of COVID-19 detection, the coagulated plasmon metal complex is substantially free of agglomeration of the coagulated plasmon metal complex with each other In one embodiment of COVID-19 detection, a fluorescence labeling unit comprised of the labeling fluorescence material is configured to label the COVID-19 target forming the labeled COVID-19 target, wherein the fluorescence labeling unit is dropped on the metal substrate to form the labeled COVID-19 target attached to the coagulated plasmon metal complex.

In one embodiment of COVID-19 detection, a fluorescence imaging unit is configured to make the fluorescence image, wherein the fluorescence imaging unit comprises a light source for irradiating the excitation light having a wavelength range suitable for fluorescence of a fluorescent substance of the labeled COVID-19 target.

In one embodiment of COVID-19 detection, a fluorescence counting unit is configured to count the fluorescence points.

In one embodiment of COVID-19 detection, the fluorescence counting unit is configured to binarize the fluorescence image to adopt the fluorescence points and quantitively count the fluorescence points.

In one embodiment of COVID-19 detection, the fluorescence image is binarized with an analysis condition comprising one or more of a brightness, an area, and a circularity of the fluorescence points in the fluorescence image.

In one embodiment of COVID-19 detection, the analysis condition comprises the brightness and the area in the fluorescence image.

In one embodiment of COVID-19 detection, the COVID-19 target comprises an antigen or an antibody.

In one embodiment of COVID-19 detection, the method is compatible to detect a second target with the COVID-19 target.

In one embodiment of COVID-19 detection, the second target comprises a virus comprising influenza.

In one embodiment of COVID-19 detection, the COVID-19 target and/or the second target is labelled by a sandwich method or a direct method or an indirect method.

In one embodiment of COVID-19 detection, the labeling fluorescence material having a different wave range depending on the COVID-19 target and the second target.

One embodiment relates to a system for quantifying an antigen or an antibody to be measured in an analyte by fluorescence counting, comprising 1) a phase solidifying unit for making a phase solidified substrate on which an antibody or an antigen solidified on a metal substrate with coagulation of plasmon metal complex quantum crystals; 2) a fluorescence labeling unit for making a labeling liquor made of a labeling fluorescence material with an antibody or an antigen to be measured in an analyte and dropping the labeling liquor on the phase solidified substrate to make a measuring chip by means of an antigen-antibody reaction; 3) a fluorescence imaging unit of making the fluorescence image of the labeled antibody or antigen on the measuring chip as the measuring target by irradiating an exciting light thereto and observing the excited fluorescence image by a fluorescence microscope; 4) a counting unit of the number of fluorescence points of a certain selected region in the excited fluorescence image, and 5) a conveying tool for the substrate from the first position for the first phase solidifying unit to the final position for the final counting unit.

In one embodiment, the phase solidifying unit comprises a mixer for making a phase solidifying liquor by mixing a predetermined amount of a buffer solution of the inactivated antigen or the antibody with a predetermined amount of an aqueous plasmonic metal complex solution, a metal substrate having a noble electrode potential more than that of the plasmonic metal complex, a compression syringe for dropping a quantitative amount of the phase solidifying liquor onto the metal substrate, and an air blowing means for stopping aggregation of the aqueous plasmon metal complex solution on the metal substrate by removing the phase solidifying liquor on the metal substrate under a predetermined time elapse.

In one embodiment, the fluorescence labeling unit comprises a mixer for making the labeling liquor containing the antigen or the antibody to be labeled in the analyte, a compression syringe for dropping a predetermined amount of the labeling liquor on the phase solidified substrate to combine the labeled antigen or antibody with the antibody or the antigen solidified on the substrate, and a washing and drying means for washing off an unbound labeling liquor from the substrate by a washer and an air blower.

In one embodiment, the fluorescence imaging unit comprises a light source for irradiating an excitation light having a wavelength range suitable for the fluorescence substance for labeling the virus or the antibody on the measuring chip for exciting fluorescence of the labeled fluorescent substance with the quantum crystal of the plasmon metal by the excitation light, and a fluorescence microscope for observing the fluorescence image on the measurement chip by autofocusing the fluorescence image.

In one embodiment, fluorescence counting means a means for selecting at least one region in the fluorescence image, a means for binarizing fluorescence points of the selected region to adopt a fluorescence point or points equal to or larger than a predetermined threshold value, and a quantitative means for counting number of the fluorescence points.

In one embodiment, as the phase solidifying unit uses the phase solidifying liquor in a substantially neutral pH range formed of the plasmonic metal complex aqueous solution of 1000 to 5000 ppm, preferably 2000 to 4000 ppm, and a neutral pH or higher buffer containing a virus inactivated or an antibody thereof to be solidified on the metal substrate, in order to produce an antibody or antigen solidified substrate in which quantum crystals of the plasmon metal complex in a measurement region of a substrate are substantially dispersed and aggregated in order to make a suitable substrate to be combined the antigen or antibody to be measured for detection.

In one embodiment, the fluorescence point in the fluorescence image is binarized with an analysis condition selected from the brightness, the area, and the circularity to adopt or select the suitable fluorescence points among all of them in the fluorescence image.

One embodiment relates to a method for quantification of an antigen or an antibody to be measured in an analyte by using the antigen-antibody reaction, comprising the steps of 1) solidifying an antibody or an antigen on a metal substrate to make a phase solidified substrate; 2) making a fluorescence labeling liquor by mixing an antibody or an antigen to be measured with a fluorescence substance and fluorescence labeling the antigen or antibody to be measured with the labeling liquor by the antigen-antibody reaction; 3) making a fluorescence image of the labelled antigen or antibody and observing the fluorescence image by a fluorescence microscope; 4) counting the number of fluorescence points of a certain selected region in the observed fluorescence image, wherein the phase solidifying liquor is a mixture made of 1000 to 5000 ppm, preferably 2000 to 4000 ppm of a plasmonic metal complex aqueous solution and a substantially neutral buffer solution containing an inactivated virus or an antibody to be solidified on the metal substrate.

In one embodiment, the measurement target in the analyte is the inactivated virus or the antibody thereof in an analyte from a patient, and the concentration in the analyte is 10 µg/ml or more.

In one embodiment, the fluorescent labeling is carried out based on one selected from the group consisting of a sandwich method 1) wherein the antigen is sandwiched between an antibody on the phase solidified substrate and an antibody to be labeled in the labeling liquar, a direct method 2) wherein a virus antigen or antibody is labeled directly by a labeled antibody or labeled antigen and an indirect method 3) wherein a virus antigen or antibody is labeled by an antibody and a secondary antibody.

In one embodiment, surface plasmon excitation of the fluorescence is carried out according to irradiation of excitation light on a quantum crystal solidified together with the antigen or antibody on the phase solidified substrate.

In one embodiment, the fluorescence counting step is carried out on one or more fields of a measurement image through a fluorescence microscope, and the counting of fluorescence points equal to or greater than a predetermined luminance value is carried out after binarizing of the fluorescence points.

One embodiment relates to a method for identifying and quantifying two or more kinds of antigens or antibodies to be measured in an analyte, comprising a step of providing a phase solidified substrate by mixing together two or more kinds of an inactivated antigen or antibody with an aqueous plasmon metal complex solution to make a phase solidifying liquor and dropping the phase solidifying liquor on a metal substrate to aggregate the antigen or antibody to be solidified with quantum crystals of the plasmon metal complex, a step of providing a labeling liquor containing the antigen or antibody to be measured in the analyte, a step of fluorescent labeling by dropping the labeling liquor on the antibody or antigen solidified substrate and labeling the antigen or antibody with two or more kinds of fluorescence substances by an antigen-antibody reaction, a step of fluorescence excitation and step of observing one of fluorescence images for one of the antigens or antibody by selecting and irradiating one or more exciting light having a wavelength of the fluorescence corresponding to each of the one or more kinds of fluorescence for labeling the antigen or antibody to be measured, and a fluorescence counting step of counting the number of fluorescence points of each of color tones in the observed fluorescence image.

In one embodiment, simultaneously discriminating and quantifying two or more antigens or antibodies is possible.

In one embodiment, a mixture of a plasmonic metal complex aqueous solution of 1000 ppm to 5000 ppm, preferably 2000 to 4000 ppm, with a neutral or higher buffer containing an inactivated virus or an antibody thereof is used as the phase solidifying liquor for solidifying the antibody or antigen, and the quantum crystals are substantially dispersed and aggregated for making good measurement regions of the substrate.

In one embodiment, two or more distinct viruses are influenza and Covid-19, the different fluorescent wavelengths of the labeled antibodies being used for detecting either one of two viruses.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 9-1 shows a 25000× SEM images of various quantum crystal solid-phased substrates showing the respective SEM images of (a) a solid-phased substrate with 2000 ppm of Ag reagent (aqueous silver thiosulfate solution) and phosphate buffer solution; (b) a solid-phased substrate with 2000 ppm of Ag reagent and phosphate buffer solution containing influenza antibody (50 µg/ml); and (c) a solid-phased substrate with 2000 ppm of Ag reagent and phosphate buffer solution containing influenza virus (50 µg/ml).

FIG. 9-2 shows a graph showing the quantum crystal state and component analysis results of each solid-phase substrate. It is a SEM image and a component analysis graph of a solid-phase substrate using 4000 ppm of Ag reagent (aqueous silver thiosulfate) and phosphate buffer solution.

FIG. 9-3 shows a SEM images and component analysis graphs of solid-phased substrates using 4000 ppm Ag reagent and phosphate buffer containing influenza antibody (50 µg/ml).

FIG. 9-4 shows a SEM images and component analysis graphs of solid-phased substrates using 4000 ppm Ag reagent and phosphate buffer containing influenza virus (50 µg/ml).

collection section 20 containing the sample is inserted into the depth of the tube 10. Since the back of the tube is processed to be small, the sample collection part is compressed, and the sample is dispersed in the inactive liquid. In the fifth step, only the sampling portion is left in the tube, and the other portion is removed. In the sixth step, the inactivated specimen is kept in the tube.

Figure 19A:
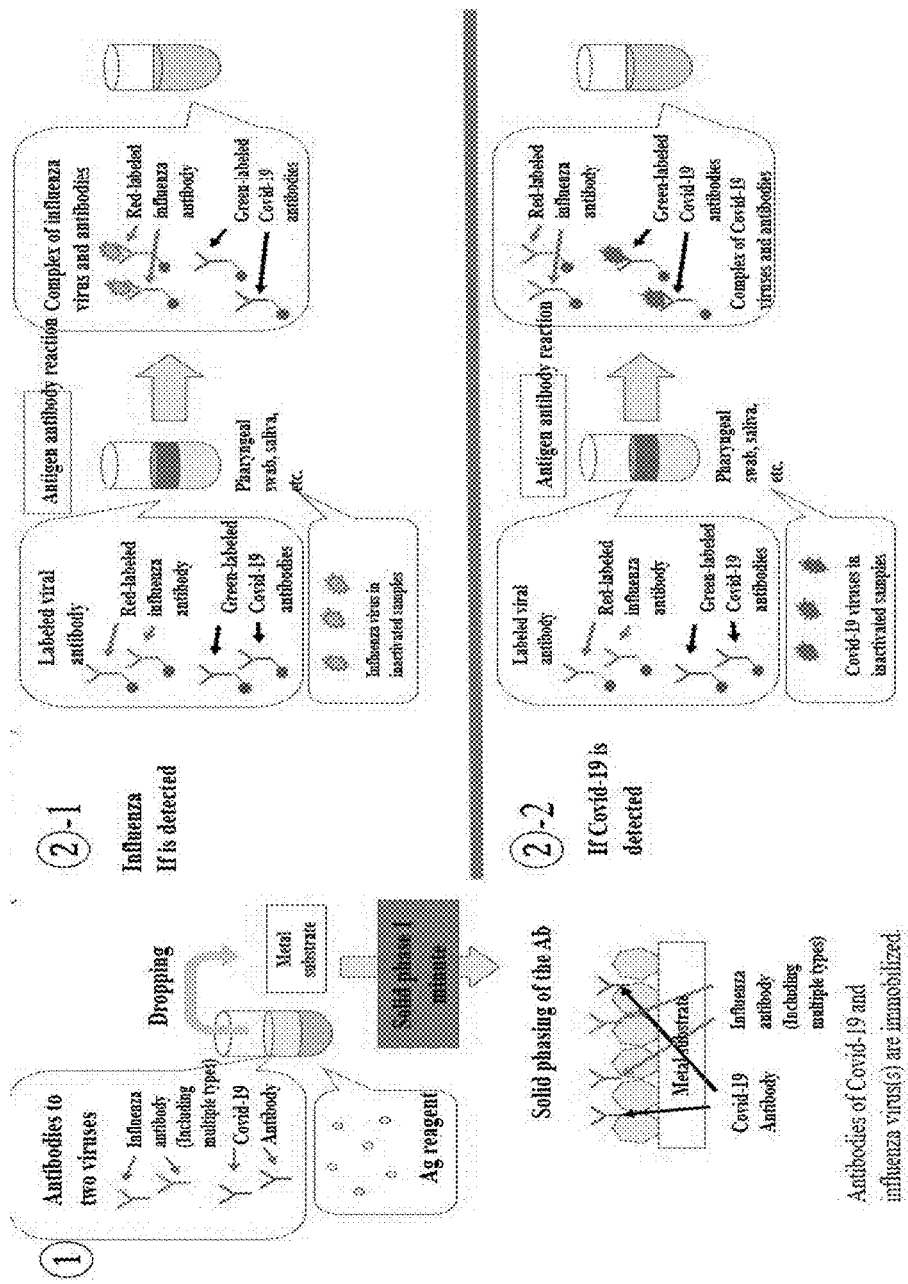

FIG. 19A shows a Detection of Two Viruses using sandwich method of the present invention, it is a schematic view comprising of (1) a solid phase process and (2) a preparation process for fluorescent labeling when detecting 2 kinds of viruses.

Figure 19B:
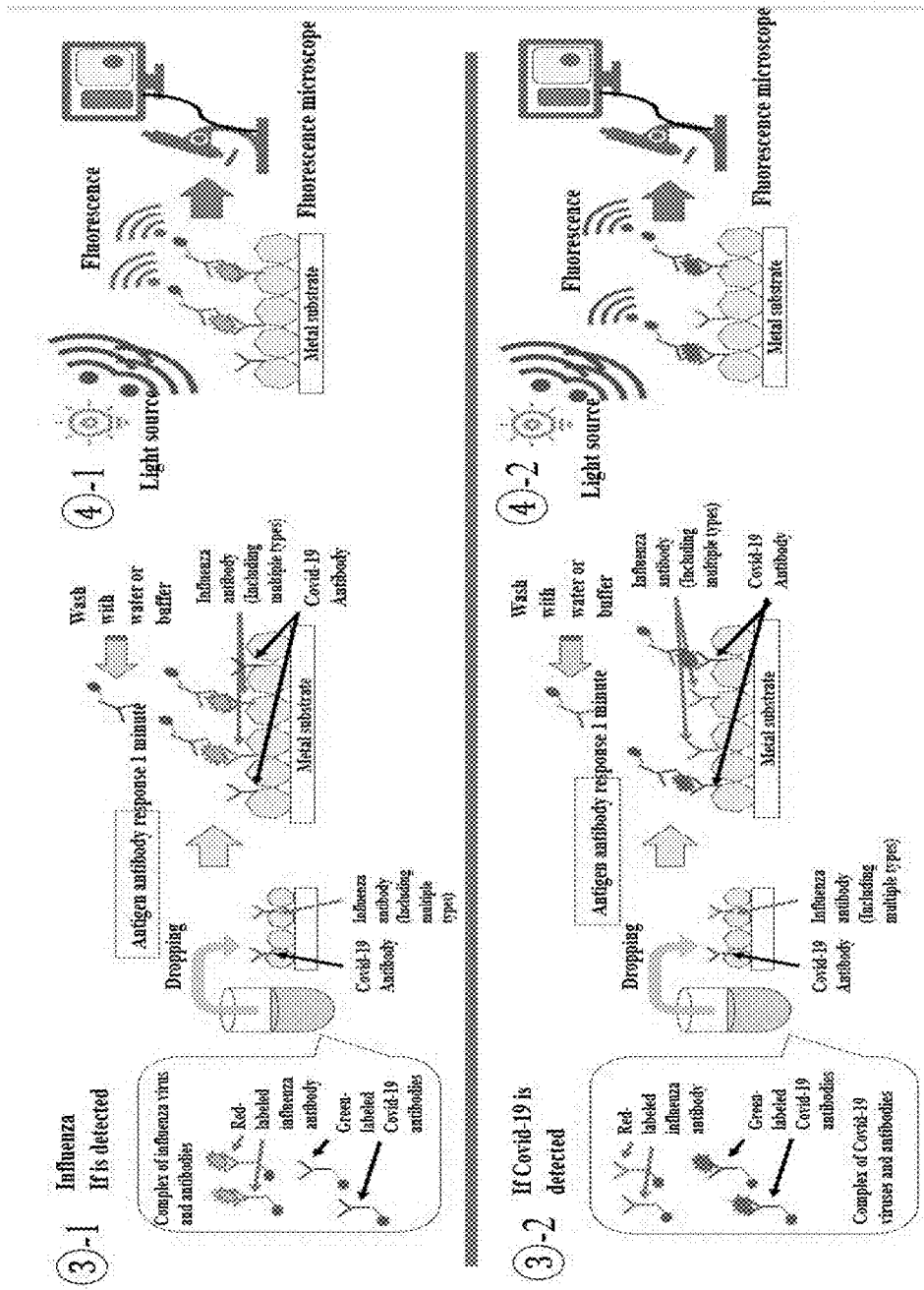

FIG. 19B shows a sandwich method of the present invention, it is a schematic diagram showing (3) a fluorescence labeling process and (4) a surface plasmon excitation process and a fluorescence counting process when detecting 2 kinds of viruses.

FIG. 20A shows a comparative SEM images showing the pH effect of the aggregated form of quantum crystals when the Ag-reagent of the present invention is used, (a) is an SEM image showing the aggregated form in the case of pH6 (50000× magnification), (b) is an SEM image showing the aggregated form in the case of pH6 of pH74 (50000× magnification).

FIG. 20B shows a table showing the comparative count number showing the pH influence of the aggregated form of quantum crystals when using the Ag reagent of the present invention.

Figure 21:
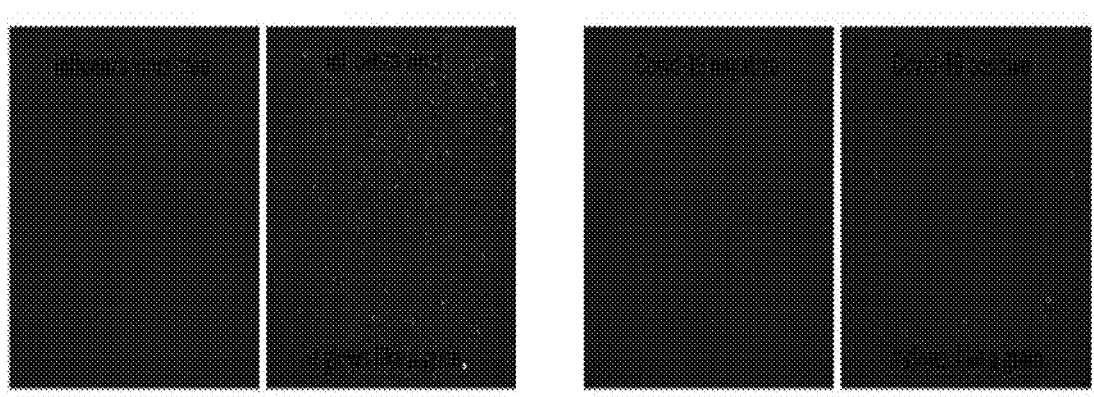

FIG. 21 shows detection of corona virus (COVID-19) and influenza virus by the present invention.

Figure 22:
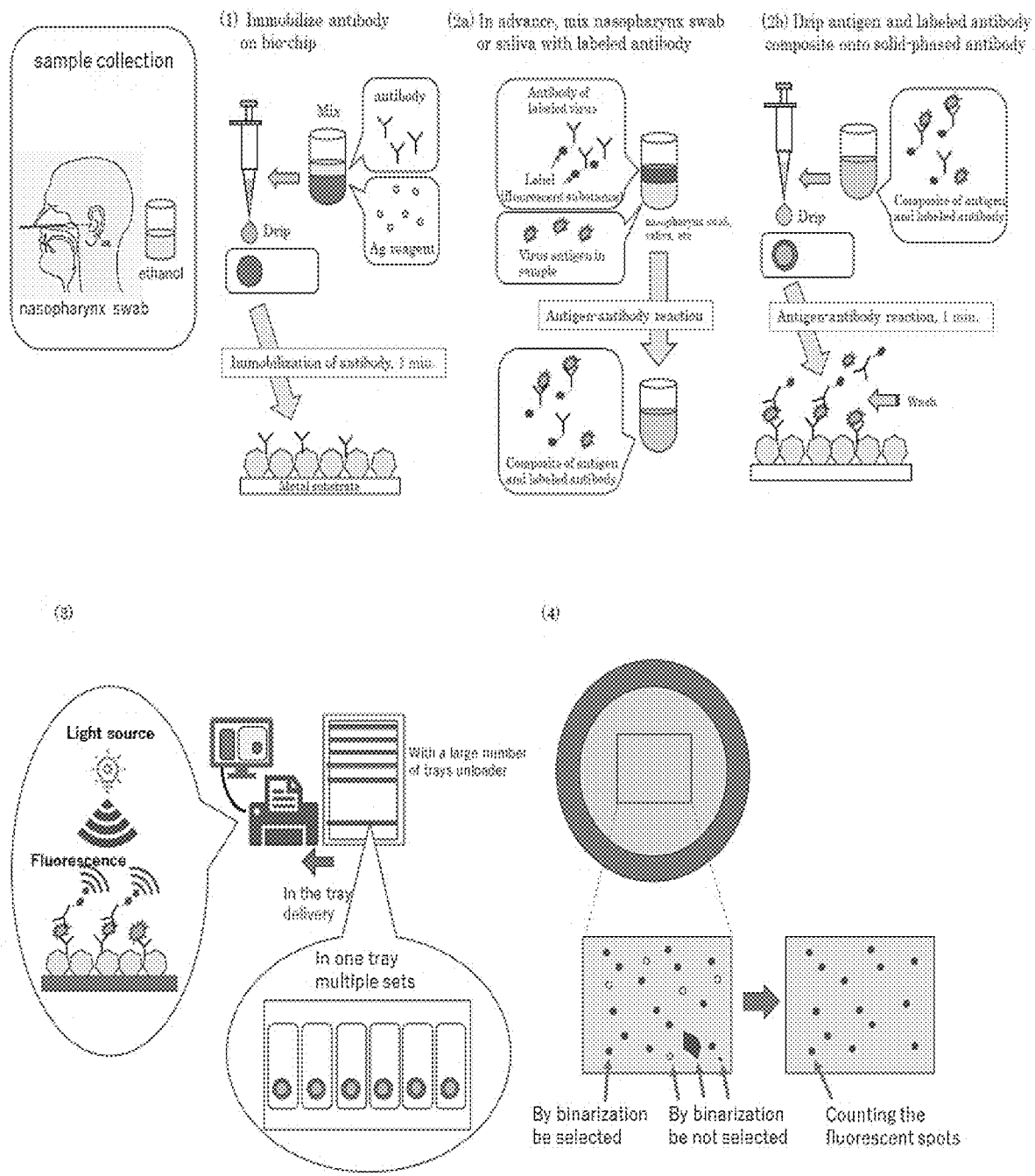

FIG. 22 shows virus detection protocol according to present invention. By mixing the collected samples with ethanol, they can be inactivated, reducing the risk of infection for healthcare workers. Inactivated samples can be safely moved and transported. In step (1) Ag reagent, mixed with antibody, is dripped onto the metal substrate. Antibody is immobilized on quantum crystal formed on the metal substrate. In step 2a, Labelled virus antibody and the sample are mixed. Due to antigen-antibody reaction, the virus antigen contained in the sample and the labeled antibody form a composite. In step 2b, the composite of labeled antibody and antibody is dripped onto a measurement chip. Antigen-antibody reaction combines the composite with antibody on the substrate. Uncombined composite and antibody, etc. are washed away with buffer solution, etc. In step 3, Fluorescence-excited images and chips are set in a tray, with the binning process to increase sensitivity and auto-focusing for automatic measurement of fluorescent Images. In step 4 of Counting automation, Selection of fluorescence points in fluorescence images (error resolution) by binarization with analysis conditions (brightness threshold, area value, circularity, etc.) and counting of fluorescence spots binarized.

FIG. 23 shows visual and quantitative detection of influenza virus. Quantitative measurement by counting the number of fluorescence. Fluorescent virus identification by observing fluorescent images.

Figure 24:
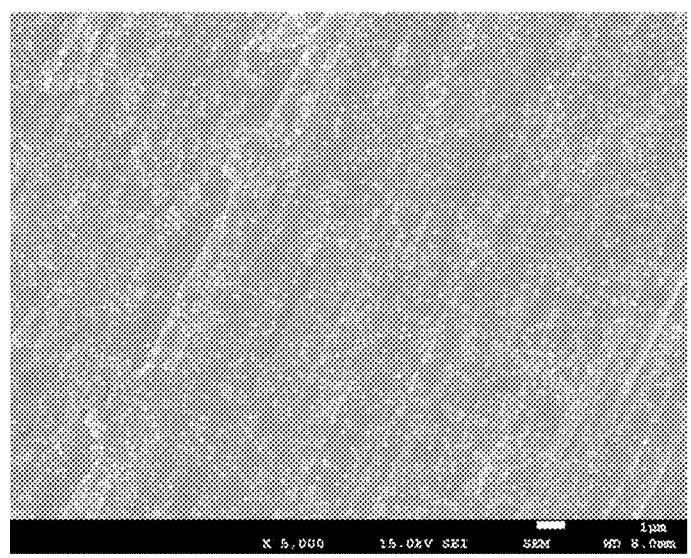

FIG. 24 shows SEM photograph of the Quantum Crystal.

DETAILED DESCRIPTION

Definitions and General Techniques

For simplicity and clarity of illustration, the drawing figures illustrate the general manner of construction, and descriptions and details of well-known features and techniques may be omitted to avoid unnecessarily obscuring the present disclosure. Additionally, elements in the drawing figures are not necessarily drawn to scale. For example, the dimensions of some of the elements in the figures may be exaggerated relative to other elements to help improve understanding of embodiments of the present disclosure. The same reference numerals in different figures denote the same elements.

The terms "first," "second," "third," "fourth," and the like in the description and in the claims, if any, are used for distinguishing between similar elements and not necessarily for describing a particular sequential or chronological order. It is to be understood that the terms so used are interchangeable under appropriate circumstances such that the embodiments described herein are, for example, capable of operation in sequences other than those illustrated or otherwise described herein. Furthermore, the terms "include," and "have," and any variations thereof, are intended to cover a non-exclusive inclusion, such that a process, method, system, article, device, or apparatus that comprises a list of elements is not necessarily limited to those elements, but may include other elements not expressly listed or inherent to such process, method, system, article, device, or apparatus.

The terms "left," "right," "front," "back," "top," "bottom," "over," "under," and the like in the description and in the claims, if any, are used for descriptive purposes and not necessarily for describing permanent relative positions. It is to be understood that the terms so used are interchangeable under appropriate circumstances such that the embodiments of the apparatus, methods, and/or articles of manufacture described herein are, for example, capable of operation in other orientations than those illustrated or otherwise described herein.

No element, act, or instruction used herein should be construed as critical or essential unless explicitly described as such. Also, as used herein, the articles "a" and "an" are intended to include items, and may be used interchangeably with "one or more." Furthermore, as used herein, the term "set" is intended to include items (e.g., related items, unrelated items, a combination of related items, and unrelated items, etc.), and may be used interchangeably with "one or more." Where only one item is intended, the term "one" or similar language is used. Also, as used herein, the terms "has," "have," "having," or the like are intended to be open-ended terms. Further, the phrase "based on" is intended to mean "based, at least in part, on" unless explicitly stated otherwise.

As defined herein, two or more elements are "integral" if they are comprised of the same piece of material. As defined herein, two or more elements are "non-integral" if each is comprised of a different piece of material.

As defined herein, "real-time" can, in some embodiments, be defined with respect to operations carried out as soon as practically possible upon occurrence of a triggering event. A triggering event can include receipt of data necessary to execute a task or to otherwise process information. Because of delays inherent in transmission and/or in computing speeds, the term "real time" encompasses operations that occur in "near" real time or somewhat delayed from a triggering event. In a number of embodiments, "real time" can mean real time less a time delay for processing (e.g., determining) and/or transmitting data. The particular time delay can vary depending on the type and/or amount of the data, the processing speeds of the hardware, the transmission capability of the communication hardware, the transmission distance, etc. However, in many embodiments, the time delay can be less than approximately one second, two seconds, five seconds, or ten seconds.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

As defined herein, "approximately" or "about" can, in some embodiments, mean within plus or minus ten percent of the stated value. In other embodiments, "approximately" or "about" can mean within plus or minus five percent of the stated value. In further embodiments, "approximately" or "about" can mean within plus or minus three percent of the stated value. In yet other embodiments, "approximately" or "about" can mean within plus or minus one percent of the stated value.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, health monitoring described herein are those well-known and commonly used in the art.

The methods and techniques of the present invention are generally performed according to conventional methods well known in the art and as described in various general and more specific references that are cited and discussed throughout the present specification unless otherwise indicated. The nomenclatures used in connection with, and the procedures and techniques of embodiments herein, and other related fields described herein are those well-known and commonly used in the art.

Fluorescent antibody is a method for examining the distribution of antigens in tissues and cells using antibodies that specifically recognize the antigen. In this method, by sequentially using a primary antibody and a secondary antibody, the distribution of the primary antibody in the tissue, the cell, that is, the distribution of the antigen recognized by the primary antibody is observed as the distribution of the fluorescently labeled secondary antibody. However, to utilize this method outside the tissue and cell system, the virus in the sample taken from the patient must be solidified or immobilized outside the tissue and cell system. In addition, the inventors of the present invention have learned that even if a virus can be converted into a solid phase as a sample over a period of time, a pseudo-sample tends to exist between the samples converted into a solid phase, and this causes a non-specific reaction (a phenomenon in which some biological components other than the object of measurement cause an abnormal reaction with components such as a measurement reagent and an additive of a blood collection tube, and shows a measurement value far apart from the pathological state), thereby deteriorating the measurement accuracy.

The present inventors have conducted extensive research. As a result, it was found that, when a method of aggregating quantum crystals of a plasmonic metal complex is utilized, a viral antigen is simultaneously aggregated and solidified on a metal substrate during aggregation of the quantum crystals. Then, it was found that when the solid phased virus was fluorescently labeled, the fluorescence of the virus appeared in the form of dots or spots in the fluorescence image by the surface plasmon enhancement action of the plasmon metal complex aggregated at the same time, and the number of viruses could be counted as the dot-like fluorescence number (hereinafter referred to as fluorescence counting method). In addition, it has been found that, in such a fluorescence counting method, a non-specific reaction which is likely to occur by a fluorescent antibody method can be eliminated or alleviated, and as a result, accuracy is remarkably improved as shown in FIG. 20 B.

The term "Coagulation" as used herein is defined as a collection of plasmonic metal complex to form a particle. Coagulation is caused by plasmon metal complex solution mixed with a buffer having a pH of 7 or more. The term coagulation or aggregation is interchangeably used throughout the specification.

The term "agglomeration" as used herein is defined as a jumbled collection of particles. In agglomeration, these particles containing coagulated plasmonic metal complex come together to form lumps. As shown in FIG. 20A(a), the particles are agglomerated whereas in the FIG. 20 A(b), the particles containing coagulated plasmonic metal complex are substantially free of agglomeration.

The term "substantially free" is defined as less than 50% of the coagulated plasmonic metal complex are agglomerated to form a lump. In some embodiment, the agglomeration may be less than less than 60% of the coagulated plasmonic metal complex. In another embodiment, the agglomeration may be less than less than 70% of the coagulated plasmonic metal complex. Yet in another embodiment, the agglomeration may be less than less than 80% of the coagulated plasmonic metal complex.

In an embodiment, the present invention provides a novel fluorescence counting system for quantifying an analyte (virus or an antibody produced by a virus in an immune function in a human or animal body) in a fluorescence image by a fluorescence spot or particle.

1) Firstly, a solid-phase making process can be carried out to provide a solidified substrate in which inactivated viruses or antibodies thereof are aggregated on a metal substrate together with plasmon metal complexes at an electrode potential difference and immobilized on the metal substrate together with metal complex quantum crystals, 2) Secondly, by using an antigen-antibody reaction, the virus or antibody to be measured in an analyte can be captured with the immobilized virus or antibody on the solidified substrate and can be fluorescently labeled by an antigen antibody reaction, 3) Thirdly, the fluorescently labeled viruses or the antibody can be excited by the surface plasmon excitation action of quantum crystals by irradiation of the exciting light, 4) Fourthly, a fluorescence counting process can be carried out by a system comprising a unit of binarizing the fluorescent spots or grains in the obtained fluorescent image to select the good fluorescent spots or grains having a predetermined threshold value or more and then counting the fluorescent spots or grains.

According to the present invention, in the first solid phase process, a viral antigen or an antibody thereof is solidified. In the solidification process, quantum crystals (plasmon metal complex crystals of 50 to 150 nm; hereinafter the same) and antigens or antibodies (usually diluted with a buffer solution, hereinafter the same) are often solidified (aggregated on a metal substrate by an electrode potential difference from the metal substrate by a quantum crystal aggregation method).

In an embodiment, labeling is performed by mixing a virus antigen (usually inactivated with ethanol or the like and diluted with a buffer solution in some cases, hereinafter, the same) and a labeled antibody (labeled with a phosphor and usually diluted with a buffer solution, hereinafter, the same) in the second fluorescent labeling process. This fluorescent labeling process is called as a sandwich method in the typical antigen-antibody reaction because an antigen is sandwiched between an antibody to be dropped onto a solid-phase substrate and a labeled antibody.

In another embodiment, the fluorescent labeling process can be carried out on the basis of a direct method in which a viral antigen is solidified and then labeled with a labeled antibody, or an antibody is solidified and then labeled with a labeled antigen (including a fluorescent material in which a portion of an antigen is labeled, hereinafter the same)

In another embodiment, the fluorescent labeling process can be carried out according to an indirect method in which the viral antigen is solidified and then the antibody and the secondary antibody are sequentially bound, or an antibody is solidified and then the viral antigen is bound and then finally the antibody and the secondary antibody are sequentially bound to be labeled.

In an embodiment, the present invention enhances fluorescence by efficiently subjecting a virus captured by an antigen-antibody reaction or a labeled fluorescent molecule associated with an antibody thereof to surface plasmon excitation by a plasmonic metal complex which is simultaneously solidified, an analyte such as a virus can be quantified by counting the number of fluorescent puncta or spot.

Figure 16:
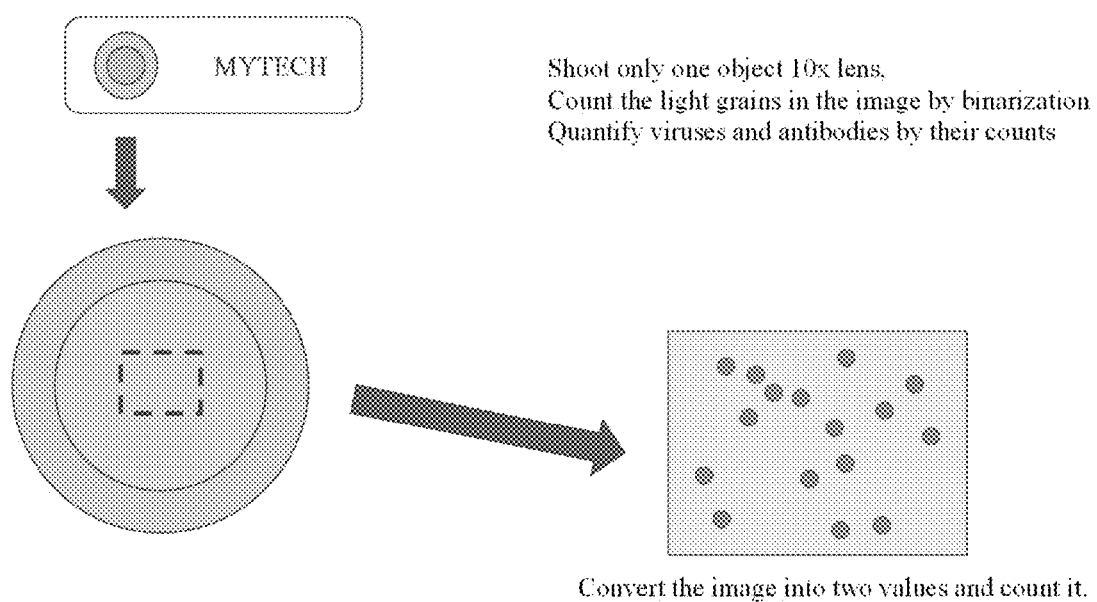

In an embodiment, the present invention has a feature in which a fluorescence signal appears in a dotted state or a granular state in a fluorescence image observed by a fluorescence microscope. Therefore, when the dot-like signal can be binarized to count fluorescent puncta or grains equal to or larger than a constant threshold value, it correlates with the number of viruses and the number of antibodies, so that accurate quantification of viruses and antibodies can be performed as shown in FIG. 16.

In an embodiment, the pseudo-nature of the fluorescence signal due to the nonspecific reaction can be also eliminated without the necessary for microchannels compared to the conventional solid-phase substrate using the gold film electrode surface.

The difference between the present invention fluorescence counting method and the conventional fluorescence spectroscopy (SPFS) method may be attributed to the fact that the latter is solidified by an organic molecule on a gold thin film, whereas the present invention is solidified by aggregation of plasmonic metal complex quantum crystals.

Furthermore, solid-phase techniques for analytes in conventional methods are cumbersome. In the conventional method, a microchannel is applied as a highly efficient reaction promoting technique. However, the use of this microchannel makes the measurement complicated and difficult. In the present invention, it is possible to easily and quickly achieve the solid phase required for the measurement of virus by aggregation of quantum crystals of plasmonic metal complexes. That is, it is easy to solidify antibodies or antigens in a reactive field, and it is possible to provide a novel way capable of fluorescence spectroscopy (SPFS) of highly reproducible surface plasmon excitation enhancement even without using a micro channel. Comparing the present inventive fluorescence dot counting method with the conventional fluorescence intensity quantifying method, the former method is better than the latter method in that the fluorescence counting has higher accuracy and more simple process.

We have also tested to detect Ebola virus by using Raman method on the antibody phase solidified substrate as shown in the Patent literature 1 (Japan Patent Publication No. 2016-80565), but we have failed to detect the Ebola virus because Ebola virus could not be caught in a good state on the substrate for by agglomeration of the quantum crystal without a buffer solution and we had no result by Raman scattering method.

(Quantification Differences Compared with the PCR)

This inventive fluorescence counting method is also a valuable quantitative test that allows us to know the current status of the onset, progression, and cure of the condition, while the qualitative PCR method is only available to the detection whether the virus condition is positive or negative. In addition, different from the immunochromatographic method for examining immune antibodies, it is possible to quickly and accurately determine whether or not infection is caused by quantitation of the viral load by fluorescence counting.

(Significance of Fluorescence Count)

Figure 6:
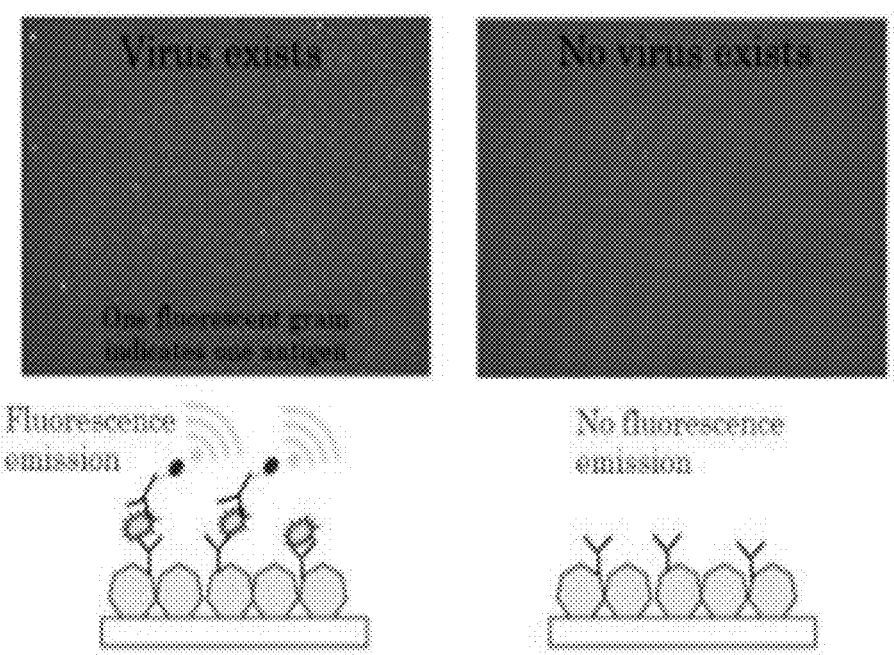
FIG. 6 shows measurement image of Influenza Virus. The fluorescence image of the present invention, a fluorescence image in the presence of an influenza virus (a) and a fluorescence image in the absence of an influenza virus (b) are shown. Instruments used were: Keyence fluorescence microscopy BZ-X710, light source: metal halide lamp 80 W, fluorescence filter: BZ-X filter GFP (525±25), and analysis software: BZ-X Analyzer.

The present fluorescence counting method of the present invention is excellent in quantification in detection of virus and antibody. For example, when the influenza virus is subjected to fluorescence spectroscopy by an antigen-antibody reaction (for example, the sandwich method), the measured image emits a large number of fluorescent spots in a granular form when there are viruses, and this granular fluorescent spot is the fluorescence of the labeled antibody in which the viruses are sandwiched and correlates with the number of viruses when the fluorescent particles above a certain threshold are counted (FIG. 6(*a*)), while it is newly found that a large number of granular fluorescent spots do not appear when there is no virus (FIG. 6(*b*)).

In an embodiment, the plasmon metal complex in the solution coagulates as quantum crystals of the metal complex on the metal substrate having the electrode potential in the vicinity of the reduction potential (hereinafter referred to as a quantum crystal coagulation method) by the selection of the electrode potential, and when the antigen or antibody coexists in the solution, the antigen or antibody coagulates on the substrate or particle together with the metal complex to form a solidified plasmon reaction field. Therefore, different from the conventional plasmon metal thin film, the present inventive metal complex crystals of about 100 nm are regularly arrayed, and antigens or antibodies are physically or chemically solidified between the quantum crystals at regular intervals, so that a structure similar to that of forming a micro-channel is obtained, and surface plasmon excitation can be enhanced.

In an embodiment, of present invention of fluorescence spectroscopy (SPFS) methods of surface plasmon excitation enhancement, it is useful to count the number of puncta or spot fluorescence observed by fluorescence microscopy to analyze the disease by quantitation of viruses, that is, the disease can be diagnosed according to not only with presence of viruses or without viruses, but also the amount of disease can be diagnosed with the number of the viruses.

(Effect of the pH of Quantum Crystal Solidification)

In an embodiment, the preparation of the solid-phase substrate (quantum crystal) is caused by potentiometric aggregation of the quantum crystal to the metal substrate, the pH at the time of mixing the Ag reagent with the antibody buffer or the antigen buffer influences the aggregation phenomenon.

The relationship between the pH influence of this quantum crystal aggregation and the quantification in fluorescence images of the aggregation state is as follows:

An aqueous solution of silver thiosulfate of around 2000 ppm is used as an Ag-reagent for producing quantum crystals but is usually adjusted to a degree of pH 6. On the other hand, Ag reagents of pH 6 is mixed with buffer to be adjusted to pH 7.4 and 8.0, the count number of the fluorescent spots at pH 6.0 becomes small, while the count number of pH 7.4 and 8.0 become large.

This is because the pH of the quantum crystal reagent is about 6 without any buffer or when a buffer of pH6.0 is added, it becomes very aggregated state as shown in SEM image of FIG. 20A(a), while when the pH is adjusted to 7.4 and 8.0 by addition of the buffer solution, the quantum crystal becomes dispersed and fine crystals as shown in SEM image of FIG. 20A(b).

In other words, when quantum crystals are formed on a substrate at a pH6 without adding anything, three-dimensional crystals stacked in hexagonal structures are formed on the substrate (FIG. 20A (a)). However, when the buffer solution of pH7.4 and the antibodies were mixed into the quantum crystal reagents to bring the pH of the solution to about pH7 or more and to generate quantum crystals on the substrate, crystals on fine grains of the crystals were dispersed on the substrate (FIG. 20A (b)). From the SEM image of this quantum crystal, it was found that the pH of the solution was important in producing the quantum crystal for the solid-phased substrate.

In an embodiment, the present invention provides a novel analyte-immobilized fluorescence counting method which is excellent in image retrieval observed by fluorescence microscopy in a fluorescence spectroscopy (SPFS) of surface plasmon-excited enhancement, and is capable of analyzing a disease by counting the number of fluorescent particles in a fluorescence image, the presence or absence of viruses, and the number of counts.

In an embodiment, the methods of the present invention is a solid-phase substrate in which a plasmon metal complex is solidified together with an antibody by using a quantum crystal aggregation to have a surface plasmon excitation effect, and fluorescence of the composite labeled by surface plasmon excitation is observable as granular fluorescence in a fluorescence image thereof by irradiation of excitation light, and the number of granular fluorescence is detectable as a virus amount.

The quantum crystal aggregation method is a method in which a plasmon metal complex in a solution aggregates as a quantum crystal of a metal complex on a metal substrate having an electrode potential in the vicinity of a reduction potential by selection of an electrode potential (hereinafter referred to as a quantum crystal aggregation method), and when an antigen or antibody coexists in the metal complex solution, the antigen or antibody aggregates on the substrate together with the metal complex to form a solidified plasmon reaction field, and the metal complex crystals of around 100 nm are arranged regularly and physically or chemically solidified between the quantum crystals at regular intervals.

In the present invention, in the step of solidifying an antigen or an antibody by aggregation of the plasmonic metal quantum crystals described above, an antigen and an antibody are held in a buffer solution and mixed with a plasmonic metal complex solution (hereinafter, typically referred to as an Ag reagent), but by a buffer action of mixing an Ag reagent (for example, an aqueous solution of a silver complex containing a silver thiosulfate solution) with a buffer containing an inactivated virus or an antibody, it has been observed that the pH of both is shifted from an acidic region to a neutral or a weak alkaline region, and aggregation of a quantum crystal which solidifies an antigen and an antibody on a substrate becomes a desirable state (a state desirable for quantification of an antigen and an antibody) (see the following Example "pH Effect of Quantum Crystal Aggregation Form"). In short, the solidification of the present invention by aggregation of quantum crystals, compared with a conventional method in which an organic molecule is utilized on a gold thin film to be solidified as discussed above, is excellent in that an antigen and an antibody can be quantified more by counting a fluorescent point.

In an embodiment, an antigen is solidified using a quantum crystal aggregation method of a plasmonic metal complex, and the antigen solidified substrate is used for detecting an antibody in a analyte because an antibody reacts with the antigen solidified substrate with a gap or a microchannel between quantum crystals, and further, a labeled secondary antibody is used for labeling the antibody.

Figure 2A:
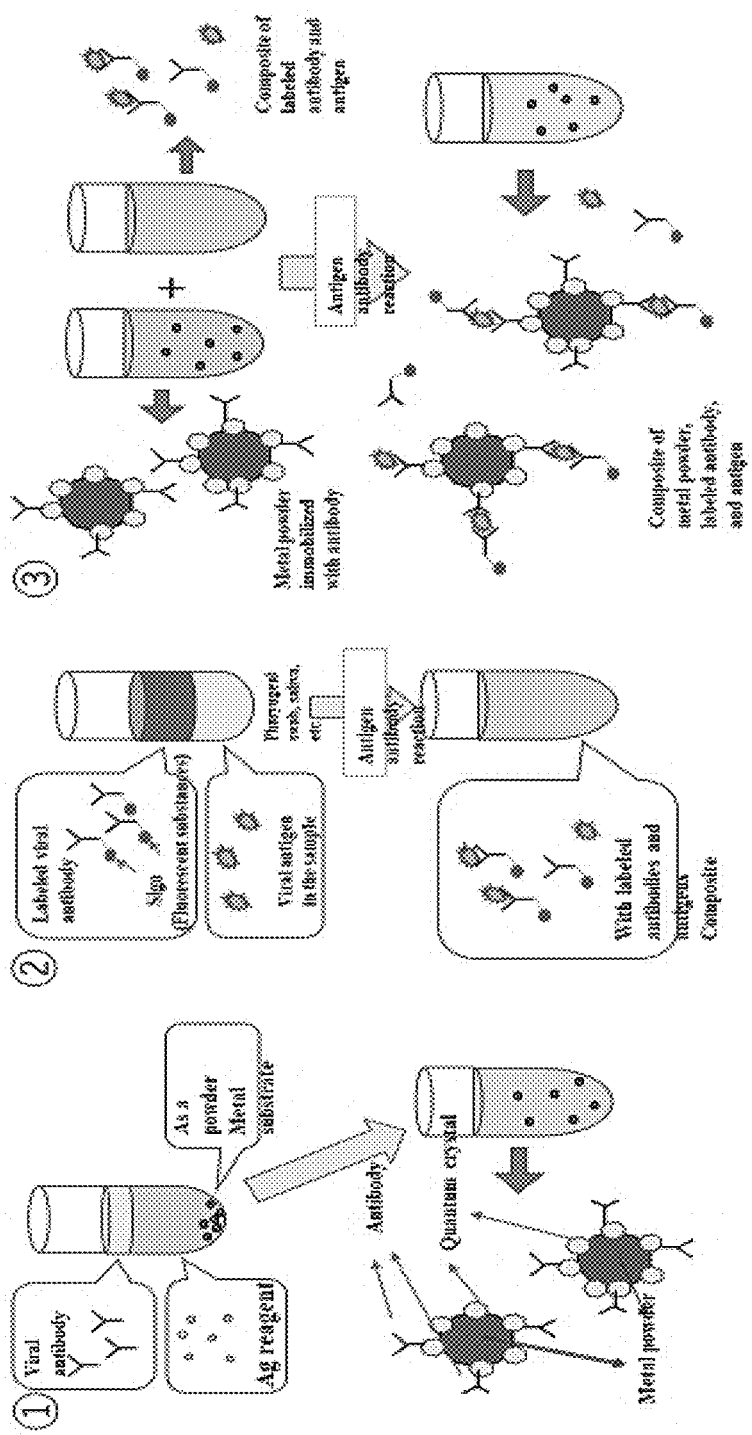
FIG. 2A shows a schematic diagram of Antigen-Antibody Reactions Using Quantum-Crystals (Sandwich Method) with Fluorescence Measurement Method for Reaction in Liquid. It comprises of steps (1) to (3) when a metal powder is used instead of a metal substrate, in step (1), an Ag reagent and an antibody are mixed into a powdered substrate, and an antibody is immobilized by quantum crystals formed in the metal powder. Then, in step (2), an antibody of a virus labeled, and a sample are mixed, and a composite is formed with a virus antigen contained in the sample and a labeled antibody by an antigen-antibody reaction. In step (3), when the solution prepared in step (1) and the solution prepared in step (2) are mixed, the composite is bound to the antibody on the metal powder by the antigen-antibody reaction.
Figure 2B:
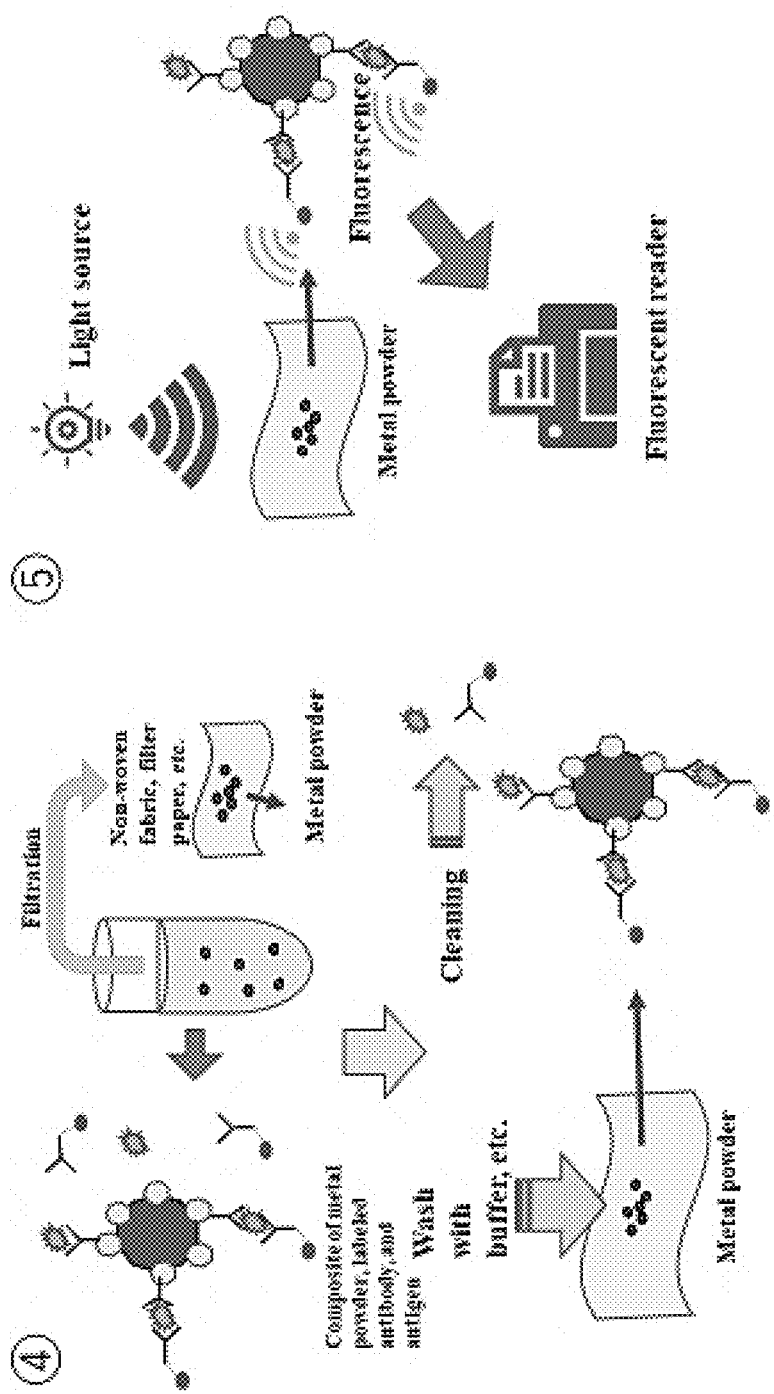
FIG. 2B shows a schematic diagram of Antigen-Antibody Reactions Using Quantum-Crystals (Sandwich Method) with Fluorescence Measurement Method for Reaction in Liquid. It comprises of steps (4) to (5) when a metal powder is used instead of a metal substrate, and in step (4), a solution prepared in step (3) is filtered by a nonwoven fabric or the like to take out only the metal powder, and the metal powder is washed with a buffer or the like to wash out the unbound composite, the antibody, and the like. In step (5), light of a light source matching a label (fluorescent substance) of an antibody is irradiated to excite, and the label is fluorescent, and fluorescence is detected by a fluorescence reader.

In an embodiment, a metal powder may be used instead of the metal substrate as shown in FIG. 2A and FIG. 2B. In this case, after washing, the remaining composite or the labeled secondary antibody is irradiated with excitation light to enhance the fluorescence of the composite or the secondary labeled antibody by surface plasmon excitation of the quantum crystal, and the fluorescence image thereof can be observed, and the number of granular fluorescence in the image is counted and detected.

In an embodiment, according to the present invention, the fluorescent labeling step can be carried out by one selected from the group comprising of a sandwich method, a direct theory method, and an indirect method, but among them a sandwich method in which an antigen is sandwiched by an antibody (primary antibody) having a fluorescent label is usually used. If the antigen is supplemented with a fluorescently labeled primary antibody and a fluorescently labeled secondary antibody, a clearer fluorescent image can be acquired.

In an embodiment, according to the present invention, it is possible to measure not only the fluorescence intensity of a viral antigen but also the number of fluorescence of a viral antigen as a virus concentration. Moreover, since the quantum crystals forming the substrate is provided with a gap or micro-flow path of nm size between the quantum crystals, interaction between the free electrons of the plasmon metal particles forming the photons and the quantum crystals incident by the excitation light occurs, thereby the surface plasmon excitation to enhance the fluorescence of each composite or secondary labeled fluorescence intensity can be detected not only entirely but also can be detected by counting the fluorescence spots. Therefore, the fluorescent counting method can be used in SPFS method to quickly test in a short time of 2 to 5 minutes, so that it is possible to provide a highly accurate diagnostic result in place of the PCR test. The PCR test needs a complicated preprocess, insensitive to primers, many protocols, and time-consuming to test. In comparison with this, the counting of the number of fluorescence corresponds to the number of viruses as well as the determination of the presence or absence of the disease, so that or the determination whether the disease is mild or severe can be made, so this method is epoch-making for the medical examination.

In an embodiment, according to the present invention, it is possible to provide an antibody which is generated in a body which is effective for a specific virus, and to provide an antibody inspection method. Fluorescence labeling is similar to that of antigens, and sandwich, direct, and indirect methods can be used.

In an embodiment, a method for quantifying a measurement target of a virus or an antibody in an analyte comprises the steps of 1) producing a solid phase substrate by a solid phase step of an inactivated virus or an antibody thereof, 2) a labeling step of fluorescently labeling a virus or an antibody solidified from an antigen-antibody reaction, 3) a fluorescence excitation step of irradiating a fluorescently labeled virus or an antibody with excitation light to obtain a punctate fluorescence image of a virus or an antibody fluorescently labeled by surface plasmon excitation, and 4) a fluorescence counting step of binarizing a fluorescence point or a particle at least 1 field measurement in the fluorescence image to adopt a fluorescence point or a particle having a predetermined threshold value or more and adopting a counting and quantifying the fluorescence point or the particle. Fluorescence scores correlate with viruses in specimens.

In an embodiment, in the solid-phase process, inactivated virus or antibody thereof is collected in a buffer and mixed with an aqueous plasmonic metal complex solution of 1000 ppm to 5000 ppm, preferably 2000 to 4000 ppm, without neutrality and dropped onto a metal substrate. The virus in the specimen is uniformly dispersed in the solid phase in the fluorescence image, and an accurate measurement can be performed by one field measurement without obtaining an average value of two or more fields.

In an embodiment, a solid phase subject in an analyte is a virus (inactivated) or an antibody thereof that produces an antibody, wherein the concentration in the analyte is 10 µg/ml or more. The sensitivity of the solidified substrate is improved by increasing the antibody concentration to be solidified. "Sensitivity" in this invention is defined as the percentage of response rate of the positive=the present inventive method positive/PCR method positive (%).

In an embodiment, fluorescence labeling in the present invention is generally a sandwich method, but a direct method is also usable in which a viral antigen is solidified and then labeled with a labeled antibody, or an antibody is solidified and then labeled, and then a labeled antigen (including one which is labeled with a fluorophore and a part of an antigen is labeled, hereinafter, the same) is used.

A direct method, or a virus antigen is solidified and then the antibody and the secondary antibody are sequentially bound and labeled, or the antibody is solidified and then the virus antigen is bound, and finally the antibody and the secondary antibody are sequentially bound and labeled.

Indirect methods are also usable. The virus antigen is usually inactivated with ethanol or the like and diluted with a buffer solution. Preferably, the labeled antibody is labeled with a fluorophore and is usually diluted with buffer.

In an embodiment, when the plasmon metal complex quantum crystal coagulation mass of around 100 nm coagulated together with the antigen or antibody on the metal substrate is irradiated with excitation light, surface plasmon excitation phenomenon occurs by the quantum crystal, and the fluorescent label of the virus or the antibody solidified together with the quantum crystal is excited. Thus, together with the measurement of less non-specific reaction, the punctate fluorescent number having a luminance value of a predetermined threshold or more by surface plasmon excitation is accurately obtained, which has a correlation with the virus or antibody concentration, it becomes possible to quantitative measurement.

In an embodiment, the fluorescence counting step according to the present invention, a result in which quantitation in the 1 field measurement is equivalent to an average value of 2 or more field measurements is obtained. This enables rapid quantitative measurements.

In the solid-phase process, antibodies that bind to two or more distinct viruses in an antigen-antibody reaction are solidified and labeled with labeled antibodies of distinct fluorescence wavelengths in the labeling process, thereby enabling quantification of two or more viruses in the analyte in one measurement.

In an embodiment, present disclosed invention is applied to influenza and Covid-19 viruses, the virus can be detected separately in one measure.

In an embodiment, as shown in FIG. 8A to FIG. 8D, there can provided a system for quantifying an antigen or an antibody to be measured in an analyte by fluorescence counting, comprising 1) a phase solidifying unit for making a phase solidified substrate on which an antibody or an antigen solidified on a metal substrate with coagulation of a plasmon metal complex quantum crystal; 2) a fluorescence labeling unit for making a labeling liquor made of a fluorescence material with an antibody or an antigen to be measured in an analyte and dropping the labeling liquor on the phase solidified substrate to make a measuring chip by means of an antigen-antibody reaction; 3) a fluorescence imaging unit of making the fluorescence image of the labeled antibody or antigen on the measuring chip as the measuring target by irradiating an exciting light thereto and observing the excited fluorescence image by a fluorescence microscope; 4) a counting unit of the number of fluorescence points of a certain selected region in the excited fluorescence image, and 5) a conveying tool for the substrate from the first position to the final position.

In an embodiment, the phase solidifying unit 1) comprises a mixer for making a phase solidifying liquor by mixing a predetermined amount of a buffer solution of the inactivated antigen or the antibody with a predetermined amount of an aqueous plasmonic metal complex solution, a metal substrate having a noble electrode potential more than that of the plasmonic metal complex, a compression syringe for dropping a quantitative amount of the phase solidifying liquor onto the metal substrate, and an air blowing means for stopping aggregation of the aqueous plasmon metal complex solution on the metal substrate by removing the phase solidifying liquor on the metal substrate under a predetermined time elapse.

In an embodiment, fluorescence labeling unit comprises a mixer for making the labeling liquor containing the antigen or the antibody to be labeled in the analyte, a compression syringe for dropping a predetermined amount of the labeling liquor on the phase solidified substrate to combine the labeled antigen or antibody with the antibody or the antigen solidified on the substrate, and a washing and drying means for washing off an unbound labeling liquor from the substrate by a washer and an air blower.

In an embodiment, the fluorescence imaging unit comprises a light source for irradiating an excitation light having a wavelength range suitable for the fluorescence substance for labeling the virus or the antibody on the measuring chip for exciting fluorescence of the labeled fluorescent substance with the quantum crystal of the plasmon metal by the excitation light, and a fluorescence microscope for observing the fluorescence image on the measurement chip by autofocusing the fluorescence image. wherein the fourth fluorescence counting means 4) comprises a means for selecting at least one region in the fluorescence image, a means for binarizing fluorescence points of the selected region to adopt a fluorescence point or points equal to or larger than a predetermined threshold value, and a quantitative means for counting number of the fluorescence points.

In another embodiment, the system for quantifying an antigen or an antibody in an analyte by fluorescence counting had better be provided with the phase solidifying unit uses the phase solidifying liquor in a substantially neutral pH range formed of the plasmonic metal complex aqueous solution of 1000 to 5000 ppm, preferably 2000 to 4000 ppm, and a neutral pH or higher buffer containing a virus inactivated or an antibody thereof to be solidified on the metal substrate, in order to produce an antibody or antigen solidified substrate in which quantum crystals of the plasmon metal complex in a measurement region of a substrate are substantially dispersed and aggregated in order to make a suitable substrate to be combined the antigen or antibody to be measured for detection. Further, the system for quantifying an antigen or an antibody to be measured in an analyte by fluorescence counting had better be provided with the fluorescence counting unit, the fluorescence point in the fluorescence image is binarized with an analysis condition selected from the brightness, the area, and the circularity to adopt or select the suitable fluorescence points among all of them in the fluorescence image.

In the present invention, a quantum crystal aggregation method is used, and a solid-phase substrate can be easily produced on a predetermined metal substrate and metal powder by using various materials described below.

(Quantum Crystal Agglutination Reaction)

When silver complex quantum crystals are coagulated as a solid-phase substrate, a copper and copper alloy substrate a phosphor bronze substrate is preferably used as an coagulation substrate.

Figures 1, 9:
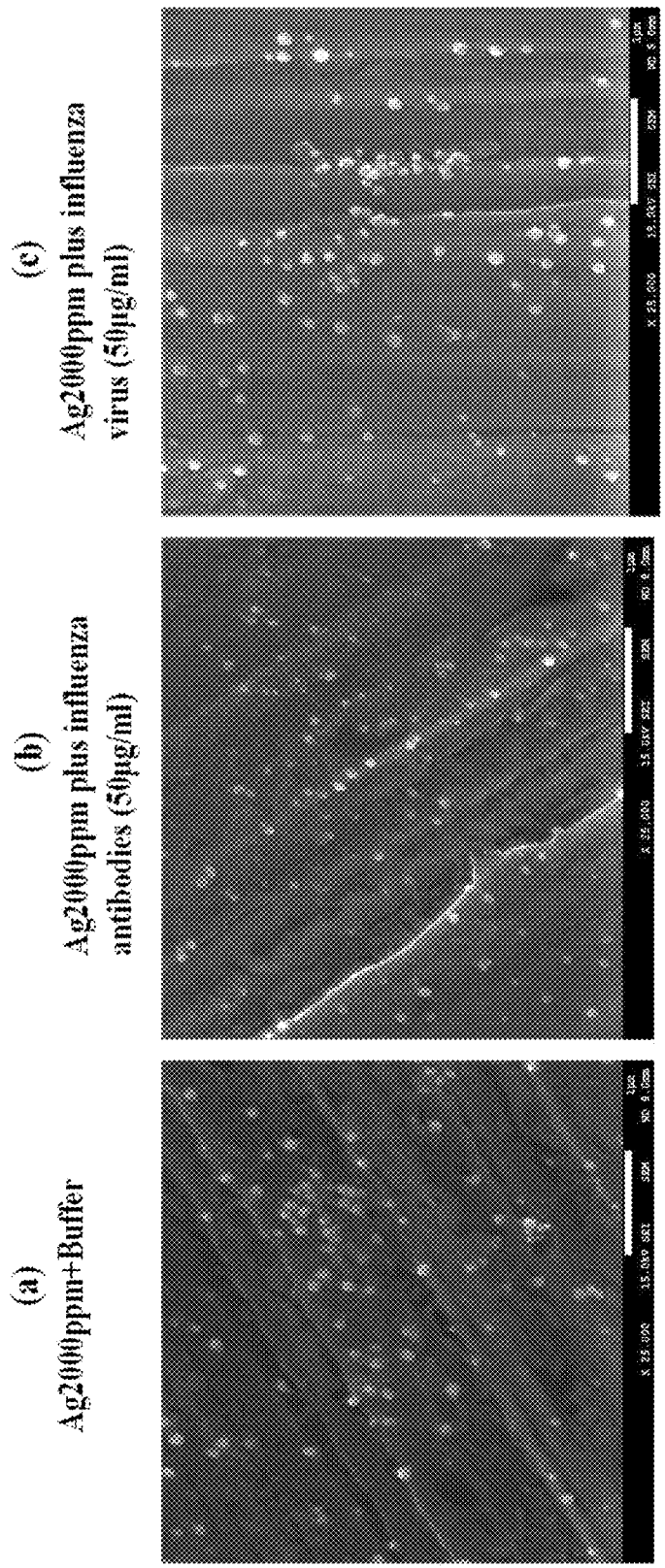
Figure 9:
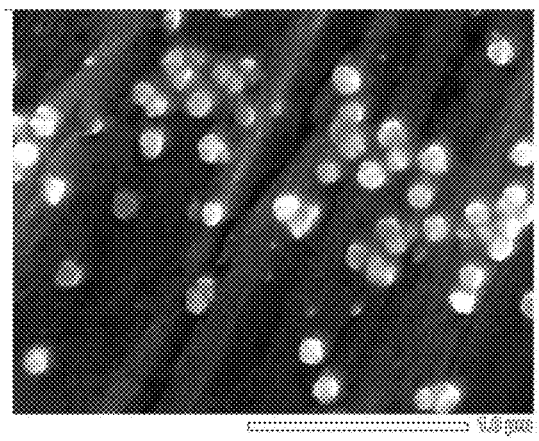
Figure 4:
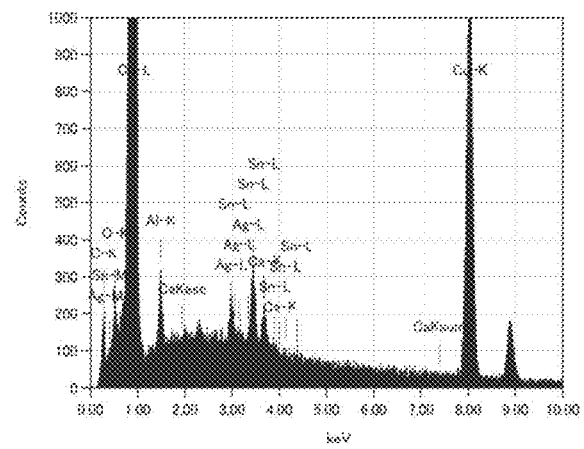

A substrate having a plasmon metal quantum crystal region used in the method of the present invention is referred to as a proteo chip. The manufacturing method thereof is as follows: 1) The aqueous solution of the metal complex is chemically reduced on a metal substrate having an electrode potential (having a larger ionization tendency) lower than that of the metal forming the complex by an electrode potential difference to aggregate quantum crystals (nano-sized metal complex crystals). In the case of a silver complex, a quantum crystal of a silver complex is formed by employing an electrode potential difference electrodeposition method by aggregating an aqueous silver thiosulfate solution on copper or a copper alloy having an electrode potential (a large ionization tendency) lower than that of silver. More specifically, the density of the metal complex in the aquatic solution should be determined primarily by the size of the quantum crystals to be formed, and should be taken into account when using a scattering agent, typically in the range of 100 ppm to 1000 ppm. However, in order to prepare a nano-size of 50 to 150 nm that should be nanoclusters depending on the virus containing the antigens or the antigens produced by the virus in the anti-virus response, it is preferable to use an aquatic solution of 1000 ppm, preferably 2000 to 10000 ppm, preferably 4000 ppm. In addition, in the solid-phasing of the antigen and antibody of the present invention, since the solid-phasing object is mixed with the inactivation solution and the buffer solution and aggregated together with the quantum crystal aqueous solution, unlike the aggregation only from the quantum crystal aqueous solution, the quantum crystal tends to disperse on the solid-phased substrate (see FIGS. 9-1(*a*), (*b*) and (*c*)). 2) The metal complex forming the quantum crystal is selected to have a complex stability constant (log β) or more shown in Formula (I) which correlates with the electrode potential E of the supported metal.

$$E° = (RT/ZF)\ln(\beta i) \quad \text{Equation (I):}$$

Where E° represents the standard electrode potential, R represents the gas constant, T represents the absolute temperature, Z represents the ionic number, and F represents the Faraday constant.

Here, when the metal complex is a complex of a plasmonic metal selected from Au, Ag, Pt or Pd, it has a localized surface plasmon resonance enhancing effect on excitation light. In particular, when the metal complex is a silver complex, it is preferably formed by the reaction of a silver complexing agent having a stability constant (formation constant) (log βi) of 8 or more with silver halide, and silver chloride is preferred as the silver halide, and 1 kinds selected from thiosulfate, thiocyanate, sulfite, thiourea, potassium iodide, thiosalicylate, and thiocyanurate are preferred as the complexing agent. Silver complexes have quantum dots comprising of nanoclusters with an average diameter of 5-20 nm, resulting in quantum crystal sizes of 50-150 nm.

(Study of Solid Phase Concentration, Part 1)

In solid-phase techniques using quantum crystals, the concentration of quantum crystal reagents (Ag reagents) is very important. Therefore, Biotin is solidified by changing the concentration of the quantum crystalline reagent to be solidified, and Avidin to which FITC label is imparted is detected by fluorescent microscopy using a Avidin-Biotin bond.

FITC-Avidin VEC, Inc. "FLUORESCEIN AVIDIN D"CatNo. A-2001"

Biotin Wako "(+)-Biotin"CatNo. 023-08711.

Solid-phase substrates with Biotin (5 µg/ml) solidified with quantum crystal concentrations of 1000, 2000, 3000, 4000, and 5000 ppm are prepared (1 min solidification time). Next, FITC-Avidin (5 µg/rap is dropped onto a Biotin solidified substrate to measure a Avidin to which a FITC label is imparted using a Avidin-Biotin bond with a fluorescence microscope "BZ-X710" manufactured by Keyence Co., Ltd., and an average brightness value of the obtained fluorescence image is calculated (reaction time 1 min) Consequently, it can be concluded that Biotin was more solid-phased and FITC-Avidin bound the highest mean brightness was 2000 ppm at 1000 ppm (mean brightness value 54 of images), 2000 ppm (69), 3000 ppm (62), 4000 ppm (59), and 5000 ppm (59). This is probably because, if the amount of quantum crystals is small, the amount of solidified Biotin is small, and if the amount of quantum crystals is large, the solidified Biotin is buried, so that FITC-Avidin is detected less.

(Examination of Solid Phase Concentration, Part 2)

The optimum concentration of the quantum crystal reagent was also examined in the detection of the influenza virus using the antigen antibody reaction.

Influenza antibodies were solidified by changing the concentrations of quantum crystals to be solidified, and influenza antibodies to which influenza viruses and FITC labels were attached were measured by fluorescence microscopy using an antigen-antibody reaction. Fluorescence spots were counted from the obtained fluorescence images (antigen-antibody reaction-sandwich method).

Influenza antibodies: Hytest "Monoclonal Mouse anti-influenza A haemogglutinin H1"CatNo. 3AH1"

Influenza virus: HyTest "Influenza A(H1N1)virus"CatNo. IN73-3"

FITC Influenza (ARP. Anti-Influenza A virus(H1N1) FITC")CatNo.)12-6250-3

Equal amounts of influenza antibodies (100 µg/ml) at each concentration of quantum crystal concentrations of 2000, 4000, and 6000 ppm are mixed with buffer and dropped onto a metal substrate to create a solidified substrate (1 min of solidification time)

Next, a composite formed by mixing an inactivated influenza virus (10 μg/ml) with an influenza antibody labeled with FITC (25 μg/ml) is dropped onto a solid-phase substrate (reaction time 1 minutes), and an unbound composite or a FITC antibody is washed away with water or a buffer solution.

The chips are measured with a Keyence fluorescence microscope "BZ-X710" and the fluorescence points above predetermined thresholds of the obtained fluorescence images are counted.

As a result, the most influenza virus-containing composite could be detected in the case of solidification of influenza with 2000 ppm of quantum crystals (1000 ppm as a whole) as in the case of Avidin-Biotin binding.

Images at each concentration of 2000, 4000, and 6000 ppm when the influenza antibody is solidified at the quantum crystal concentration are as shown in FIG. 12.

(Quantum Crystal Concentration (ppm) and Count)

2000 228 counts, 4000 counts (159 counts), 6000 counts (47 counts)

Measuring conditions: Threshold 62 One field of view measurement of the blurring filter-free×10× lens (Here, one field of view measurement refers to a method of acquiring only one portion of the tip unlike the case of JP-A-2019-234330, as shown in FIG. 16, which leads to a reduction in measurement time).

The equipment used for the measurement of each quantum crystal is as follows. Instrument: Keyence Fluorescent Microscopy BZ-X710, Light source: Metal halide lamp 80 W Fluorescent filter: BZ-X filter GFP (525±25), Analysis software: BZ-X Analyzer.

(Adjustment of Solid-Stated Substrate)

In addition to an aqueous solution of a quantum crystal metal complex, a solid phase substrate of the present invention has a different aggregation action in that it is mixed with an inactivating solution containing a virus and an antibody containing an antigen to be solidified and/or a buffer solution to solidify into aggregation of quantum crystals, but basically, an antibody or an antigen can be solidified using a quantum crystal aggregation method (JP 2016-197114A) for producing quantum crystals of a plasmonic metal complex. Therefore, the method described in JP-A-2016-197114 is cited and referenced herein.

However, the virus and the antibodies it produces are added in an inactivating solution or buffer and mixed with a plasmonic metal complex reagent (e.g., an aqueous solution of silver thiosulfate) for solidification and added onto a solidified substrate to aggregate.

In the case of the solid phase of antigens and antibodies by quantum crystals, unlike in the case of quantum crystals alone, it is affected by the interaction with the buffer and the change in pH.

FIG. 9 mixes an equal volume of phosphate buffer into 2000 ppm of an aqueous solution of silver thiosulfate (Ag reagent), which serves as a control (see FIG. 9-1(*a*)).

An SEM image of a solid-phase substrate obtained by adding an antibody (influenza antibody: ARP Anti-Influenza A virus(H1N1) FITC") CatNo. 12-6250-3) and an antigen (inactivated influenza antigen: influenza virus: HyTest "Influenza A(H1N1)virus"CatNo. IN73-3") to a phosphate buffer solution so as to be 50 μg/ml, respectively, and mixing an equal amount to 2000 ppm of an aqueous silver thiosulfate solution (Ag reagent) is compared with the SEM image of the solid-phase substrate of the control (FIG. 9-1 (*a*)) (FIG. 9-1 (*b*)).

It can be seen that when buffer is added, the quantum crystals diffuse throughout, and antibodies and antigens bind on the quantum crystals to form a solid phase.

Such scattered aggregation of quantum crystals appears to create a situation in which fluorescence spot counting in a fluorescence image is possible, whereby, when a substrate on which an antigen and an antibody are solidified is labeled, by irradiation of excitation light, fluorescence of a composite is excited by surface plasmon, and the number of granular fluorescence observable as granular fluorescence can be detected as a virus quantity in the fluorescence image.

This is because, as shown in FIG. 9-2, FIG. 9-3, and FIG. 9-4, the detection of the Ag component is observed in each quantum crystal other than the Cu and Sn components of the phosphor bronze substrate, and it can be confirmed that the solid phase formation is performed by the quantum crystal silver complex. Note: Antibodies and antigens are not detected.

(Preparation and Sensitivity of Influenza Antibody Solid-Phase Substrate)

When an equal-volume blend solution (pH7.2) of 2000 ppm (pH5.2) of the above-mentioned silver sulfate solution (Ag reagent) and 0.1 mor/L protein buffer (pH7.4) of the flu antibody (50 μg/ml) is added on a photo bronze board, it is solidified in about one minute, so that the remaining liquid on the metal board is blown by air to obtain an antibody solidified board (FIG. 10(*a*)).

FIG. 10B shows an image of a clear portion of the solid-phase substrate.

The influenza antibody with FITC label which changed the concentration using the above-mentioned quantum crystal aggregation method was solidified to create the antibody solidification substrate, and the fluorescent point of each fluorescent image obtained was counted.

FITC influenza antibodies (ARP Anti-Influenza A virus (H1N1)FITC") CatNo. 12-6250-3) were used.

To a 2000 ppm aqueous solution of silver thiosulfate (Ag reagent), an equal amount of the above antibodies (250, 125, 62.5, and 31.25 μg/ml) is mixed and dropped onto a substrate to prepare various solid-phase substrates (FIG. 11 (*a*)). The time required is about 1 minute.

As shown in FIG. 11 (*b*), the solid-phase substrate was observed by a Fluorescence Microscope (Keyence BZ-X710), and measured by counting the flesh point above a predetermined threshold its fluorescence sensitivity.

As a result, it has been found that the number of counts increases depending on the concentration of the solidified substrate of the present invention.

That is, the solidified substrate according to the present invention has an antibody quantitatively solidified and is quantified as shown in FIG. 12.

Thus, it can be seen that, according to the invention, antigens and antibodies can be quantitatively solidified quantitatively.

(Virus Solid Phase)

FIG. 13 shows the steps of the direct test for influenza virus (immobilization of inactivated influenza virus).

Fluorescence puncta are counted from fluorescence images obtained by dropping an influenza antibody with a FITC label onto a substrate in which an inactivated influenza virus is solidified using a quantum crystal aggregation method (this is referred to as a direct method using an antigen-antibody reaction)

Influenza virus: HyTest "Influenza A(H1N1)virus"CatNo. IN73-3"

FITC Influenza (ARP. Anti-Influenza A virus(H1N1) FITC")CatNo.)12-6250-3

Figure 10:
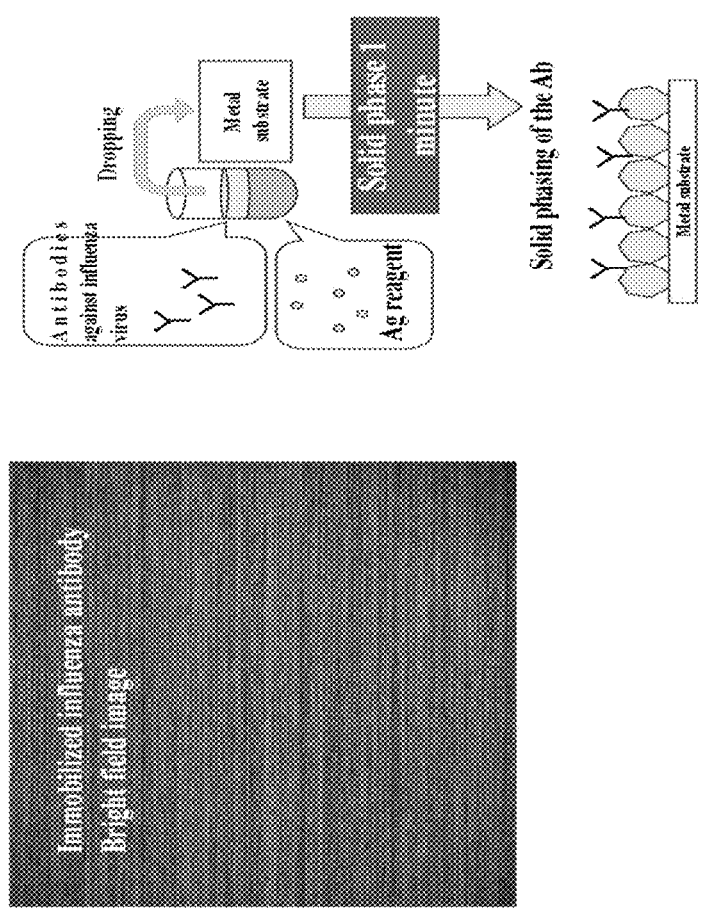
FIG. 10 shows an image diagram (a) showing a method for preparing an influenza-based solid-phase substrate and a clear part image (b) of a solid-phase substrate. Conditional Quantum Crystals 2000 ppm, Influenza antibody (50 µg/ml). Equipment used.
Figure 11A:
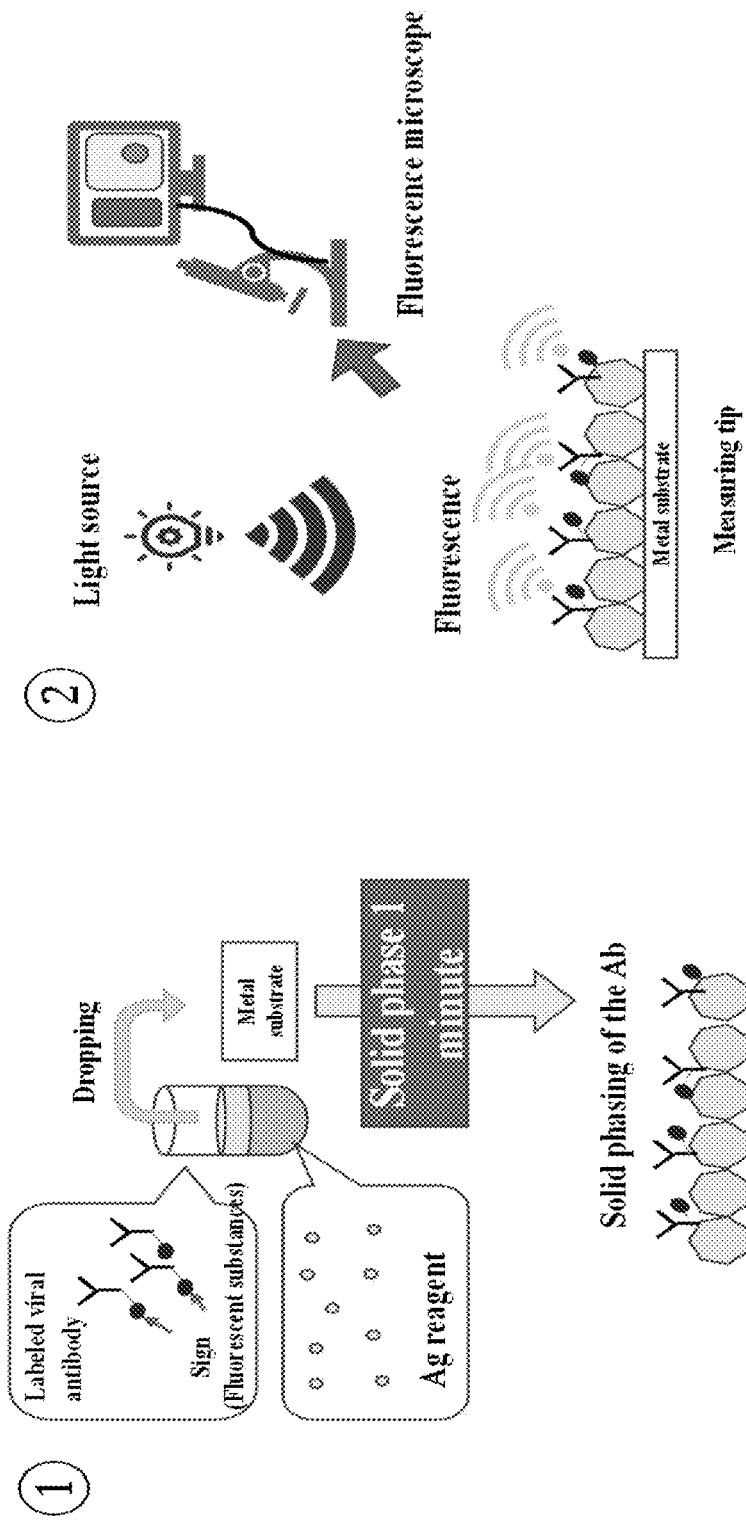
Figure 11B:
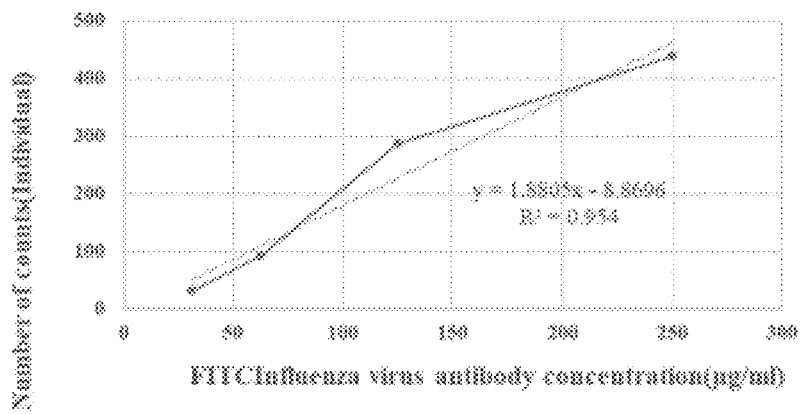
Figure 12:
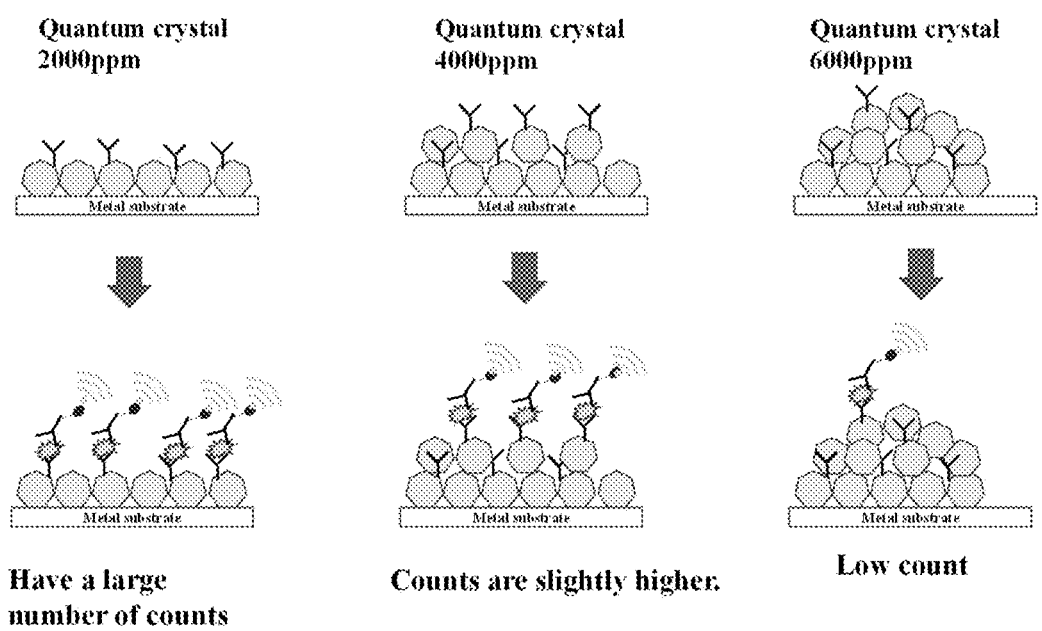
Figure 13:
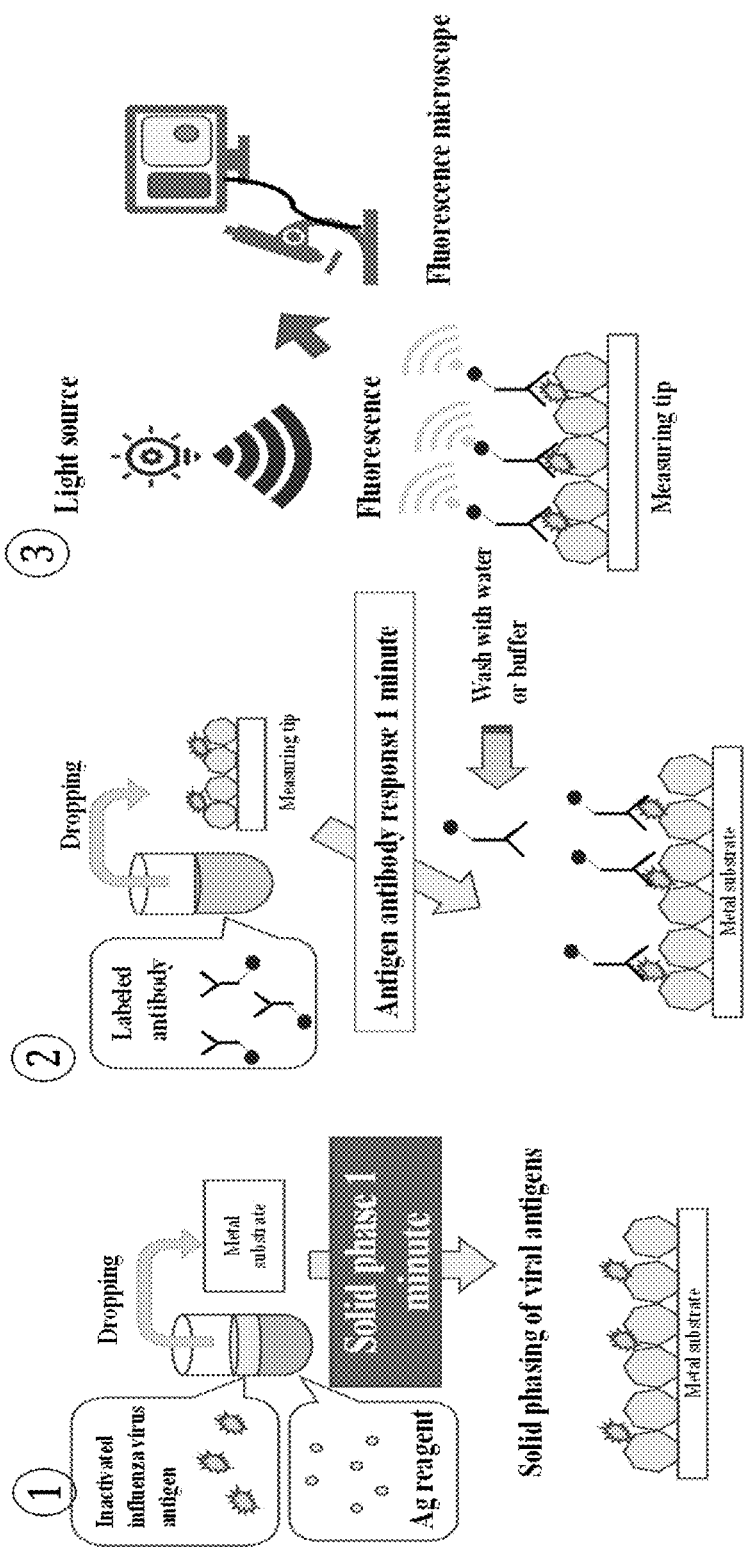

An equal volume of a mixture of 2000 ppm of the above aqueous solution of silver thiosulfate (Ag-reagent) and a phosphate buffer solution of influenza virus (50 µg/ml) in the preceding period (pH74) is added onto a phosphor bronze plate to prepare a viral solid phase substrate (solid phase in about 1 minutes). For comparison, a virus-free buffer is mixed with a quantum crystalline Ag reagent to form a solidified substrate. Then, influenza antibody (25 µg/ml) with FITC label is added dropwise to the above two solidified substrates (reaction time is only 1 min). Rinse unbound composite or FITC with water or buffer. The residual liquid on the metal substrate was blown off with air to obtain an antibody solid-phase substrate (FIG. 10A). FIG. 108 is a fluorescence image of the solid-phase substrate.

(Solid Phase Conversion of the Antibody (1)

Figure 14:
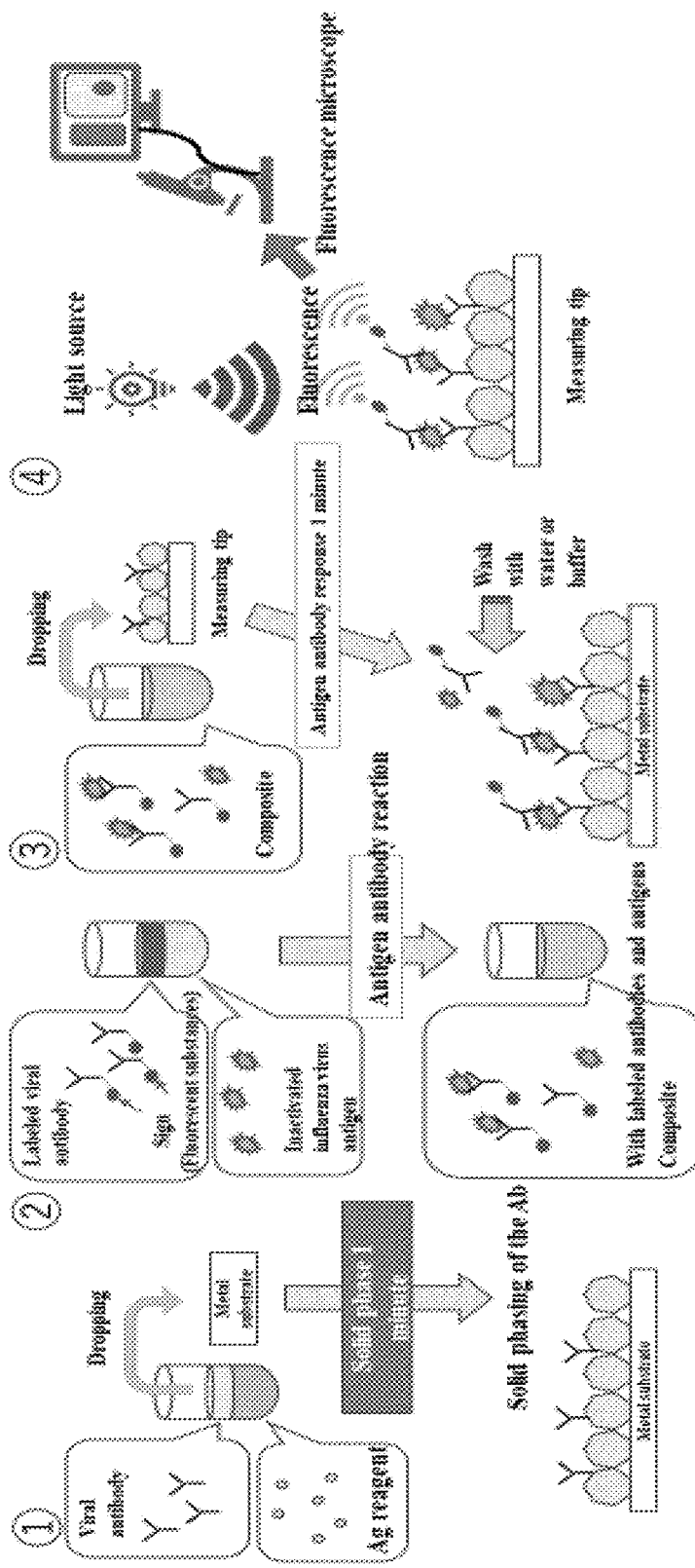

FIG. 14 shows the test steps of the influenza virus sandwich method (immobilization of influenza antibodies).

Influenza antibodies are composited with influenza antibodies labeled with FITC and inactivated influenza viruses onto substrates that have been solidified using a quantum-crystal agglutination method. The composited influenza antibodies are added dropwise and the fluorescence points are counted from the fluorescence images obtained by the antigen-antibody reaction (referred to as a direct method using the antigen-antibody reaction).

Influenza antibodies: Hytest "Monoclonal Mouse anti-influenza A haemogglutinin H1"CatNo. 3AH1"

Influenza virus: HyTest "Influenza A(H1N1)virus"CatNo. IN73-3"

FITC Influenza (ARP. Anti-Influenza A virus(H1N1) FITC")CatNo.)12-6250-3

An equal volume of a mixture of 2000 ppm of the above aqueous silver thiosulfate solution (Ag reagent) and an influenza antibody (50 µg/ml) phosphate buffer solution (pH72) is added onto a phosphor bronze plate to prepare an antibody-solidified substrate (solid phase in about 1 minutes).

Next, influenza antibodies (25 µg/ml) with FITC labeling are mixed with influenza virus to form a composite, which is added dropwise to a solid-phase substrate (reaction time is only 1 min).

Rinse unbound composite or FITC with water or buffer.

The measurement tip is measured with KEYENCE fluorescence microscopy "BZ-X710" and the fluorescence points above a predetermined threshold of the obtained fluorescence image are counted.

Measurement conditions and equipment used are the same as for the solid phase formation of viruses.

(Solid-Phase Conversion of the Antibody. (2)

Figure 15:
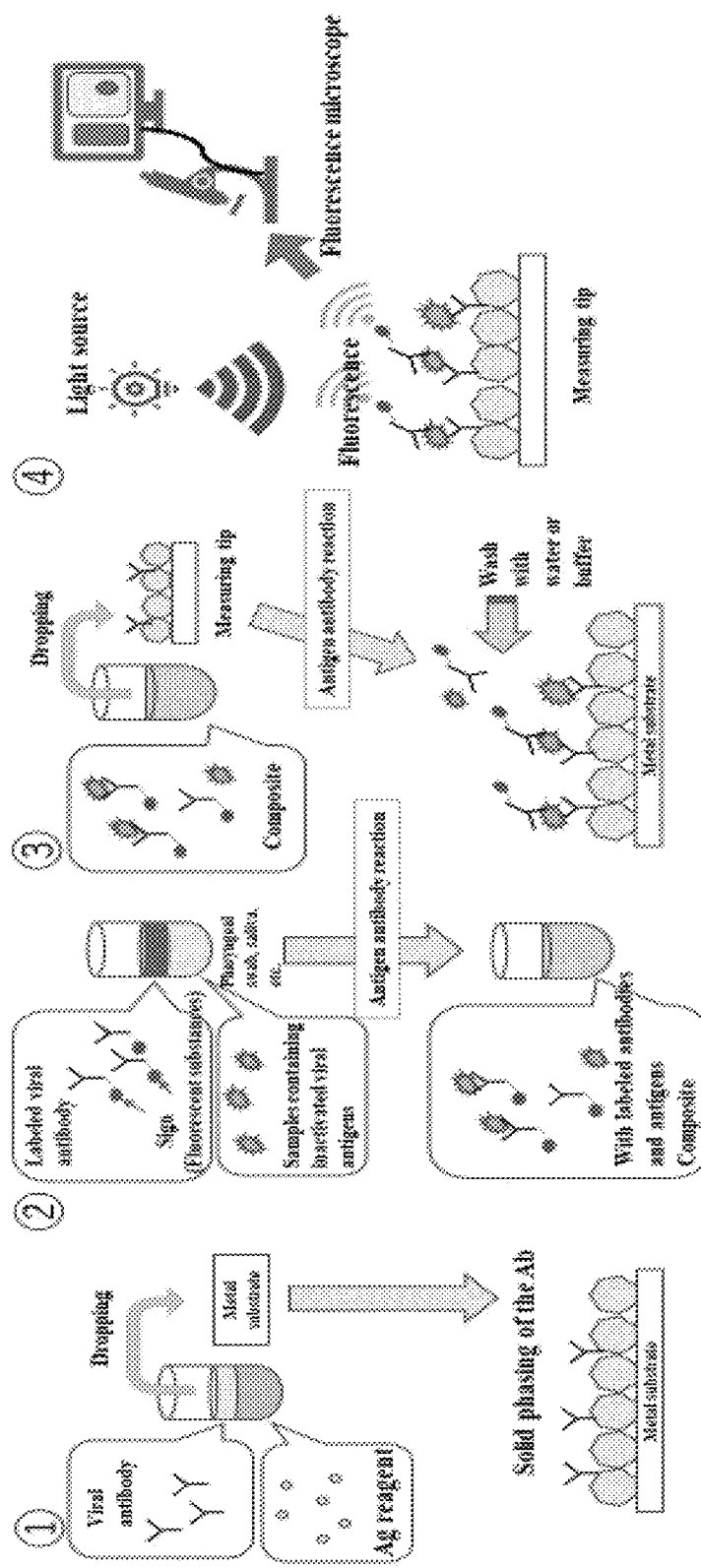

FIG. 15 shows the inspection process.

Fluorescent puncta are counted from fluorescent images obtained by dropwise addition of a composite of an inactivated COVID-19 patient-sample and a FITC labeled COVID-19 antibody to a substrate in which a COVID-19 antibody is solidified using quantum crystals.

COVID-19 antibodies: GeneTex "SARS-COV-2 spike antibody" CatNo. GTX135356"

FITC labeled COVID-19 antibodies: GeneTex "SARS-COV-2 spike antibody" CatNo. GTX135356 with FITC labeling (labeling rate 8.64).

A COVID-19 antibody (50 µg/ml) is mixed into a 2000 ppm quantum crystalline reagent (Ag thiosulfate) in an equal amount and dropped onto a phosphor bronze substrate to prepare an antibody solidified substrate.

Next, a pharyngeal wipe obtained from a COVID-19 is inactivated with 70% ethanol, and a composite formed by mixing a FITC labeled COVID-19 Ab (34.5 µg/ml) is dropped onto a solid-phase substrate.

Unbound composite and FITC antibodies are washed away with water or buffer.

The measurement tip is measured with KEYENCE fluorescence microscopy "BZ-X710" and the fluorescence points above a predetermined threshold of the obtained fluorescence image are counted.

Measurement conditions and equipment used are the same as those of the solid phasing of viruses.

As a result, viruses were also detected in two samples collected from the pharyngeal swab of two patients with COVID-19. The number of counts represented the patient's symptoms. Note that 70% ethanol was used as the blank. The results showed blank: count number 8 (relative value 0), sample 1: count number 16 (relative value 8), sample 2: count number 51 (relative value 43). The relative value is the count number when the count number of blanks is set to 0. Even if the sample is saliva, the count is slightly lower, but the same result is obtained.

(Production of Quantum Crystals)

A solution of 2000 or 4000 ppm of silver thiosulfate in water was prepared, and a drop of the solution was dropped onto a phosphor bronze plate, allowed to stand for about 1 minute, and the solution was blown off. The SEM image showed that quantum crystals were produced.

In the photograph showing various SEM images of the nanoparticle aggregate (quantum crystal) produced in Example 1, the crystal is a thin hexagonal prism of about 100 nm, and irregularities on the order of several nm appear on the surface.

Facets peculiar to metal nanocrystals could not be confirmed.

The correlation between the standing time after dropping on a phosphor bronze hill and the quantum crystal shape is shown.

First, it was observed that a hexagonal quantum crystal was formed and grown while maintaining its shape, and in the graph showing the result of EDS spectrum (elemental analysis) of the quantum crystal, the crystal formed on the phosphor bronze plate detected elements derived from silver and a ligand, but only silver was detected when a 1000 ppm aqueous solution of silver thiosulfate was prepared on the copper plate, one drop of the solution was dropped on the copper plate, the solution was left to stand for about 3 minutes, and the solution was blown off.

(Quantum Crystal Aggregation Theory)

In the case of a 2000 or 4000 ppm silver thiosulfate complex aqueous solution, when dropped on a phosphor bronze plate and left for 1 minute, it was confirmed from the SEM image that the quantum crystal was formed in a hexagonal prism shape of around 100 nm, and that each hexagonal prism-shaped quantum crystal had roughness on the order of several nm, but facets peculiar to the metal nanocrystal could not be confirmed, and elements derived from silver and ligands were detected by EDS elemental analysis, so it is presumed that the whole is a nanocrystal of a silver complex, and the roughness appearing on its surface is spread by forming quantum dots as clusters of silver in the complex.

Looking at the phenomenon in which the silver complex quantum crystal of the present invention is formed on the phosphor bronze plate, while the silver-only nanoparticles are precipitated on the copper substrate, since only silver (0.80) is precipitated on the copper substrate because the equilibrium potential of the silver thiosulfate complex is 0.33, which is equivalent to the electrode potential of copper (0.34), and in the case of phosphor bronze, the electrode potential is 0.22, which is slightly lower, it is considered that the crystals of the silver complex are precipitated.

Therefore, it was found that 1) the complex aqueous solution is a dilute region of 500 to 2000 ppm in order to prepare quantum crystals, 2) the electrode potential of the supported metal is slightly base to the equilibrium potential of the metal complex aqueous solution, and 3) it is important that the metal complex aggregates at the electrode potential difference, but it is desirable to use Ag thiosulfate quantum crystal reagents having a concentration higher than that of 2000 ppm for the solid phase of the antigen antibody.

The substrate can be polished with sandpaper to physically remove the surface oxide coating, and a silver thiosulfate solution is dropped thereon to form a solid-phase substrate by the aggregation action of quantum crystals.

Substrate surface physical state may affect the formation state of the quantum crystal, which may affect the measured value.

Figure 4:
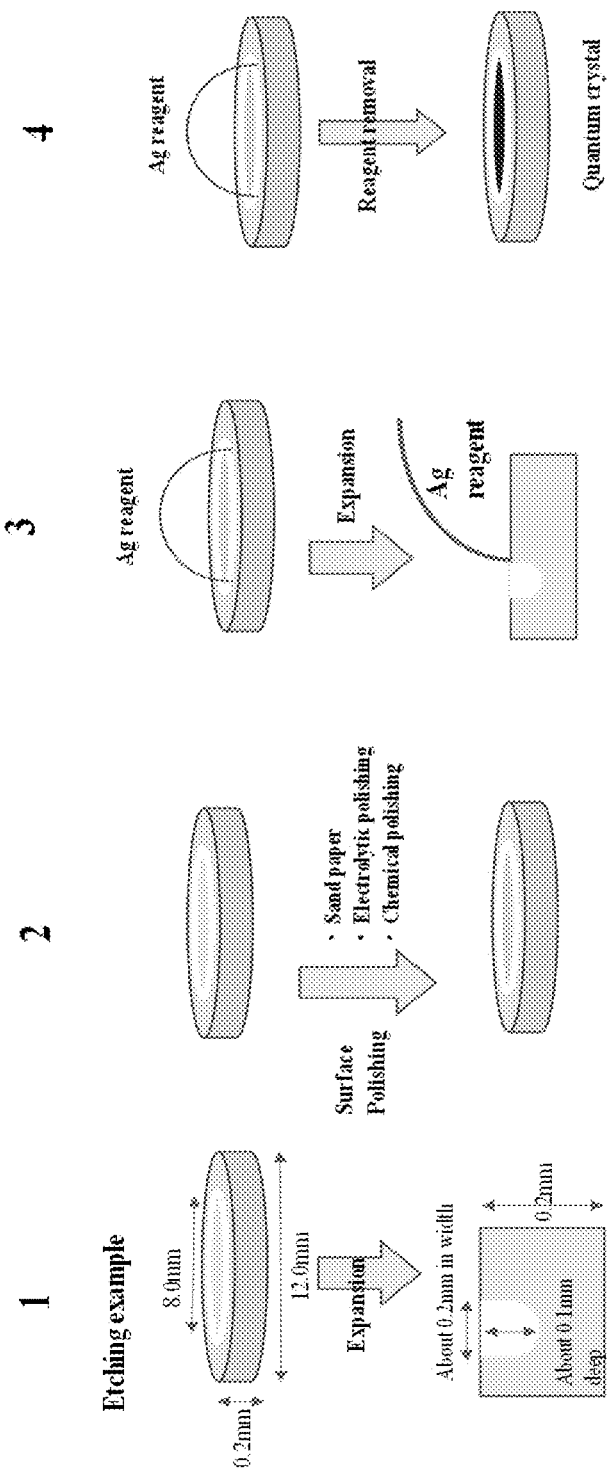
FIG. 4 shows a grooving into phosphor bronze plate (etching). Keeping the Quantum Crystal Area Value constant. The process diagram showing a method of manufacturing a quantum crystal substrate of the present invention, in step (1), the inside of the circular phosphor bronze plate, placing a circular groove. Inside a phosphor bronze plate with a thickness of 0.2 mm (a circle with a diameter of 12 mm), insert a circular groove with a diameter of 8 mm, and make the groove have a depth of about 0.1 mm and a width of about 0.2 mm. In step (2), the surface of the phosphor bronze plate is polished to remove an oxide film on the surface. As a method of removing, there are a method of polishing with paper as a physical treatment and a method of chemical polishing in which a surface is dissolved by an electrolytic polishing or a chemical agent using an electrode as another polishing method. In step (3), an Ag reagent is dropped into the inner groove of the polished phosphor bronze plate. When Ag reagent is dropped inside the groove, the reagent stays inside the circle due to the surface tension of the groove. In step (4), the dropped Ag reagent stays inside the groove, so that quantum crystals of the area fraction of the groove are generated. Since it is possible to form a quantum crystal in the same area, it is possible to provide a constant quantum crystal substrate.
Figure 5:
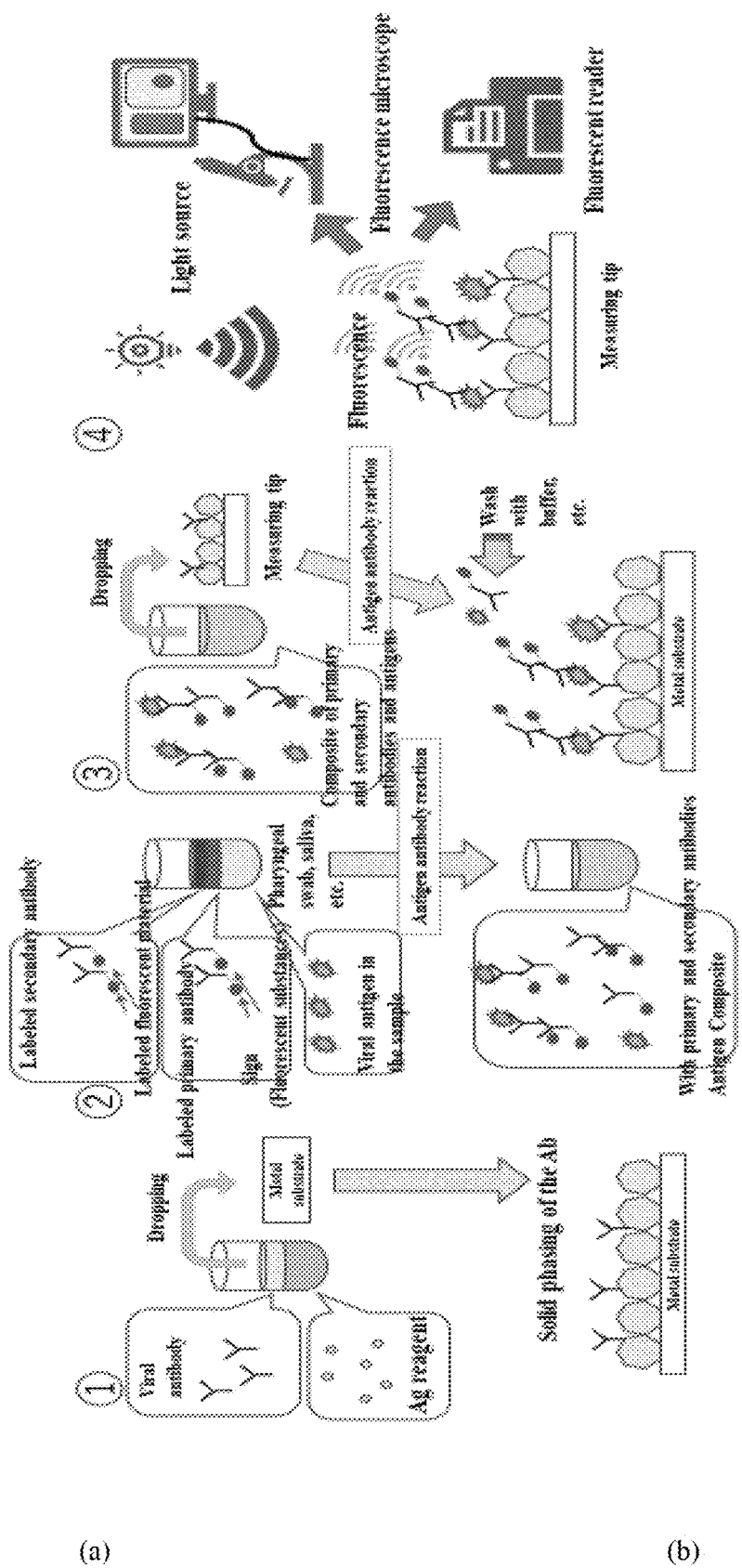
FIG. 5 shows a method to increase the sensitivity of fluorescence by Antigen-Antibody Reaction Using Quantum Crystals (Sandwich Method). The schematic diagram showing a virus detection method using a first labeled antibody and a second labeled antibody capable of binding to each other as the labeled antibodies of the first and second methods of the fluorescent labeling process of the present invention, in step (1), an Ag reagent and an antibody of a virus are mixed and dropped onto a metal substrate. The antibody is solidified on the quantum crystal formed on the metal substrate. In step (2), when a labeled primary antibody and a secondary antibody and a sample are mixed, a composite is formed with a virus antigen and a labeled antibody contained in a sample by an antigen-antibody reaction. In step (3), when a composite of a labeled primary antibody and a secondary antibody and an antigen is dropped onto a measurement chip, a composite is bound to an antibody on a substrate by an antigen-antibody reaction. Unbound composite or antibodies should be washed off with buffer or other suitable medium. In step (4), light of a light source matching the label (fluorescent substance) of the primary antibody and the secondary antibody is irradiated to excite, and the label is fluorescent. This is detected by fluorescence microscopy or fluorescence reader

Therefore, in order to keep the quantum crystal formation region constant, as shown in FIG. 4, 1) circular groove processing (etching processing) is performed on the substrate dropping region of the phosphor bronze plate, 2) the inside of the region is used as it is or sandpaper polishing, electrolytic polishing, and chemical polishing are performed, 3) Ag reagent solution (2000-4000 ppm silver thiosulfate solution) is dropped and accumulated in the circular groove by surface tension, and 4) thereafter, the coagulation state of the quantum crystal is removed to be secured.

As a result of observing the coagulation state and examining the variation of the measurement result, it was found that there was the variation of the measurement result by use, electropolishing, chemical polishing, and sandpaper polishing as it is.

(Subject of Solid Phasing)

Subjects of the solid phase formation include heavy metals and proteins as well as viruses, bacteria, fungi, and the like, which are viruses that cause antibodies to be produced by the immune function of humans and animals. Also included are antibodies produced by such viruses.

Antibodies include five classes of monoclonal antibodies, including IgA, IgD, IgE, IgG, and IgM in animal species such as rats, mice, rabbits, and humans; antibodies, including five classes of IgA, IgD, IgG, and IgM in rabbits, goats, rats, mice, and chickens; some fragmented antibodies in the Fc region, the Fab region, the heavy chain, the antigen binding site, and the hinge region; and some recombinant antibodies. A human antibody obtained by infecting human B lymphocytes with a virus (EBV, etc.) and cloning an antibody gene.

Viruses include viruses such as plant viruses that infect plants such as coronaviruses, influenza viruses, or animals such as avian influenza viruses or adenoviruses, and bacterial viruses that infect bacteria such as tobacco mosaic virus, as well as some fragmented viruses such as spikes on the surface of viruses and nucleocapsids of viruses, as well as recombinant viruses and fragmented parts.

In the present invention, samples collected from humans and animals and samples containing inactivated viruses and fragmented parts are included as solid phase objects, and body fluids collected from humans and animals such as pharyngeal swab, saliva, blood, and urine are included as samples.

Example 1 of Solid Phased Substrate

Examples are given in which quantum crystals and biotin having a binding ability with avidin are solidified.

A mixture of Ag reagent (1000 ppm, 20 µl) and biotin (5 µg/ml, 20 µl) for producing quantum crystals is prepared and dropped into a phosphor bronze plate, and biotin is solidified into quantum crystals purified on a substrate.

Next, avidin imparted with a FITC fluorescent label having a binding ability with biotin is dropped onto a biotin solid-phase substrate.

Then, biotin and avidin imparted with FITC fluorescent label are bound, and the fluorescence of FITC on the grain is observed when observed by fluorescence microscopy.

It can be seen that a solid-phase substrate in which biotin is solidified on a quantum crystal can be obtained by dropping a mixture of a quantum crystal and biotin.

From this fact, it was found that a molecular compound or the like can be formed into a solid phase on the quantum crystal substrate. (Ag reagents range from 500 ppm to 10000 ppm, preferably from 1000 to 5000, more preferably from 2000 to 4000 ppm, and the biotin to be solidified has a range from 1 pg/ml to 1 g/ml)

Example 2 of Solid Phased Substrate

A solution obtained by mixing an equal amount of Ag reagent (2000 ppm, 12.5 µl) and hemagglutinin H1 influenza A antibody (25 µg/ml, 12.5 µl) for producing quantum crystals is prepared and dropped onto a phosphor bronze plate, and the hemagglutinin H1 influenza A antibody is solidified into a quantum crystal purified on a substrate.

Next, a composite of a hemagglutinin H1 influenza A antibody, a H1N1 influenza virus that binds to the hemagglutinin H1 influenza A antibody in an antigen-antibody reaction, and a H1N1 influenza virus antibody to which a FITC label has been added is dropped onto a hemagglutinin H1 influenza A antibody-immobilized substrate.

Then, the complex of influenza virus and FITC labeled antibody was combined to the solid-phase antibody of the solid-phase substrate, and the fluorescence of FITC on the particle was observed when observed by fluorescence microscopy.

As a result, it was found that a solid-phase substrate in which the hemagglutinin H1 influenza A antibody was solidified on the quantum crystal was obtained by mixing and dropping the quantum crystal with the hemagglutinin H1 influenza A antibody.

From this fact, it was found that an antibody or the like can be formed as a solid phase on the quantum crystal substrate. (wherein the Ag reagent has a range of 500 ppm to 10000 ppm, preferably 1000 to 5000, more preferably 2000 to 4000 ppm, and the hemagglutinin H1 influenza A antibody that solidifies has a range of 1 pg/ml to 1 g/ml)

Example 3 of Solid Phased Substrate

In this case, a solution obtained by mixing an equal amount of Ag reagent (4000 ppm, 12.5 μl) and hemagglutinin H1 influenza A antibody (100 μg/ml, 12.5 μl) for producing quantum crystals is prepared and dropped onto a phosphor bronze plate, and the hemagglutinin H1 influenza A antibody is solidified into a quantum crystal purified on a substrate.

Next, a complex of H1N1 influenza virus (100 μg/ml, 5 μl) which binds to hemagglutinin H1 influenza A antibody in antigen-antibody reactions and a H1N1 influenza virus antibody (50 μg/ml, 5 μl) to which a FITC label has been applied is dropped onto a solid plate of hemagglutinin H1 influenza A antibody.

Complexes of influenza virus and FITC labeled antibody were bound to the solidified antibodies of the solidified substrates, and fluorescence of FITC on the grains was observed as in the images below when observed by fluorescence microscopy.

The equipment used is as follows. Instrument: Keyence Fluorescent Microscopy BZ-X710, Light source: Metal halide lamp 80 W, Fluorescent filter: BZ-X filter GFP (525±25), Analysis software: BZ-X Analyzer.

(Analysis Method of Fluorescence Images)

Fluorescence images were analyzed as shown in FIGS. 16 (1) to (3).

Step (1) is an image acquiring step, in which a fluorescence image obtained by measuring is taken into an image analyzing software "BZ-X Analyzer" and analyzed (fluorescence is observed as a round particle).

Here, as shown in FIG. 16, to take only one objective 10× lens (one field measurement), counting by binarization (count) the shooting time is as fast as 3.5 seconds, it may take a plurality of images (see the fluorescence measurement method of JP-A-2019-234330).

The step (2) is a binarization step, in which all of the fluorescent grains having a luminance value or more equal to the set luminance value are extracted and binarized (the extracted fluorescent grains having a luminance value or more equal to the set luminance value or more equal to the red grains) with respect to the entire range of the fluorescent image.

Step (3) is a counting step, in which the number of fluorescent particles of the extracted set luminance value or more is counted (only the number of fluorescent particles of the red (broken line) is calculated).

Fluorescence Image Acquisition Process

Here, it is possible to refer to a technique in which excitation light is irradiated to fragmented DNA captured on the plasmon metal nanocrystal substrate, autofluorescence of the captured fragmented DNA is enhanced by a surface plasmon enhancement effect, and a fluorescent colony is acquired as a fluorescent image (Japanese Patent Application No. 2019-234330).

Example 4

In addition, a solution obtained by mixing an Ag reagent (2000 ppm, 411) for producing quantum crystals and a H1N1 influenza virus antibody (250 μg/ml, 5 μl) imparted with a FITC label in the same manner is prepared and dropped into a phosphor bronze plate, and a H1N1 influenza virus antibody imparted with a FITC label to a quantum crystal to be purified on a substrate is solidified.

Fluorescence of FITC on the grains was observed when this solid-phase substrate was observed by fluorescence microscopy.

Thus, a fluorescent label such as FITC can be put into a solid phase on the quantum-crystal substrate. Wherein the Ag-reagent has a range from 500 ppm to 10000 ppm, preferably from 1000 to 5000, more preferably from 2000 to 4000 ppm, and H1N1 influenza virus-antibody imparted with a FITC label that solidifies has a range from 1 pg/ml to 1 g/ml).

Measurement Example 1

Surface plasmon-excited enhanced fluorescent spectroscopy (SPFS) methods are applied to detect viruses in patients using pharyngeal swabs, saliva, urine, and feces in the presence of viral antigens.

FIG. 1 is a process comprising of steps (1) to (4).

In step (1), an antibody solid-phase substrate is prepared using a quantum crystal aggregation method.

More specifically, viral antibodies are added to a buffer (pH7 phosphate buffer) to generate a solid-phase antibody solution.

To this is added in an equal amount of an aqueous plasmon metal complex solution having a concentration of 1000 to 10000, preferably 2000 to 4000 ppm, and a complex aqueous solution of a plasmon metal complex and a virus antibody is adjusted, and a plasmon metal complex solution containing a virus antibody is dropped onto a metal substrate having an electrode potential near a reduction potential of a plasmon metal complex to aggregate plasmon metal complex quantum crystals to which an antibody is bound, thereby preparing a virus antibody solidified substrate in which a virus antibody is solidified.

Here, one kind selected from palladium, platinum, gold, silver, and copper is selected as the plasmon metal, a metal substrate having an electrode potential in the vicinity of the oxidation-reduction potential of the plasmon metal complex is selected, and copper or a copper alloy, in particular, phosphor bronze is selected as the substrate when the quantum crystal of the silver thiosulfate complex is used.

Here, the antibodies include, as influenza virus antibodies, monoclonal antibodies of the five classes of IgA, IgD, IgE, IgG, and IgM of animal species such as rats, mice, chickens, rabbits, and humans produced from viral antigens and hybridomas, polyclonal antibodies including the five classes of IgA, IgD, IgE, IgG, and IgM of animal species such as rabbits, guinea pigs, goats, sheep, rats, mice, and chickens, and immunoglobulins, Fc regions and Fab regions, heavy chains, light chains, antigen binding sites, fragmented antibodies such as fragmented portions of hinge regions, and human B lymphocytes obtained by cloning human antibodies (e.g., EBV) obtained by infecting human antibodies.

Examples of the coronavirus antibody include monoclonal antibodies of the five classes IgA, IgD, IgE, IgG, and IgM of animal species such as rats, mice, chickens, rabbits, and humans produced from viral antigens and hybridomas, polyclonal antibodies including the five classes IgA, IgD, IgE, IgG, and IgM of animal species such as guinea pigs, goats, sheep, rats, mice, and chickens, antibodies such as immunoglobulins, Fc regions and Fab regions, fragmented antibodies such as heavy and light chains, antigen binding sites and hinge regions, reconstituted antibodies, cross-sectioned portions of antibodies, and human B lymphocytes obtained by cloning human antibodies (such as EBV).

In step (2), an antigen-antibody reaction is utilized to form a complex of a virus antibody labeled with a fluorescent substance and a virus antigen in a sample.

Here, as a sample, throat wipe, saliva, urine, and feces are used as objects.

Fluorescent substances that label viral antibodies can include excitation light, such as Pacific Blue, from 400 nm to 436 nm; excitation light, such as FITC, from 453 to 505 nm; excitation light, such as TRITC, from 485 to 566 nm;

excitation light, such as APC, from 488 to 706 nm; and excitation light, such as IRDye800, from 732 to 784 nm.

In the process (3), the above complex is dropped onto the above-mentioned antibody-solidified substrate using an antigen-antibody reaction, and the complex is bound to an antibody on the substrate, and the unbound complex and the antibody are washed with pure water, a buffer, or the like.

Here, a phosphate buffer in the neutral range was used as a buffer, but PBS, HEPES, TRIS, BIS-TRIS, CAPS, CAPSO, Glycylglycine, MES, MOPS, PIPES, and the like are utilized.

In step (4), excitation light is irradiated to the complex of the labeled antibody and the antigen remaining on the substrate, the fluorescence image is observed by surface plasmon excitation with a fluorescence microscope or a fluorescence reader, and particles of fluorescence having a luminance value equal to or higher than an arbitrary value are binarized from an arbitrary range of the obtained fluorescence image or from the whole image, and the number obtained is counted.

Since the fluorescence measurement method of the same applicant's Patent Application No. 2019-234330 can be used to binarize and count the grains of fluorescence having a certain threshold value or more in the fluorescence image, such a fluorescence measurement method is cited and referred to here.

In the present invention, 1 field measurement condition shown in FIG. 16: Threshold 62 no blur filter 1 field measurement of a 10× lens without blur filter 1 field measurement (here, 1 field measurement refers to a method of acquiring only one part of the chip unlike the case of Special Application 2019-234330 as shown in FIG. 16. Since the 1 field measurement when using the solid-phased substrate according to the present invention is roughly equivalent to the average value of 1 field measurement of 2 or more, it has been found that the result of 1 field measurement can be used without employing an average value. It is determined that the solid phase of the antigens or the antigens is roughly uniformly formed by the quantum crystals).

In the above example, a substrate in which an antibody is solidified is used, but a viral antigen can be detected by utilizing an antigen-antibody reaction in a liquid by using a metal powder of the same kind.

The pharyngeal swab, saliva, urine, and faeces containing viral antigens are used, and in FIG. 2 they consist of steps (1) to (5).

In step (1), an antibody solid-phase metal powder is produced using a quantum crystal aggregation method.

Specifically, virus antibodies are added to aqueous plasmonic metal complexes at concentrations of 500-10000 ppm, and carrier metal powders are added to the complexes and mixed.

The plasmonic metal complex together with the virus antibody aggregates with the metal powder having an electrode potential near the reduction potential of the plasmonic metal complex to form a virus antibody solidified metal powder in which the virus antibody, the plasmonic metal complex, and the carrier metal powder are integrated.

On the other hand, in step (2), a complex of a virus antibody labeled with a fluorescent substance and a virus antigen in a sample is formed using a first antigen antibody reaction.

Here, the analyte and the fluorescent material are the same as those of the first method.

Then, in step (3), the above complex is added into the antibody solidified powder liquid, and a second antigen antibody reaction is utilized to bind the antibody solidified powder and the above complex.

In step (4), a coalescence of an antibody solidified powder and a complex is filtered, and the unbound complex and the antibody are washed with pure water, a buffer, or the like.

Finally, in step (5), the labeled antibody-antigen complex remaining on the substrate is irradiated with excitation light, the fluorescence image thereof is observed by surface plasmon excitation with a fluorescence microscope or a fluorescence reader, and particles of fluorescence having a luminance value equal to or higher than an arbitrary value are binarized from an arbitrary range of the obtained fluorescence image or from the entire image, and the number obtained is counted.

Figure 3:
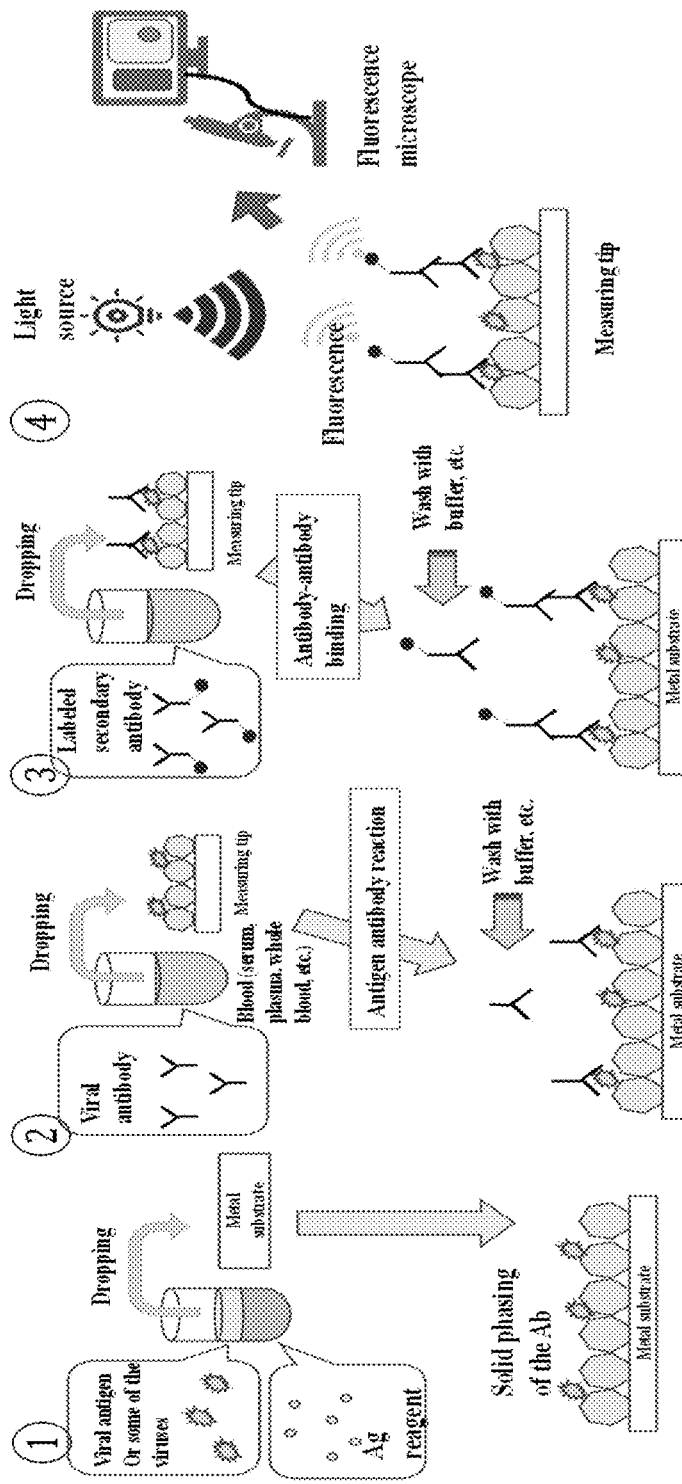
FIG. 3 shows a schematic diagram of Antigen-Antibody Reaction Using Quantum Crystals (Indirect Method). It comprises of steps (1) to (4) when a second method (indirect method) is used for the fluorescent labeling step of the present invention. In step (1), an Ag reagent and a part of a viral antigen or a virus are mixed and dropped onto a metal substrate, and the antigen is solidified by aggregation of quantum crystals formed on a metal substrate. In the step (2), when a blood containing an antibody against a viral antigen or a part of a virus is dripped, the antigen on the substrate and the antibody in the blood are bound by the antigen-antibody reaction. In step (3), when the labeled secondary antibody is dropped into the measurement chip, the antibody on the substrate and the labeled secondary antibody bind. The unbound labeled secondary antibody is washed off with buffer or the like. Here, an antibody that binds to an antibody is referred to as a secondary antibody. In step (4), light of a light source matching the label (fluorescent substance) of the secondary antibody is irradiated to excite, and the label is fluorescent. This is detected by fluorescence microscopy.

The second method of the present invention is a method of solidifying a viral antigen or a part thereof (a part of a non-infectious antigen, e.g., a fragmented part of a viral surface spike or a viral nucleocapsid) into a solid phase and capturing an antibody generated in the body, and as shown in FIG. 3, a method of solidifying an antigen or a part thereof by using the quantum crystal aggregation method of a plasmon metal complex and then reacting the antigen or a part thereof with an antibody to form an antigen having a gap or a micro-channel between quantum crystals or a partially solidified-phased substrate thereof, while dropping an antibody labeled by using a fluorescent substance to the antigen or a partially solidified substrate to bind the antigen and washing the unbound labeled antibody, and then irradiating the labeled antibody remaining on the substrate with excitation light to excite the quantum crystal to enhance the fluorescence of the labeled antibody, thereby detecting the fluorescence of the labeled antibody.

An antigen or a part thereof is solidified using a quantum crystal aggregation method of a plasmonic metal complex, and then an antigen or a part thereof and an antibody are reacted with each other to form an antigen or a partially solidified substrate comprising a gap or a microchannel between quantum crystals, and a labeled antibody labeled using a fluorescent substance is dropped onto the antigen or a partially solidified substrate to bind them, and the unbound labeled antibody is washed, and then the labeled antibody remaining on the substrate is irradiated with excitation light to excite the quantum crystals by surface plasmon excitation, and the fluorescence image is observed by a fluorescence microscope or a fluorescence reader, and the obtained fluorescence image is subjected to binarization of the particles of fluorescence having a luminance value equal to or higher than an arbitrary value from an arbitrary range or an entire image of the obtained fluorescence image, and the obtained number is counted and detected.

In other words, in step (1), an antigen and a partially solidified substrate thereof are prepared using a quantum crystal aggregation method.

More particularly, viral antigens and some of them are added to aqueous plasmonic metal complexes at concentrations of 500-10000 ppm.

Some of the viral antigens and some of them, such as pharyngeal swabs, saliva, urine, feces, and noninfectious antigens, are used.

Viral antigens and some of them can be treated by autoclaving (autoclaving at 121° C. for 15 minutes or more), soaking in Na hypochlorite at 0.01% or more for 1 hour or more, soaking in 4% formaldehyde solution or soaking in 70% ethanol, and so on.

A complex aqueous solution of a plasmon metal complex and a viral antigen or a part thereof is prepared, and a plasmon metal complex solution containing a viral antigen or a part thereof is dropped onto a metal substrate having an electrode potential in the vicinity of a reduction potential of the plasmon metal complex, and a plasmon metal complex quantum crystal to which an antigen or a part thereof is bound is aggregated to prepare a viral antigen or a part thereof which is made into a solid phase, or a partly solid phase substrate.

Then, in step (2), the first antigen antibody reaction is utilized to form a complex of a solid-phased antigen and a portion thereof with a virus antibody in blood.

Here, blood, serum, and plasma are used as samples containing viral antibodies.

In step (3), a labeled antibody is prepared, and the labeled antibody is dropped onto an antigen antibody solidified substrate using a second antigen antibody reaction, and the complex is bound to an antibody on the substrate, and the unbound labeled antibody is washed with pure water, a buffer, or the like.

However, it is also possible to mix the sample of step (2) with the labeled antibody of step (3) in advance.

In step (4), excitation light is irradiated to the complex of the labeled antibody and the antigen remaining on the substrate, the fluorescence image is observed by surface plasmon excitation with a fluorescence microscope or a fluorescence reader, and particles of fluorescence having a luminance value equal to or higher than an arbitrary value are binarized within an arbitrary range of the obtained fluorescence image or from the entire image, and the obtained number is counted and detected.

In the above sandwich method, as a labeled antibody, a primary labeled antibody capable of binding to each other and a secondary labeled antibody are simultaneously used to enhance fluorescence intensity.

The method of FIG. 4 uses simultaneously a primary labeled antibody and a secondary labeled antibody capable of binding to each other in the steps of the first method (1) to (4) of the present invention.

Figure 17:
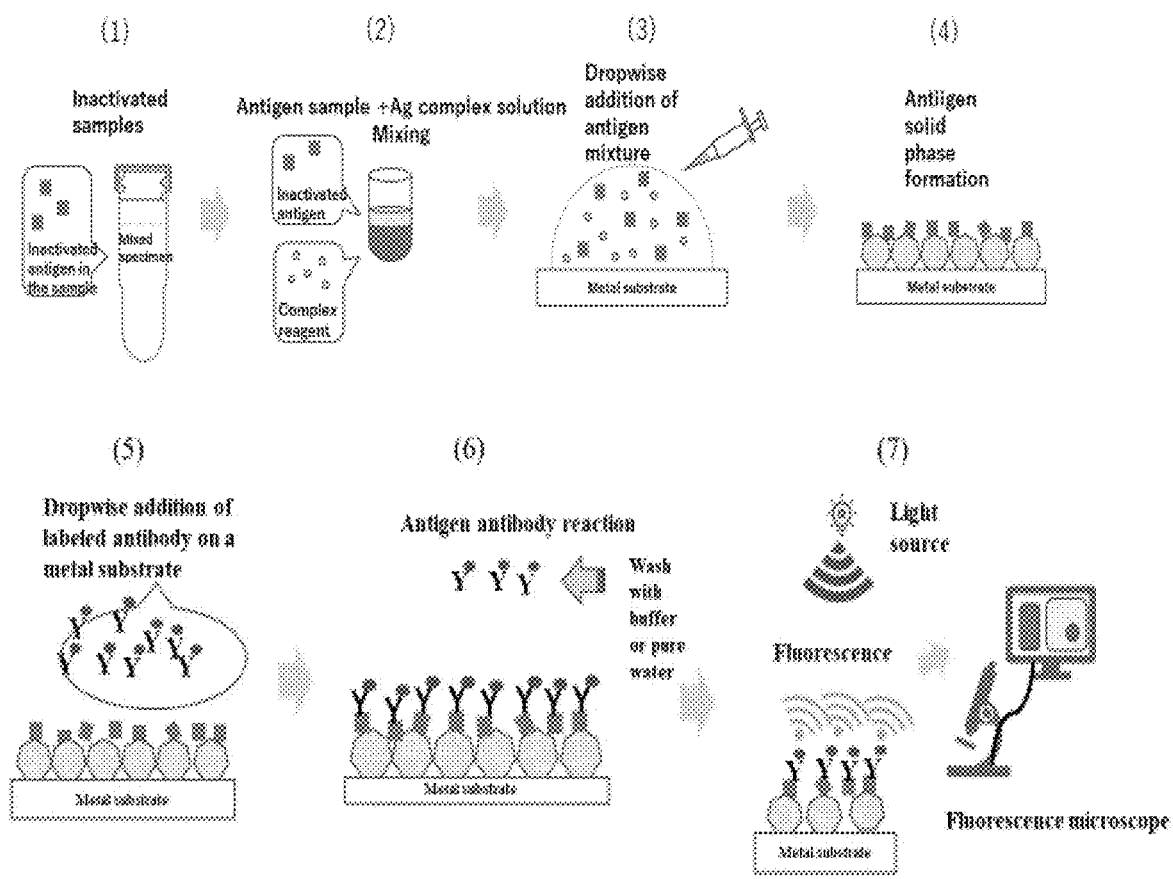

In step (1), an antibody solid-phase substrate is prepared using a quantum crystal aggregation method. This is the same as the step (1) of FIG. 17.

In step (2), a first labeled antibody and a second labeled antibody are simultaneously used as a virus antibody labeled with a fluorescent substance using an antigen-antibody reaction to form a complex with a virus antigen in a sample. or a secondary labeled antibody may be conjugated after binding the primary labeled antibody.

Here, as a sample, throat wipe, saliva, urine, and feces are used as objects.

Fluorescent substances that label viral antibodies can include excitation light, such as Pacific Blue, from 400 nm to 436 nm; excitation light, such as FITC, from 453 to 505 nm; excitation light, such as TRITC, from 485 to 566 nm; excitation light, such as APC, from 488 to 706 nm; and excitation light, such as IRDye800, from 732 to 784 nm.

As a combination of primary and secondary labeled antibodies, a secondary labeled antibody that recognizes the species from which the primary labeled antibody is derived is combined.

For example, when a primary labeled antibody from a mouse is used, a secondary labeled antibody that recognizes a mouse antibody is used and is similarly combined in other animal species.

In step (3), the above complex is dropped onto the above-mentioned antibody solidified substrate using an antigen-antibody reaction, and the complex is bound to an antibody on the substrate, and the unbound complex and the antibody are washed with pure water, a buffer, or the like.

Here, PBS, HEPES, TRIS, BIS-TRIS, CAPS, CAPSO, Glycylglycine, MES, MOPS, PIPES, and the like are utilized as buffers.

In step (4), excitation light is irradiated to the complex of the labeled antibody and the antigen remaining on the substrate, the fluorescence image is observed by surface plasmon excitation with a fluorescence microscope or a fluorescence reader, and particles of fluorescence having a luminance value equal to or higher than an arbitrary value are binarized from an arbitrary range of the obtained fluorescence image or from the whole image, and the number obtained is counted.

(Actual Measurement by Antigen-Antibody Reaction of Influenza Virus)

Equal amounts of Ag reagent (500-10000 ppm) and influenza antibody (5-1000 µg/ml), which are the origin of the quantum crystals, are mixed, and the mixed liquid is dropped onto a phosphor bronze plate to solidify the quantum crystals and antibodies onto a phosphor bronze plate.

Influenza virus (5-1000 µg/ml) and FITC labeled influenza antibody (5-1000 µg/ml) are then mixed in equal amounts and dropped onto the unfolded quantum crystal substrates.

As an example of reagents: Influenza HyTest's Monoclonal mouse anti-Influenza A haemagglutinin H1, Influenza virus HyTest's Influenza A (H1N1) Virus, FITC Influenza Antibodies IBL Anti-Influenza A Virus(H1N1) FITC was used.

The influenza antibody with excess FITC label is washed with pure water or the like, and is irradiated with light from a light source (metal halide lamp 80 W) and measured using a fluorescence microscope (fluorescence microscope BZ-X710 by Keyence)

Images were observed by fluorescent microscopy and analyzed by BZ-X Analyer. This is as shown in FIG. 6(a). In contrast, the case where the influenza antigen is not included is as shown in FIG. 6(b).

The surface plasmon is excited and the fluorescence image is observed by a fluorescence microscope or a fluorescence reader, and the obtained number is counted and detected by binarizing the particles of fluorescence having a luminance value equal to or higher than a luminance value of an arbitrary value from an arbitrary range of the obtained fluorescence image or from the entire image.

When the virus was present, it was sandwiched between the solid-phase antibody on the quantum crystal and the antibody labeled, and a large number of fluorescence was emitted in a granular form, and it was observed that the fluorescence of this granular fluorescence is the fluorescence of the labeled antibody sandwiched between the virus (FIG. 6(a)), whereas in the absence of virus, a large number of fluorescence in the granular form did not appear (FIG. 6(b)).

Figure 7:
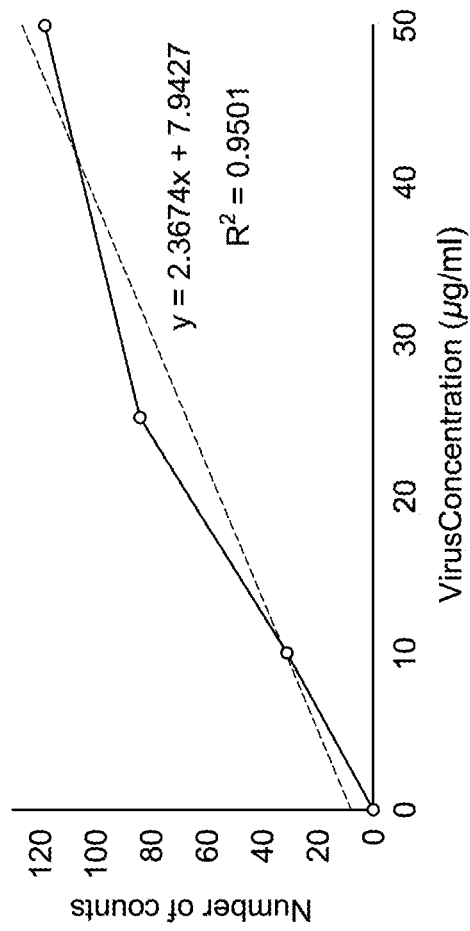
FIG. 7 shows a graph when the quantitation of influenza virus is performed by the fluorescence count number of the present invention. Here, the count number * refers to a count number obtained by binarizing a brightness value equal to or greater than the threshold value 57 by the analysis software "BZ-X Analyzer" from the obtained images. The blank (Virus level 0 μg/ml) was calculated as counting 0.

Virus (Virus) concentration and brightness value 57 or more of the grain of fluorescence in the fluorescence image were binarized with an influenza antibody (25 µg/ml) and an FITC influenza antibody (25 µg/ml) at a keyence BZ-X710 objective×10 magnification using an analysis software (BZ-X) and counted, and the result of the table shown in FIG. 7 was obtained.

This is linearized in the graph of FIG. 7.

From the obtained image, it can be seen that the count number and the virus concentration have a relative relationship.

(Inspection of On-Site Samples)

The present invention is suitable for an immigration examination and a method of rapidly conducting a virus examination on the spot at the time of diagnosis of a hospital, and is characterized in that after an antigen in a sample (pharyngeal swab, saliva, sputum, nasopharyngeal fluid, urine, etc.) collected from a human is inactivated, the inactivated antigen is solidified on the substrate by a quantum crystal aggregation method, the antibody labeled on the solidified antigen is bound by an antigen-antibody reaction and labeled, and then the unbound labeled antibody is washed with a buffer solution or pure water, the excitation light for the labeling of the antibody (fluorescent substance) is irradiated from a light source, and the fluorescent particles on the substrate are counted by a fluorescent microscope.

Here, the quantum crystal flocculation method refers to the flocculation method that produces the quantum crystals of the plasmon metal complex shown in Special Application No. 2016-197114, whereby the plasmon metal complex in the solution is flocculated as a quantum crystals of the metal complex on the metal substrates with the electric potential near the reduced potential, depending on the selection of the electro-deposited board potential.

In this case, on a substrate in which an antibody is previously solidified by a quantum crystal aggregation method, an antigen in a collected sample is inactivated and bound to a substrate by an antigen-antibody reaction, and a label is bound by an antibody labeled with an antigen-antibody reaction to be labeled, and then an unbound labeled antibody is washed with a buffer or pure water, and excitation light meeting a label of an antibody (fluorescent substance) is irradiated from a light source, and fluorescent particles on the substrate are counted by a fluorescence microscope.

(Inactivation of Samples)

In the present invention, a virus to be inactivated in a sample is basically composed of either nucleic acid DNA or RNA and a shell protein (capsid) protecting the same, and is classified into a small spherical virus having no envelope and a case in which the virus is wrapped by a membrane called an envelope containing a lipid.

Thus, while the difference in susceptibility to inactivation by a drug depends on whether it has an envelope, the use of a drug is preferred because generally enveloped viruses are sensitive to disinfectants.

Other inactivation methods that are effective against most viruses include boiling (above 98° C.) for 15-20 min, 2 w glutaral/v %, 0.05-0.5 w per v % (500-5000 ppm) sodium hypochlorite, 76.9-81.4 v per v % disinfectant ethanol, 70 v/v % isopropanol. 2.5 w per v % povidone-iodine. 55 w/v % phthalal, and 0.3 w per v % peracetic acid.

Many viruses are inactivated by alteration of capsid proteins at 56° C. for 30 minutes, and enveloped viruses are easily inactivated by lipid solvents such as ether, chloroform, and fluorocarbons.

In addition, by using an antibody which recognizes a nucleoside, a nucleotide, or a nucleocapsid present inside a virus, it is possible to detect an inactivated viral antigen which is finely divided by destroying a membrane or a shell.

Therefore, as the inactivation according to the present invention, from the viewpoint of not affecting or little affecting the antigen-antibody reaction, a medicine method using ethanol, formalin, or AVL buffer and an inactivation method such as heat treatment, SD treatment (chemical treatment), acidic treatment, alkali treatment, or radiation treatment can be used.

In the present invention, a metal powder may be used instead of a substrate.

In addition, in the above method, when a primary antibody having a fluorescent label and a antibody having a fluorescent label are simultaneously used as a labeled antibody and imaged and analyzed, a more fluorescent image can be acquired appropriately and accurately.

The present invention preferably uses a specimen inactivation collection kit to be applicable to on-site collection, on-site inspection, and may be inactivated using an agent.

Figure 18:
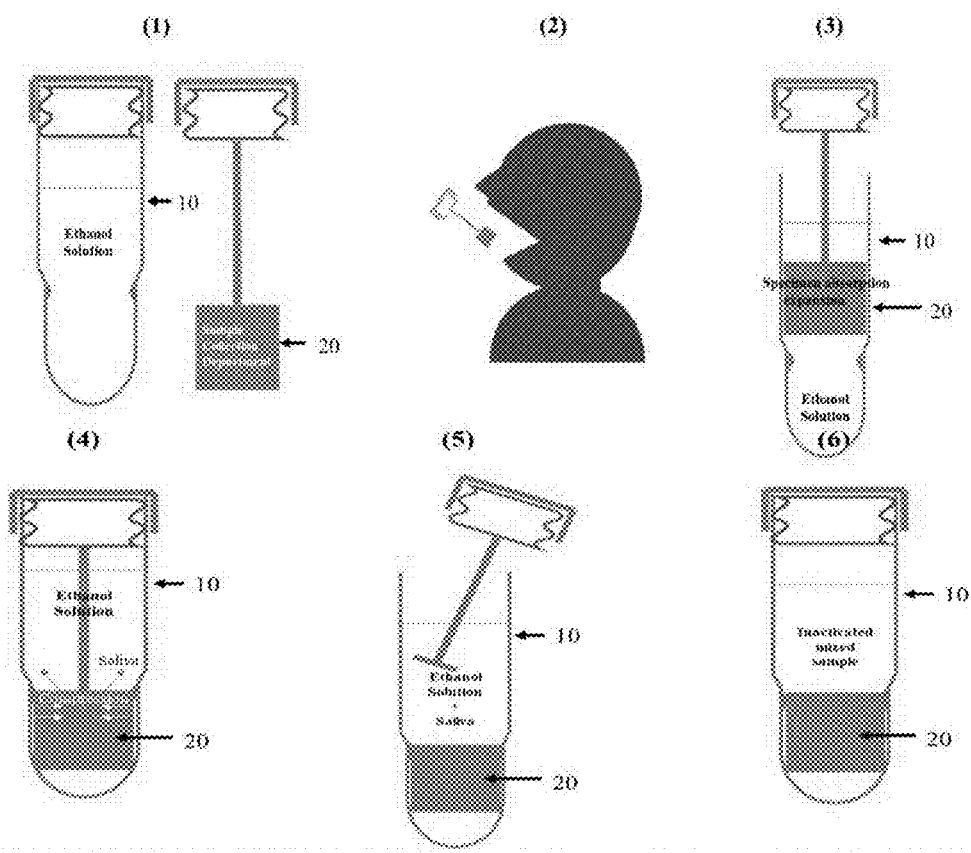

As shown in FIG. 18, a tube 10 containing a chemical agent L such as ethanol and a rod-shaped sample collection unit 20 are set, and the sample collection unit is configured to have an absorption performance such as a nonwoven fabric or a gauze. Samples are then collected at the (2) rod-shaped sample collection section. Saliva, sputum, pharyngeal swab, nasopharyngeal fluid, etc. are used as sample S. (3) After the sample S is collected, the collection portion 20 is placed in the tube 10. In FIG. 18 (4) The inside of the tube 10 becomes a narrow portion, and when the sample collection portion 20 is inserted, the sample collection portion 20 is compressed on the narrow wall surface, and the sample S (saliva) is dispersed in the chemical liquid L such as ethanol. (5) When a portion other than the sample collection portion 20 is removed, the sample collection portion 20 remains in the tube 10. (6) The sample S is inactivated by the drug L and remains in the sample collection section 20.

According to the present invention, viral antigens are collected and inactivated in the field, and immobilized on a substrate by a quantum crystal agglutination method to bind labeled antibodies, or the viral antigens inactivated by an antigen-antibody reaction and labeled antibodies are bound on a substrate on which antibodies have been immobilized in advance, and the number of fluorescence of the viral antigens is counted instead of the fluorescence intensity thereof, and the virus concentration can be measured.

In addition, since the quantum crystal forming the antibody or the antigen-solidified substrate interacts between the photon incident by the excitation light and the free electron of the plasmon metal particle forming the quantum crystal, and the surface plasmon is excited to enhance the fluorescence of the labeled antibody, the fluorescence of the particle can be counted and detected with good reproducibility instead of the entire fluorescence intensity.

Thus, surface-plasmon-enhanced fluorescence spectroscopy (SPFS) can be used to quickly test in as short as 2-5 minutes, providing accurate diagnostic results that replace PCR-testing, which is cumbersome to preprocess, less sensitive with primers, more protocol, and more time-consuming to test.

In addition, since the count number corresponds to the number of viruses as well as the determination of the presence or absence of the disease, the determination of the mild severity of the disease can be made, which is epoch-making.

According to the sample inactivation collection kit of the present invention, since the collected virus can be inactivated and secured in the tube, it can be sent to a necessary inspection site and can be taken out and inspected at any time.

In the present invention, an inactivated antigen or the like is directly solidified by a quantum crystal aggregation method, but an antibody is previously solidified, and an antibody obtained by labeling an inactivated antigen with an antigen-antibody reaction may be bound and detected, and a direct method, a sandwich method, and an indirect method in a fluorescent antibody method may be employed.

(Detection of Virus from Inactive Specimens)

An equal volume of Ag reagent (2000 ppm, 12.5 µl) and hemagglutinin H1 influenza A antibody (25 µg/ml, 12.5 µl)

for producing quantum crystals were prepared and dropped onto a phosphor bronze plate and aggregated on a substrate.

The hemagglutinin H1 influenza A antimony is solidified together with the quantum crystals.

Next, a complex of the inactivated analyte (25 μg/ml, 5 μl) and H1N1 influenza virus antibody (25 μg/ml, 5 μl) to which FITC label has been applied is dropped onto the solid phase substrate of the hemagglutinin H1 influenza A antibody.

When H1N1 influenza virus was present in the inactivated sample, the complex of the influenza virus and FITC labeling antibody bound to the solid-phased antibody on the solid-phased substrate, and the fluorescence of FITC on the particle was observed by fluorescence microscopy.

In addition, when the influenza virus was not present in the sample, no fluorescent light of FITC on the grains was observed.

When the measured images obtained by fluorescence microscopy were set to the thresholds 57 by the "Keyence Analysis Software: BZ-X Analyzer" and analyzed, large differences were obtained in the fluorescence counts of the granular FITC.

As a result, when the number of fluorescent particles from the fluorescent image was counted, it was 4 in the absence of virus, whereas it was 145 in the presence of virus.

The equipment used is as follows. Instrument: Keyence Fluorescent Microscopy BZ-Z710, Light source: Metal halide lamp 80 W, Fluorescent filter: BZ-X filter GFP (525±25), Analysis software: BZ-X Analyzer.

(Measurement Example 1 of Patient Virus)

The fluorescence counting method of the present invention is applied to detection of a virus of a patient, and a pharyngeal swab, saliva, sputum, nasopharyngeal fluid, urine, or feces in which a virus antigen is present is used.

FIG. 17 is a method comprising of steps (1) to (7).

In step (1), an inactivated sample is generated using the sample inactivation collection kit shown in FIG. 18.

In step (2), the inactivated antigen and the Ag reagent (silver thiosulfate complex solution) in the sample are mixed.

In step (3), a solid-phase substrate of an inactivated antigen is prepared using a quantum crystal aggregation method.

Specifically, an inactivated antigen is added into an aqueous plasmon metal complex solution having a concentration of 2000 to 6000 ppm, and a complex aqueous solution of a plasmon metal complex and an inactivated antigen is adjusted, and a plasmon metal complex solution containing an inactivated antigen is dropped onto a metal substrate having an electrode potential near the reduction potential of the plasmon metal complex to aggregate the plasmon metal complex quantum crystals to solidify the inactivated antigen (Step (4))

Here, one kind selected from palladium, platinum, gold, silver, and copper is selected as the plasmon metal, a metal substrate having an electrode potential in the vicinity of the oxidation-reduction potential of the plasmon metal complex is selected, and copper or a copper alloy, in particular, phosphor bronze is selected as the substrate when the quantum crystal of the silver thiosulfate complex is used.

The preparation method of the quantum crystal method described in JP-A-2016-197114 is cited and referenced.

In step (5), a virus antibody labeled with a fluorescent substance using an antigen-antibody reaction is used to label a virus antigen in a solid-phase sample.

Here, as the sample, pharyngeal swab, saliva, sputum, nasopharyngeal fluid, urine, and feces are targeted.

Fluorescent substances that label viral antibodies can include excitation light, such as Pacific Blue, from 400 nm to 436 nm; excitation light, such as FITC, from 453 to 505 nm; excitation light, such as TRITC, from 485 to 566 nm; excitation light, such as APC, from 488 to 706 nm; and excitation light, such as IRDye800, from 732 to 784 nm.

In step (6), unbound complexes and antibodies are washed from the substrate with pure water, buffer, or the like.

Here, in addition to neutral phosphate buffer as a buffer, PBS, HEPES, TRIS, BIS-TRIS, CAPS, CAPSO, Glycylglycine, MES, MOPS, PIPES, and the like can be utilized.

In step (7), excitation light is irradiated to the complex of the labeled antibody and the antigen remaining on the substrate, the fluorescence image is observed by surface plasmon excitation with a fluorescence microscope or a fluorescence reader, and particles of fluorescence having a luminance value equal to or higher than an arbitrary value are binarized from an arbitrary range of the obtained fluorescence image or from the entire image, and the number obtained is counted.

Grains of fluorescence above a certain threshold in the fluorescence image are binarized and counted.

According to the method of the present invention, detection of viruses with high precision comparable to the PCR method can be easily and quickly performed.

Therefore, an immigration inspection, a rapid inspection at a hospital, etc. in the field are possible.

(Detection of Two Viruses)

The following method is described as a measurement method for detecting two types of viruses by one measurement chip.

1) A mixture of an influenza antibody (containing a plurality of antibodies as an influenza antibody) buffer and a coronavirus (Covid-19) antibody buffer is mixed in equal amounts into the Ag reagent (3000 ppm of an aqueous solution of silver thiosulfate), and finally a solid phase sample containing 1000 ppm of Ag reagent is adjusted.

or, the three shall be mixed in equal amounts in order to make an adjustment.

The mixed liquid is dropped onto a metal substrate to create a solidified substrate (see FIG. 19A (1)).

2) Next, mix a sample (e.g., pharyngeal swab or saliva) collected from a human inactivated with ethanol or the like with a mixture of green-labeled corona antibody and red-labeled influenza antibody.

If either virus is present in the sample, the virus forms a complex with the labeled antibody. Then, the composite is dropped onto a solidified substrate. 3) The complex binds to an antibody that is solidified on the substrate by an antigen-antibody reaction (see FIG. 19A (2)).

Complexes or labeled antibodies that are bound are washed off with water or buffer (see FIG. 19B (3)).

Here, labeling of the corona antibody is performed with labeling of green regions such as FITC and Cy2, and labeling of red regions such as Cy5 and APCs is performed with labeling of influenza antibodies, and the respective fluorescent regions are selected so as not to overlap with each other. The light source is irradiated with green wavelength excitation light and red wavelength excitation light, respectively.

When influenza virus is present in the sample, no fluorescence is observed in the green excitation, but fluorescence is observed from the red-labeled influenza antibody in the red excitation.

On the other hand, when coronavirus is present in the sample, no fluorescence is observed in red excitation, but fluorescence is observed from the green-labeled corona antibody in green excitation (see FIG. 19B (4)).

In this manner, two fluorescence images obtained from the two excitation lights are acquired by a fluorescence microscope, and the fluorescence spots or grains on the images are counted and quantified. Filters in the green region: excitation wavelength 470±20 nm, fluorescence wavelength 525±25 nm. The filter in the red region was set to an excitation wavelength of 620±20 nm and a fluorescence wavelength of 700±37.5 nm.

(pH Effect of Quantum Crystal Aggregation: Example)

Then, antibodies adjusted with three buffers (PBS) of pH6.0, 7.4, and 8.0 are mixed into the quantum crystalline reagent to solidify the antibody by changing the pH at which the quantum crystals are generated.

The grains of light of the fluorescently labeled antibody bound by the antigen-antibody reaction are counted to measure the state of the quantum crystal formed at the respective pH (the state of the solid-phase substrate) and the count value.

Using a quantum crystalline reagent, an inactivated influenza virus is added dropwise to a substrate in which an influenza antibody diluted in PBS buffer (pH6.0, pH7.4, pH8.0) is solidified together with a quantum crystal, and a fluorescent point is counted from the obtained fluorescent image.

To 2000 ppm of an aqueous solution of silver thiosulfate (Ag-reagent), an equal amount of influenza antibody (diluted with 50 μg/ml, 0.1 mol/L, phosphate buffer pH6.0, 7.4, and 8.0) is mixed and dropped onto a phosphor bronze substrate to prepare an antibody-solidified substrate.

Complexes formed by mixing inactivated influenza virus (10 μg/ml) with FITC labeled influenza antibody (10 μg/ml) are dropped onto a solid-phase substrate (reaction time 1 min).

Unbound complexes or FITC are washed away with water or buffer.

The chips are measured with a Keyence fluorescence microscope "BZ-X710" and the fluorescence points above predetermined thresholds of the obtained fluorescence images are counted.

Consequently, the counted values of labeled antibodies by antigen-antibody reaction of quantum crystals generated in a buffer solution of pH6.0 showed Buffer (blank): count value 3 (relative value 0), and influenza virus: count number 31 (relative value 28) (see FIG. 20B)

Next, the count value of the labeled antibody by the antigen-antibody reaction of the quantum crystals generated in the buffer of pH74 showed a Buffer (blank): a count value of 4 (relative value of 0), and an influenza virus: a count number of 64 (relative value of 60)

In addition, the count value of the labeled antibody by the antigen-antibody reaction of the quantum crystal generated in the buffer of pH8.0 showed a Buffer (blank): a count value of 4 (relative value of 0), and an influenza virus: a count number of 57 (relative value of 53) (see FIG. 20B). The relative value is the count number when the count number of blanks is set to 0.

From this, it is considered that the antibody solidified quantum crystal produced by the buffer solution of pH6.4 is the same as the quantum crystal produced by pH6 degree without adding anything (FIG. 20A (a)), and since the three-dimensional and stacked quantum crystal is produced on the substrate, the antibodies are gathered and solidified on the substrate, and the count values of the fluorescent labels by the antigen-antibody reactions are small.

It is considered that the quantum crystals solidified by the buffer solution of polygon, pH7.4, and 8.0 were solidified by the buffer solution of pH7.4 (FIG. 20A (b)), and the crystals on fine grains dispersed over the substrate were formed on the substrate, and the antibodies were also dispersed and solidified on the substrate, and the counted values of fluorescent labels by the antigen-antibody reactions increased.

When an antibody-immobilized substrate based on quantum crystals is used as an inspection method for detecting viruses, if the antibody is immobilized with a quantum crystal reagent whose pH is adjusted to 7 to 8 by an added buffer solution, quantum crystals are generated on fine grains dispersed over the surface of the substrate, and the antibody is immobilized on the finely dispersed quantum crystals, so that a larger count value can be detected and a virus detection method with high sensitivity can be used.

Reagents: Influenza antibodies: Hytest "Monoclonal Mouse anti-influenza A haemogglutinin H1"CatNo. 3AH1", FITC Influenza (ARP. Anti-Influenza A virus(H1N1)FITC") CatNo.)12-6250-3, Influenza virus: HyTest "Influenza A(H1N1)virus"CatNo. IN73-3"

Equipment: Keyence "BZ-X71"

(Automated System for Performing Fluorescence Counting Assays of the Invention)

The automated system of the present invention comprises a pretreatment automation device (A) and a fluorescence image counting automation device (B) as shown in FIG. 8A.

The pretreatment automation device (A) comprises a solid phase or immobilization process comprising of the following (1), (3), and (4) steps, a labeling process comprising of (2) and (5) steps, and a cleaning process comprising of (6) step.

On the other hand, the fluorescence image counting automation apparatus 'B) comprises a fluorescence excitation step comprising (7) and a fluorescence image counting step comprising (8).

Here, in the first step (1), a solid phase subject (virus antigen or antibody) referred to in the present invention is mixed with an Ag reagent (typically referred to as an aqueous solution of silver thiosulfate of 1000 to 5000 ppm) to prepare a phase solidifying liquor or immobilizing solution.

In the second step (2), a labeling liquor for labeling a virus or an antibody to be measured is mixed with fluorescence.

In the 3rd step (3), the phase solidifying liquor prepared in the first step is dropped onto the metal substrate, and the antibody or antigen in the phase solidifying liquor is solidified on the metal substrate by aggregation of the Ag complex in the Ag regent.

In the fourth step (4), the phase solidifying liquor dropped onto the metal substrate continues to be coagulated by the electrode potential difference with respect to the metal substrate, and this coagulation reaction is blown off by air blowing, thereby stopping in a state of a phase solidified or immobilized layer appropriate for the measurement substrate.

In the fifth step (5), the labeling liquor prepared in the $2^{nd}$ step is dropped into the solid phase layer prepared in the 4th step to label the virus or antibody to be measured with an antigen-antibody reaction.

A general method employed in this field can be employed for labeling, and it is needless to say that the above-described sandwich method, the direct method, or the indirect method can be used, but each method includes a sensitization method such as a typical method (ABC method) in which a primary antibody (or a secondary antibody) is biotinylated and a biotin-avidin complex is formed and detected. In the case of the present invention, the labeling rate is determined in consideration of the surface plasmon enhancement effect of the quantum crystal.

In the 6th step (6), the unreacted labeling liquor remaining on the labeled solid phase layer is washed out and washed away to reduce the cause of measurement error.

In the seventh step (7), an excitation light is irradiated to the labeled object (virus or antibody) on the measurement chip to emit fluorescence light and the fluorescence is also excited, and a fluorescence image having the excited fluorescence points can be observed by a fluorescence microscope.

In the 8th step (8), since there are observed fluorescent points corresponding to the labeled object and some fluorescent points which becomes a measurement error in the fluorescent image, in order to distinguish the fluorescent points to be measured, the fluorescent points are binarized under a predetermined analysis condition (luminance, area, circularity) and the fluorescent points corresponding to the quantitation of the measurement object are selected, and counted.

More specifically, the solid phase forming step is shown in the drawing 8B, and in the first step (1), a solid phase forming solution (phase solidifying solution) for solidifying antibodies or antigens on a metal substrate is prepared, and an equal amount (for example, 5 µl) of Ag reagent (2000 ppm silver thiosulfate aqueous solution: pH6) and an antibody-containing buffer solution (25 µg antibody added to 1 ml of phosphate buffer solution of pH7.4:25 µg/ml concentration) are measured by syringe-compression, and mixed by vortexing to prepare a solid phase forming solution. In the third step (3), 10 µl of this solid phase forming solution is collected, dropped on a metal substrate serving as a measurement area with a circular phosphor plate, and left on the metal substrate for 1 minute, and then in the fourth step (4), the remaining solution on the substrate is blown off by air blowing to prepare a solid phase forming substrate (measurement chip).

Samples include nasopharyngeal swab, laryngeal swab, saliva, urine, and feces.

Examples of the fluorescent substances for labeling viral antibodies include those excited by excitation light of 400 nm to 436 nm such as Pacific Blue, those excited by excitation light of 453 nm to 505 nm such as FITC, those excited by excitation light of 485 nm to 566 nm such as TRITC, those excited by excitation light of 488 nm to 706 nm such as APCs, and fluorescent substances excited by excitation light of 732 nm to 784 nm such as IRDye800.

Figure 8A:
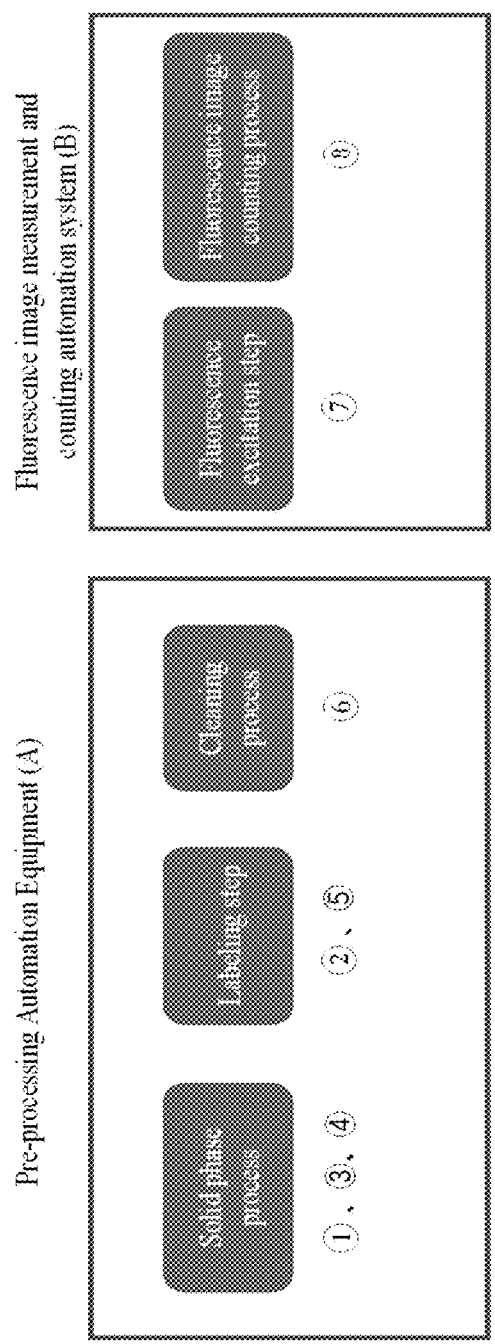
FIG. 8A shows an explanatory diagram of the process automation system of the fluorescence counting method of the present invention, showing that the pre-processing automation apparatus A is composed of a pre-processing automation apparatus A and a fluorescence image counting automation apparatus B, the pre-processing automation apparatus A is composed of a solid phase process, a labeling process, and a washing process, and the fluorescence image counting automation apparatus B is composed of a fluorescence excitation process and a fluorescence image counting process. ① Preparation of solid phase solution with Ag reagent and antibody (or antigen). ② Preparation of labeling solution with sample antigen (sample antibody) and labeled antibody. ③ Drop the solid phase solution onto the metal substrate ⑤ Drop the labeling solution. ④ After 1 minute, the residual liquid was blown off with air to stop coagulation. ⑥ Shake and wash the tip in water, blow off the remaining liquid with air, and dry. ⑦ A plurality of labelled chips are set and delivered by a loader. The binning process increases the sensitivity. Autofocus and measurement of fluorescence images in multiple fields of view with objective lens are performed fully automatically. ⑧ Measured fluorescent images according to analysis conditions (brightness threshold, area value, circularity, etc.). Binarize and count selected fluorescent grains
Figure 8B:
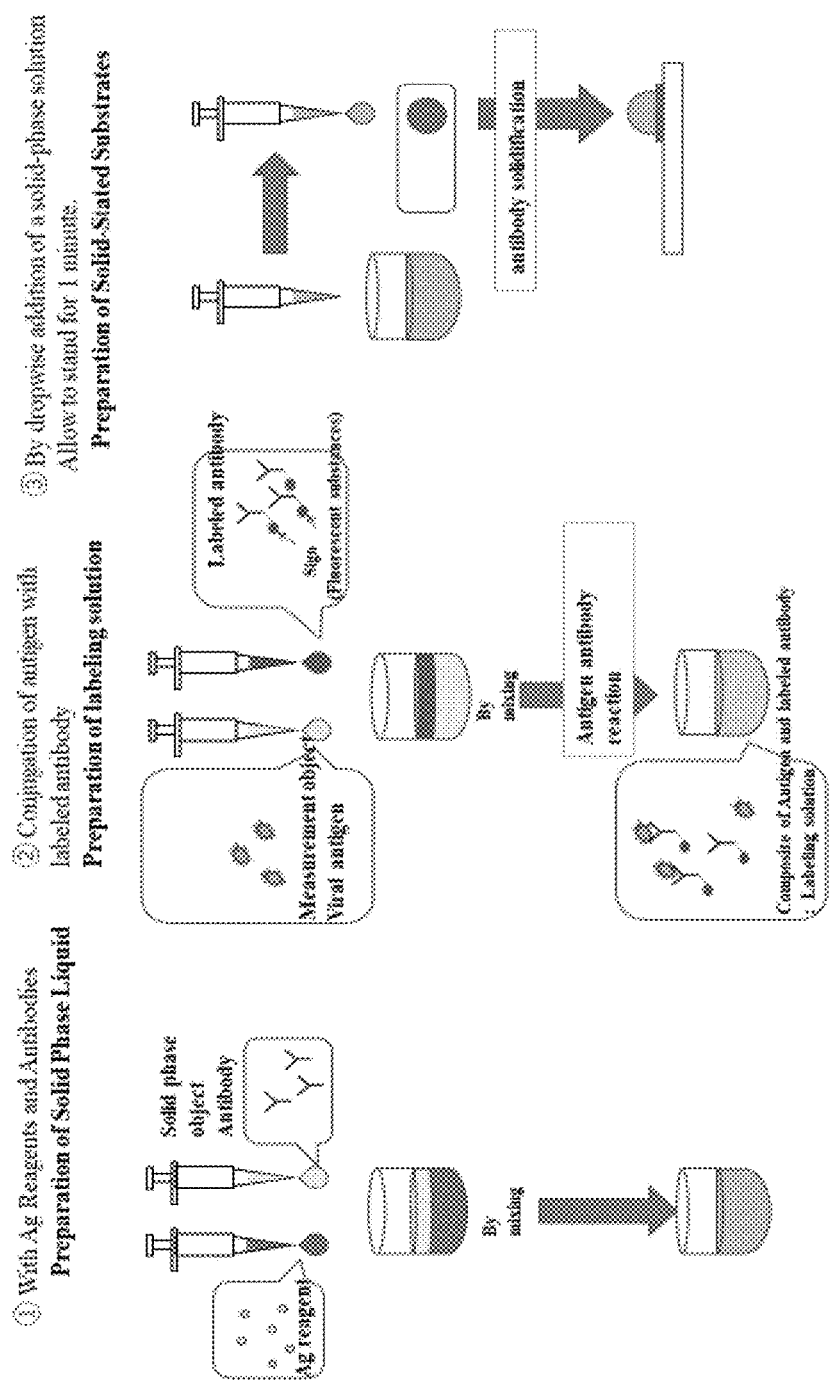
FIG. 8B shows a conceptual diagram of an automated system of a solidification process of an automated system of the present invention, which comprises a first liquid preparation step (1) comprising a fluorescent Ag reagent and an antibody, a solidification step (3) in which a first liquid is dropped onto a substrate, and a finishing step (4) in which a residual liquid is blown off by air blowing after approximately one minute.
Figure 8C:
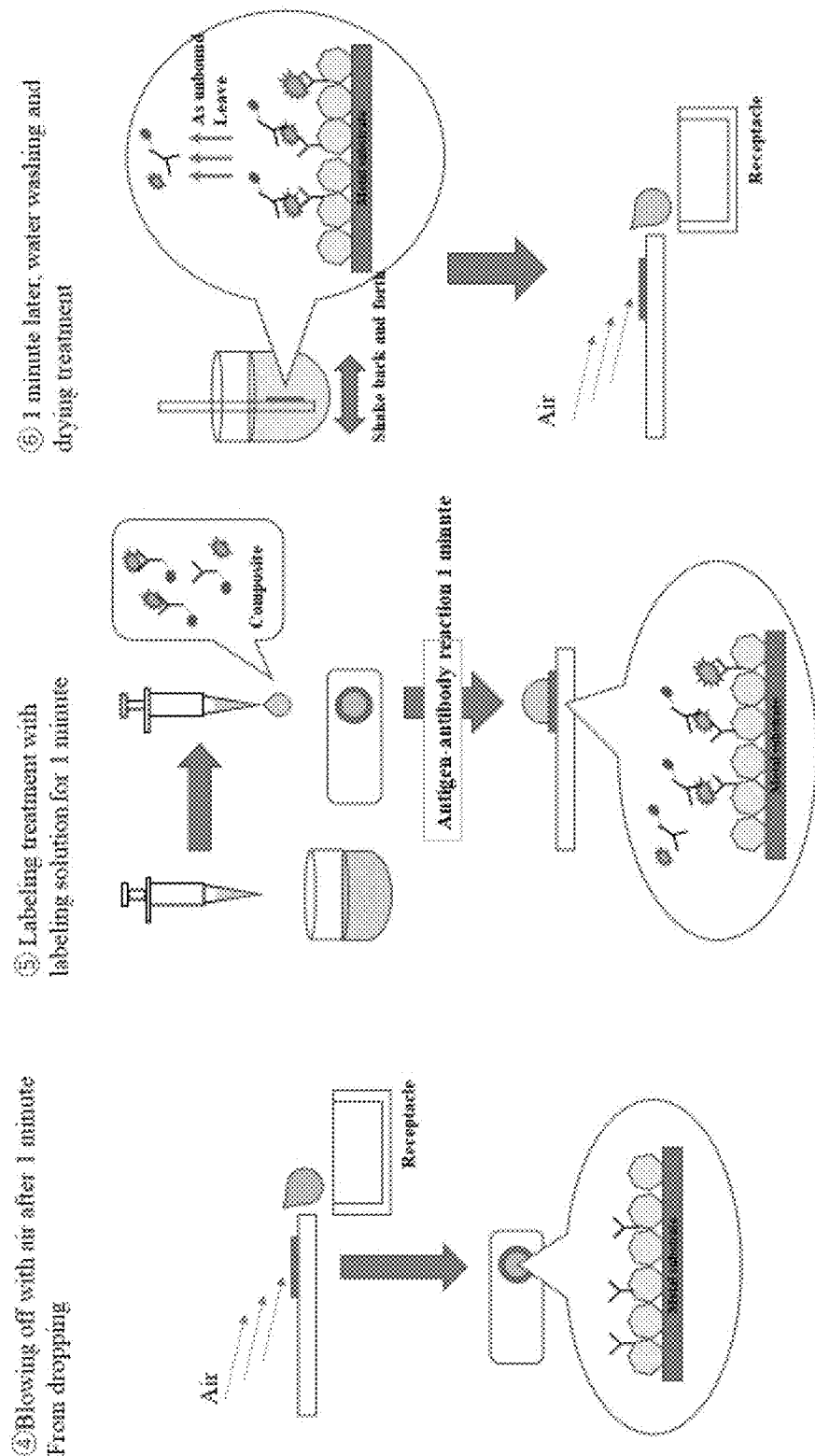
FIG. 8C shows an automated system concept diagram of a labeling process of an automated system of the present invention shows that a second liquid preparation step (2) comprising of an antigen and a labeled antibody, a labeling step (5) in which a second liquid is dropped onto a substrate, and a washing step (6) in which the second liquid is dried by air blowing after washing with water.

Next, in the labeling step of the automated system of the present invention, as shown in FIG. 8C, a labeling liquid preparing step (2) comprising an antigen and a labeling antibody, a labeling step (5) of dropping the second liquid onto the substrate, and a step (6) of washing the unreacted labeling liquid to be dried by air blowing after washing with water.

Drop an appropriate amount of labeled liquid in syringe compression to the measurement chip whose measurement target has been solidified. Labeling liquid varies depending on whether the solid-phase measurement target is an antibody, an antigen, or whether the labeling step is carried out according to a sandwich method, a direct theory method, or an indirect method.

Figure 8D:
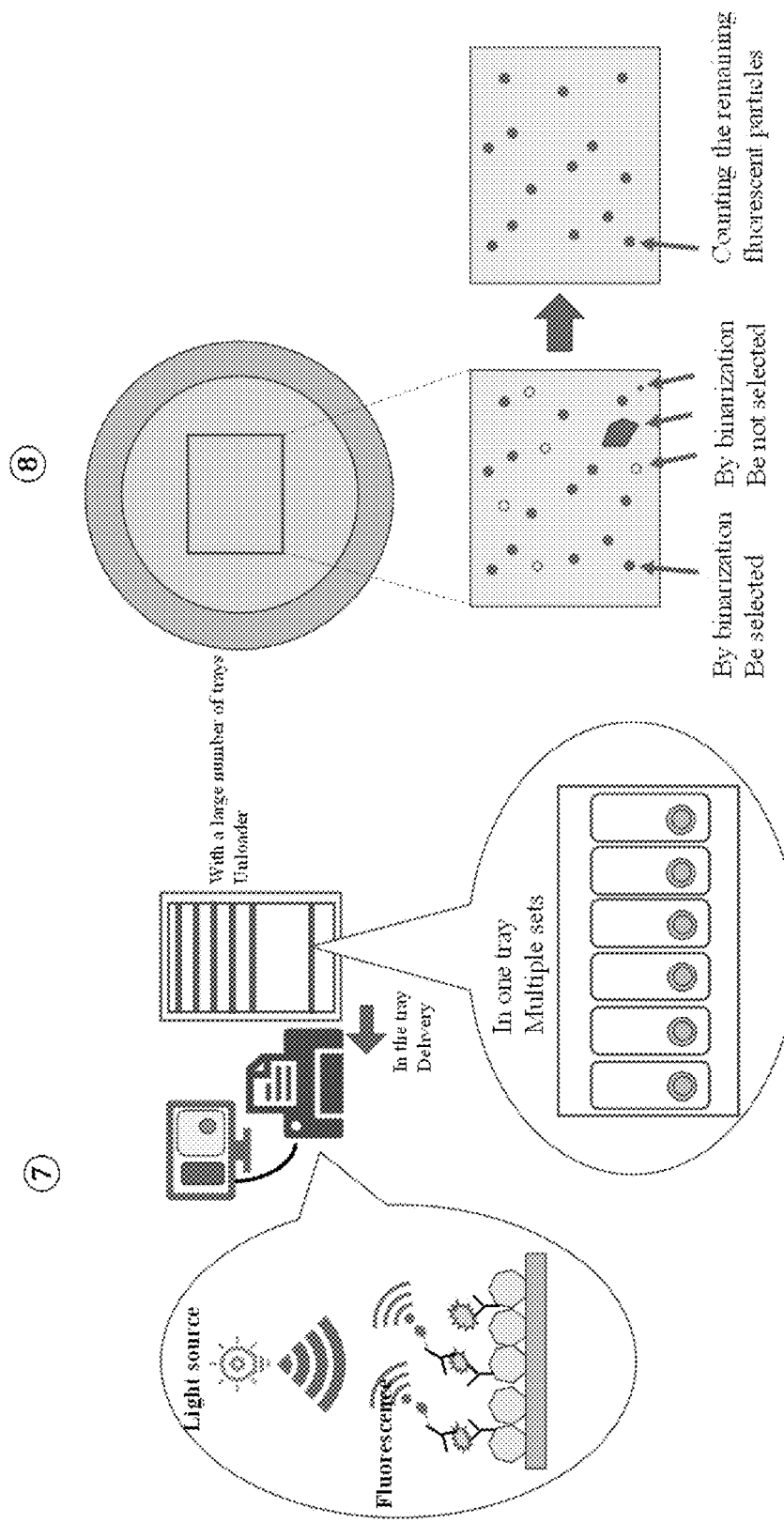
FIG. 8D shows a conceptual diagram of a fluorescence image counting automated system of the present invention, showing that the system comprises a fluorescence excitation step (7) and a fluorescence image counting step (8). The step ⑦ is obtaining Fluorescence-Excited Images 8D. A plurality of chips are set in a tray, and are sent out by a loader with the binning process to increase sensitivity and auto focus. The step ⑧ is Adoption of fluorescence points in fluorescence images (error resolution). Analysis conditions (brightness threshold, area value, circularity, etc.) Counting of fluorescence spots binarized and selected by Automatic Measurement of Fluorescent Images in Multiple Fields of View of Objective Lens

Finally, as shown in the FIG. 8D, the fluorescence image counting automated system of the present invention includes a fluorescence exciting step (7) and a fluorescence image counting step (8).

In the seventh step (7), an excitation light source for irradiating excitation light in a wavelength range suitable for exciting a fluorescent substance in which an antigen or an antibody thereof to be measured is fluorescently labeled, a measurement chip for exciting fluorescence of the labeled fluorescent substance with a quantum crystal of plasmon metal by the excitation light, and a fluorescence microscope for observing a fluorescence image on the measurement chip.

As the excitation light, excitation light of 400 nm to 436 nm for Pacific Blue, excitation light of 453 nm to 505 nm for FITC, excitation light of 485 nm to 566 nm for TRITC, excitation light of 488 nm to 706 nm for APC, and excitation light of 732 nm to 784 nm for IRDye800, etc. can be exemplified.

In the eighth step (8), the fluorescence point in the fluorescence image is binarized and selected under predetermined analysis conditions (selected from brightness, area, and circularity) using Cell Sense, which is Olympus Co. Ltd. made image recognition software, and an appropriate fluorescence point is selected and counted and quantified for quantifying the object of measurement, comprising a means for selecting at least one region in the fluorescence image, a means for binarizing the fluorescence point in the selected region to adopt a fluorescence point equal to or greater than a predetermined threshold, and a quantifying means for counting the fluorescence point.

Example: Comparison Test Results of Covid-19 Positive/Negative According to PCR Method Compared with Those of the Present Invention Method Samples: 50 positive samples and 20 negative samples were provided from the medical center of RYUKYU UNIVERSITY.

Test Process: This comparison tests were conducted by the medical center of RYUKYU UNIVERSITY and Kobe Lab. of Mytech Co. Ltd (Applicant company)

Figure 1:
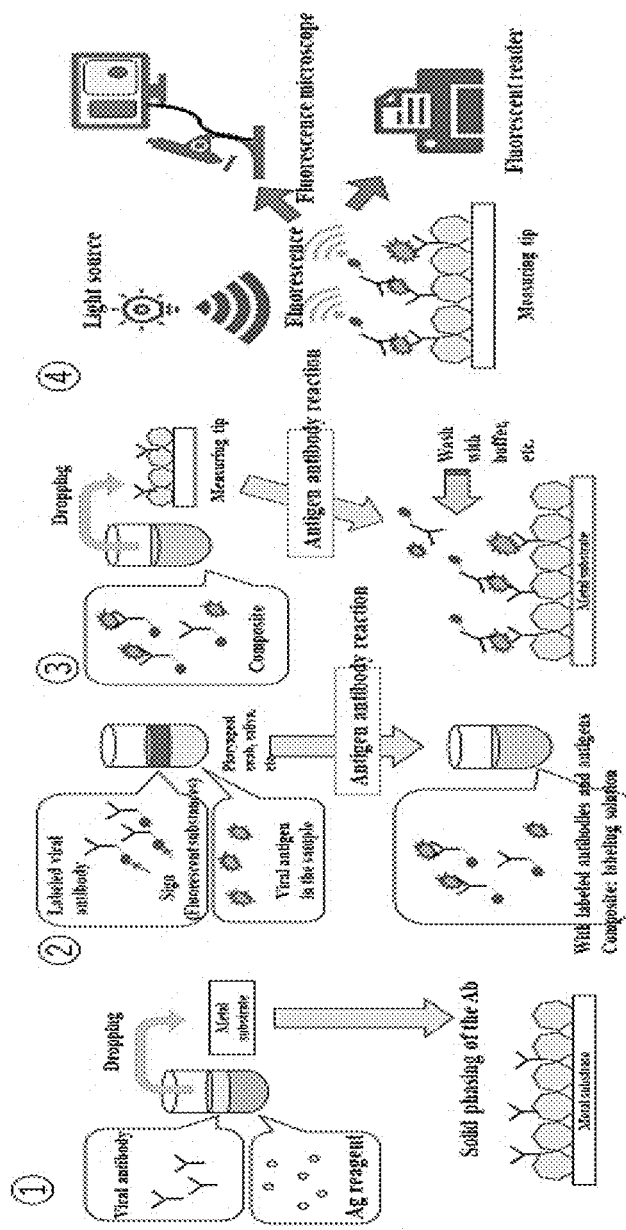
FIG. 1 shows a schematic diagram of Antigen-Antibody Reaction Using Quantum Crystals (Sandwich Method) with Fluorescence Assay Using Fluorescent Labels. It comprises of steps (1) to (4) when the first method (sandwich method) is used for the fluorescent labeling step of the present invention. In the solid phase step (1), an Ag reagent and an antibody of a virus are mixed and dropped onto a metal substrate, and the antibody is simultaneously solidified by quantum crystal aggregation on a metal substrate. Then, in the labeling step (2), an antibody of a virus labeled and a sample are mixed, and a composite is formed with a virus antigen contained in the sample and a labeled antibody by an antigen-antibody reaction. Then, in step (3), the above composite is bound to an antibody on a substrate by an antigen-antibody reaction and labeled, while an unbound composite, an antibody, or the like is washed out with a buffer or the like. In step (4), light of a light source matching a label (fluorescent substance) of an antibody is irradiated to excite, and the label is fluorescent, and fluorescence is detected by a fluorescence microscope or a fluorescence reader.

PCR tests were conducted on 70 Samples by the medical center of RYUKYU UNIVERSITY (Prof. Kinjou) while this invention CV method were conducted on the same samples by Mytech Co. Ltd as shown in FIG. 1 and we compared the positive/negative results of PCR with those of this invention assay.

In the PCR test, 140 µl of the collected samples were mixed with 260 µl of inactivated buffer, and 50 µl of the extraction solution was obtained in an automatic extractor. The PCR assay was performed at 2 well assay per specimen using the reagents recommended by the National Institute of Infectious Diseases.

In this invention assay, 140 µl of the collected samples were mixed with 140 µl of 99.5% ethanol and inactivated, and 5 µl of the inactivated samples were used to count fluorescent grains from the fluorescence images obtained by the antigen-antibody reaction (the inventive sandwich method).

Reagents: Covid-19 Antibody: SARS-CoV-2 spike antibody [CatNo. GTX135356] made by Gene Tex Cooperation, FITC-labeled Covid-19antibody: SARS-CoV-2 spike antibody, [FITC-labeled CatNo. GTX135356] made by Gene Tex Cooperation.

Method Shown in FIG. 1

Firstly Covid-19 antibody (50 µg/ml) was mixed with a quantum crystal reagent solution (the same volume) of 2000 ppm and the mixture was dropped onto a phosphor bronze substrate to prepare a solidified substrate.

Next, a nasopharyngeal wipe solution (specimen) was inactivated by adding an equal volume of 99.5% ethanol, and the specimen was mixed with FITC-labeled Covid-19 antibody (approximately 30.0 µg/ml) and the resultant complex was dropped onto the solidified substrate.

Thirdly unbound complexes and FITC antibodies were washed away with water or buffer.

Finally, the resultant complex on the measurement chip was measured with the Olympus BX63 System Biological Microscope, and grains of fluorescence above an arbitrary threshold in the fluorescence image obtained were counted. (See FIG. 1 Antigen-antibody reaction-sandwich method.)

Analysis method: The fluorescence images obtained were analyzed by the following two patterns (1) and (2) using analysis software of Olympus "Cell Sence".

Analysis conditions (1): (Condition for calculating strongly shining fluorescent grains in the image) Counting the fluorescent grains having a determined brightness or more in the image, Omitting the fluorescent grains having a determined area of 200 µm2 or more in the image.

(The reason: Omitting dust and dirt which cause strong fluorescence much larger than the virus particles, so such a broad area fluorescence should be omitted to prevent erroneous calculations.)

Analysis conditions (2): Counting the fluorescent grains having a determined brightness or more in the image (Same as analysis (1)). Omitting large grains of fluorescent light with an area value of 200 µm2 or more from the calculation (Same as analysis (1)). Omitting small fluorescent grains with an area value of 10 µm2 or less from the calculation. (In the blank (background) made from the buffer, rather small fluorescent grains occur, so that small fluorescent grains with an area of 10 µm2 or less should be omitted in the calculation.)

Results:

"Relative value" in this invention means the number of fluorescent grains substantially corresponding to the number of virus where the number of fluorescent grains caused by the blank or buffer is subtracted from the number of total fluorescent grains because the buffer used for specimen also has some count of small fluorescent grains "Sensitivity" in this invention is defined as the percentage of response rate of the positive=the present inventive method (Mytech method) positive/PCR method positive (%).

Sensitivity=Present Invention Positive/PCR Positive×100(%)

"Specificity" in this invention is defined as the percentage (%) of response rate of the negative=the inventive method (Mitek method) negative/the PCR method negative (%).

Specificity=Mytech Negative/PCR Negative×100(%)

Based on the relative values obtained using the analysis conditions (1) described in Tables 1 to 3, the sensitivity of 98% and specificity of 45% were obtained for the PCR test results if the relative value of 1 or more was considered positive.

The sensitivity and specificity were 94% and 65%, respectively, when a relative value of 2 or more was found to be positive.

Next, based on the relative values obtained by using the analysis conditions (2) in Tables 1 to 3, the sensitivity of 98% and the specificity of 80% were obtained for the PCR test results when a relative value of 1 or more was considered positive. Further, the sensitivity and the specificity were 94% and 100%, respectively, when a relative value of 2 or more was found to be positive.

Consideration of Analysis of the CV Test Method (this Invention Method)

In this study, the fluorescence images (raw data) were analyzed by using analysis software (made in Olympus) in the following two patterns. Each analysis was performed under the conditions described above.

Under Analysis conditions (1), negative response is not good, so it is understood that dust and dirt on the chip will cause strong fluorescence, but they are much larger than virus particles.

Under Analysis conditions (2), positive response at the relative value of 1 or more is better than that at the relative value of 2 or more Disadvantages of the PCR Method and Advantages of the CV Test Method As shown in the above consideration, disadvantages of the PCR method are as follows.

Normally PCR takes 5-6 hours, and even with fully automated PCR, it takes about 75 minutes to detect.

Since dead viruses are also detected, PCR positivity does not necessarily mean COVID-19 positivity. (It also detects viruses that are no longer infectious, so the presence of infection cannot be confirmed. Since PCR amplifies nucleic acids, even a slight contaminant of viral nucleic acid may cause false positive results. And since PCR amplifies nucleic acids, it is not possible to estimate the amount of virus in the specimen.)

Advantages of the CV test method is as follows.

The CV test method takes about 2 minutes (measurement time: 4 seconds). as the entire process. Inactivation is easy by ethanol treatment and only infectious-shaped virus particles can be detected because the virus shape is not destroyed by ethanol treatment.

(Only infectious virus particles are detected, so the actual infection status can be confirmed. Because the collected samples are used without amplification, there are few false positives even if there is a small amount of contamination. This is a much different from PCR. Because the labelled antibodies are visualized to detect infectious virus particles, it is possible to estimate the amount of virus present.)

TABLE 1

| | | Covid-19 PCR data | | | | | | | | | | | | |
|---|---|---|---|---|---|---|---|---|---|---|---|---|---|---|
| | | Number of Specimen | | | | | | | | | | | | |
| | | Buffer | RM1 | RM2 | RM3 | RM4 | RM5 | RM6 | RM7 | RM8 | RM9 | RM10 | RM11 | RM12 |
| | Specimen information | Blank | ○ | ○ | ○ | ○ | ○ | ○ | ○ | ○ | ○ | ○ | ○ | ○ |
| Analysis ① | Number of Count | 8 | 4 | 28 | 27 | 21 | 11 | 11 | 54 | 20 | 11 | 25 | 9 | 36 |
| | Relative value | 0 | −4 | 20 | 19 | 13 | 3 | 3 | 46 | 12 | 3 | 17 | 1 | 28 |
| Analysis ② | Number of Count | 3 | 3 | 17 | 13 | 12 | 5 | 7 | 33 | 11 | 4 | 15 | 6 | 27 |
| | Relative value | 0 | 0 | 14 | 10 | 9 | 2 | 4 | 30 | 8 | 1 | 12 | 3 | 24 |

TABLE 1-continued

Covid-19 PCR data

| | | Buffer | RM13 | RM14 | RM15 | RM16 | RM17 | RM18 | RM19 | RM20 | RM21 | RM22 | RM23 | RM24 |
|---|---|---|---|---|---|---|---|---|---|---|---|---|---|---|
| | Specimen information | Blank | ○ | ○ | ○ | ○ | ○ | ○ | ○ | ○ | ○ | ○ | ○ | ○ |
| Analysis ① | Number of Count | 5 | 26 | 24 | 18 | 64 | 28 | 64 | 82 | 80 | 64 | 30 | 36 | 61 |
| | Relative value | 0 | 21 | 19 | 13 | 59 | 23 | 59 | 77 | 75 | 59 | 25 | 31 | 56 |
| Analysis ② | Number of Count | 0 | 17 | 13 | 10 | 22 | 13 | 24 | 42 | 46 | 28 | 16 | 25 | 25 |
| | Relative value | 0 | 17 | 13 | 10 | 22 | 13 | 24 | 42 | 46 | 28 | 16 | 25 | 25 |

○ Positive of PCR
x Negative of PCR

TABLE 2

Covid-19 PCR data

| | | Buffer | RM25 | RM26 | RM27 | RM28 | RM29 | RM30 | RM31 | RM32 | RM33 | RM34 | RM35 | RM36 |
|---|---|---|---|---|---|---|---|---|---|---|---|---|---|---|
| | Specimen information | Blank | ○ | ○ | ○ | ○ | ○ | ○ | ○ | ○ | ○ | ○ | ○ | ○ |
| Analysis ① | Number of Count | 5 | 22 | 21 | 44 | 15 | 14 | 14 | 11 | 23 | 6 | 10 | 9 | 19 |
| | Relative value | 0 | 17 | 16 | 39 | 10 | 9 | 9 | 6 | 18 | 1 | 5 | 4 | 14 |
| Analysis ② | Number of Count | 0 | 8 | 10 | 31 | 11 | 6 | 12 | 5 | 12 | 1 | 2 | 5 | 9 |
| | Relative value | 0 | 8 | 10 | 31 | 11 | 6 | 12 | 5 | 12 | 1 | 2 | 5 | 9 |

| | | Buffer | RM37 | RM38 | RM39 | RM40 | RM41 | RM42 | RM43 | RM44 | RM45 | RM46 | RM47 | RM48 |
|---|---|---|---|---|---|---|---|---|---|---|---|---|---|---|
| | Specimen information | Blank | ○ | ○ | ○ | ○ | ○ | ○ | ○ | ○ | ○ | ○ | ○ | ○ |
| Analysis ① | Number of Count | 5 | 11 | 32 | 12 | 8 | 12 | 8 | 7 | 14 | 7 | 17 | 14 | 16 |
| | Relative value | 0 | 6 | 27 | 7 | 3 | 7 | 3 | 2 | 9 | 2 | 12 | 9 | 11 |
| Analysis ② | Number of Count | 0 | 7 | 18 | 8 | 4 | 2 | 3 | 3 | 7 | 5 | 8 | 11 | 10 |
| | Relative value | 0 | 7 | 18 | 8 | 4 | 2 | 3 | 3 | 7 | 5 | 8 | 11 | 10 |

○ Positive of PCR
x Negative of PCR

TABLE 4

Covid-19 PCR data

| | | Buffer | RM49 | RM50 | Buffer | RM51 | RM52 | RM53 | RM54 | RM55 | RM56 | RM57 | RM58 |
|---|---|---|---|---|---|---|---|---|---|---|---|---|---|
| | Specimen information | Blank | ○ | ○ | Blank | x | x | x | x | x | x | x | x |
| Analysis ① | Number of Count | 5 | 10 | 36 | 7 | 8 | 8 | 4 | 6 | 14 | 6 | 11 | 9 |
| | Relative value | 0 | 5 | 31 | 0 | 1 | 1 | -3 | -1 | 7 | -1 | 4 | 2 |
| Analysis ② | Number of Count | 0 | 6 | 18 | 6 | 5 | 5 | 4 | 4 | 6 | 3 | 7 | 3 |
| | Relative value | 0 | 6 | 18 | 0 | -1 | -1 | -2 | -2 | 0 | -3 | 1 | -3 |

| | | Buffer | RM59 | RM60 | RM61 | RM62 | RM63 | RM64 | RM65 | RM66 | RM67 | RM68 | RM69 | RM70 |
|---|---|---|---|---|---|---|---|---|---|---|---|---|---|---|
| | Specimen information | Blank | x | x | x | x | x | x | x | x | x | x | x | x |
| Analysis ① | Number of Count | 7 | 4 | 11 | 5 | 6 | 8 | 7 | 9 | 7 | 11 | 8 | 6 | 10 |
| | Relative value | 0 | -3 | 4 | -2 | -1 | 1 | 0 | 2 | 0 | 4 | 1 | -1 | 3 |
| Analysis ② | Number of Count | 6 | 3 | 6 | 5 | 4 | 7 | 6 | 4 | 5 | 7 | 5 | 1 | 7 |
| | Relative value | 0 | -3 | 0 | -1 | -2 | 1 | 0 | -2 | -1 | 1 | -1 | -5 | 1 |

TABLE 4

Covid-19 Comparison of PCR value with present invention

| Analysis method① Sensitivity, Specificity Relative value ≥1 is positive | | | | | Analysis method② Sensitivity, Specificity Relative value ≥1 is positive | | | | |
|---|---|---|---|---|---|---|---|---|---|
| | Mytech inspection① | | | | | Mytech inspection② | | | |
| | positive | negative | | | | positive | negative | | |
| PCR positive | 49 | 1 | Sensitivity | 98% | PCR positive | 49 | 1 | Sensitivity | 98% |
| PCR negative | 11 | 9 | Specificity | 45% | PCR negative | 4 | 16 | Specificity | 80% |
| Relative value ≥2 is positive | | | | | Relative value ≥2 is positive | | | | |
| | Mytech inspection① | | | | | Mytech inspection② | | | |
| | positive | negative | | | | positive | negative | | |
| PCR positive | 47 | 3 | Sensitivity | 94% | PCR positive | 47 | 3 | Sensitivity | 94% |
| PCR negative | 7 | 13 | Specificity | 65% | PCR negative | 0 | 20 | Specificity | 100% |

The present invention can be used for quickly testing for antigens at an early stage of COVID-19 with high accuracy, as well as for testing for acquired antibodies. (Tested on purified influenza virus using Keyence fluorescence microscope BZ-710 and clinical testing at a Japanese medical university is being conducted using COVID-19 pharyngeal swabs.)

Application, Characteristics, and Advantages of the Invention

The invention is fastest known in measurement time. It has simple work procedure. It has mass processing capacity. It is a solid phased antibody produced in 1 minute. The conventional PCR method usually takes 12+ hours. It uses novel substance "quantum crystal" synthesized. It has wide applications varying from antigen and antibody testing, testing for many types of viruses and monitoring of therapeutic effects. Table 5 shows comparison of present invention with the already known COVID-19 methods (Roche and Abbott).

TABLE 5 comparison of present invention with the already known COVID-19 methods (Roche and Abbott).

| | Proteo ® | Roche | Abbott |
|---|---|---|---|
| Testing principle | Fluorescent antigen antibody complex method | PCR method | Immuno-chromatography |
| Accuracy | ◎ 90%-100% | ◎ 90%-100% | × 50%~60% |
| Workflow savings | ◎ Mix reagent and samples-2 steps only (RNA extraction unnecessary) | × RNA extraction and other complex procedure | ◎ Simple test kit |
| Testing time | ◎ about 2 mins (measurement 20 sec.) | × 3.5 hours | ◎ 15-20 min. |
| Sample collection methods | Pharyngeal swab (saliva & urine tests also planned) | Pharyngeal swab | Pharyngeal swab |
| Per test cost | ◎ $50 (estimate) | × PCR testing cost in Japan about $150 | ◎ $5 |

The present invention is very high sensitivity (about 94%) and specificity (about 100%). The entire inspection process of detection and quantification of an antigen is completed in about 2 minutes with (measurement time 4 seconds). The visualization of coronavirus is possible. The quantifying the viral load, the effectiveness of treatment can be confirmed.

One embodiment of invention also can be used for evaluation of drug discovery.

The present invention has no risk of infection from specimen collection to measurement.

The present invention is fastest known measurement time for detection of virus till date. Viruses can be visualized and quantified. It is also very high sensitivity and specificity In the present invention, the antibody solidification in one minute. Whereas the prior arts usually 12+ hours.

All references, including granted patents and patent application publications, referred herein are incorporated herein by reference in their entirety.

The invention claimed is:

1. A method for detecting a virus that causes COVID-19 by detecting a SARS-CoV-2 virus comprising:
   mixing (i) a plasmonic metal complex solution comprising plasmonic metal quantum crystals and (ii) a buffer solution comprising a first antibody, to form a phase solidifying liquor;
   adding the phase solidifying liquor to a metal substrate to initiate coagulation of plasmonic metal quantum crystals on the metal substrate to form coagulated plasmonic metal quantum crystals, wherein the plasmonic metal quantum crystals have an electrode potential more than that of the metal substrate configured to coagulate the plasmonic metal quantum crystals on the metal substrate due to electrode potential difference between the metal substrate and the plasmonic metal quantum crystals,
   wherein the plasmonic metal quantum crystals have (a) a size in a range of 50 nm to 150 nm and are (b) substantially free of agglomeration of coagulated plasmonic metal quantum crystals with each other,
   wherein the first antibody is immobilized on the metal substrate together with the plasmonic metal quantum crystals coagulated on the metal substrate to form an immobilized first antibody;
   labeling a target comprising the SARS-CoV-2 virus with a fluorescent material to form a labeled target;
   capturing the target comprising the SARS-CoV-2 virus to the immobilized first antibody on the coagulated plasmonic metal quantum crystals using an antigen-antibody reaction;

making a fluorescence image of the target captured on the immobilized first antibody on the coagulated plasmonic metal quantum crystals by irradiating an exciting light;

observing the fluorescence image by a microscope;

binarizing the fluorescence image into fluorescence points;

counting the fluorescence points; and quantifying the target;

wherein the target is an outside protein of the SARS-CoV-2 virus, or the target is the SARS-CoV-2 virus itself.

2. The method of claim 1, further comprising blowing an air to stop agglomeration of the coagulated plasmonic metal quantum crystals on the metal substrate.

3. The method of claim 1, wherein pH of the buffer solution is about 7 or more.

4. The method of claim 3, wherein the plasmonic metal complex solution comprises a density of the plasmonic metal quantum crystals in a range of 1000 to 5000 ppm.

5. The method of claim 1, wherein the binarizing comprises performing an analysis condition comprising one or more of a brightness, an area of the fluorescence image, and a circularity of the fluorescence points.

6. The method of claim 1, wherein the target is inactivated using a solution comprising ethanol.

7. The method of claim 1, wherein the target is labelled by a sandwich method.

\* \* \* \* \*